(12) United States Patent
Ley et al.

(10) Patent No.: US 7,550,427 B2
(45) Date of Patent: Jun. 23, 2009

(54) POLY-PEGYLATED PROTEASE INHIBITORS

(75) Inventors: Arthur C. Ley, Newton, MA (US); Aaron K Sato, Somerville, MA (US); Robert C. Ladner, Ijamsville, MD (US); Mark Stochl, North Attleboro, MA (US)

(73) Assignee: Dyax Corp., Cambridge, MA (US)

( * ) Notice: Subject to any disclaimer, the term of this patent is extended or adjusted under 35 U.S.C. 154(b) by 0 days.

(21) Appl. No.: 11/458,773

(22) Filed: Jul. 20, 2006

(65) Prior Publication Data

US 2007/0041959 A1 Feb. 22, 2007

Related U.S. Application Data

(63) Continuation of application No. 10/931,153, filed on Aug. 30, 2004, now abandoned.

(60) Provisional application No. 60/498,845, filed on Aug. 29, 2003, provisional application No. 60/598,967, filed on Aug. 4, 2004.

(51) Int. Cl.
*A61K 38/55* (2006.01)
*C07K 14/81* (2006.01)

(52) U.S. Cl. ............................ 514/2; 530/324
(58) Field of Classification Search .................... 514/12
See application file for complete search history.

(56) References Cited

U.S. PATENT DOCUMENTS

| | | | |
|---|---|---|---|
| 5,166,133 A | 11/1992 | Houston et al. | |
| 5,223,409 A | 6/1993 | Ladner et al. | |
| 5,278,144 A | 1/1994 | Wolf et al. | |
| 5,278,285 A | 1/1994 | Ebbers et al. | |
| 5,373,090 A | 12/1994 | Norris et al. | |
| 5,446,090 A | 8/1995 | Harris | |
| 5,576,294 A | 11/1996 | Norris et al. | |
| 5,583,107 A | 12/1996 | Wolf et al. | |
| 5,589,359 A | 12/1996 | Innis et al. | |
| 5,663,143 A | 9/1997 | Ley et al. | |
| 5,672,662 A | 9/1997 | Harris et al. | |
| 5,695,760 A | 12/1997 | Faanes et al. | |
| 5,696,088 A | 12/1997 | Innis | |
| 5,719,041 A | 2/1998 | Lazarus et al. | |
| 5,736,364 A | 4/1998 | Kelley et al. | |

(Continued)

FOREIGN PATENT DOCUMENTS

EP 301 122 2/1989

(Continued)

OTHER PUBLICATIONS

Appendix A—alignment of SEQ ID No. 23 (DX-890) and SEQ ID No. 12 (ITI-2). No date.*

(Continued)

*Primary Examiner*—Nashaat T Nashed
*Assistant Examiner*—William W Moore
(74) *Attorney, Agent, or Firm*—Lowrie, Lando & Anastasi, LLP

(57) ABSTRACT

Disclosed are compounds that comprise: (i) a Kunitz domain polypeptide that comprises a Kunitz domain that binds to and inhibits a protease; and (ii) a plurality of polyethylene glycol moieties attached to the Kunitz domain polypeptide. Each accessible primary amine of the Kunitz domain polypeptide can be attached to one of the moieties. Also disclosed are related methods.

48 Claims, 12 Drawing Sheets

U.S. PATENT DOCUMENTS

| | | | |
|---|---|---|---|
| 5,739,208 A | 4/1998 | Harris | |
| 5,780,265 A | 7/1998 | Denis et al. | |
| 5,786,328 A | 7/1998 | Denis et al. | |
| 5,795,865 A | 8/1998 | Markland et al. | |
| 5,795,954 A | 8/1998 | Lazarus et al. | |
| 5,804,376 A | 9/1998 | Braxton et al. | |
| 5,843,895 A | 12/1998 | Lazarus et al. | |
| 5,853,723 A | 12/1998 | Jacobs et al. | |
| 5,900,461 A | 5/1999 | Harris | |
| 5,932,462 A | 8/1999 | Harris | |
| 5,990,237 A | 11/1999 | Bentley et al. | |
| 5,994,125 A | 11/1999 | Markland et al. | |
| 6,001,596 A | 12/1999 | Hillman et al. | |
| 6,004,579 A | 12/1999 | Bathurst et al. | |
| 6,010,880 A | 1/2000 | Markland et al. | |
| 6,013,448 A | 1/2000 | Braxton et al. | |
| 6,057,287 A | 5/2000 | Markland et al. | |
| 6,071,723 A | 6/2000 | Markland et al. | |
| 6,087,473 A | 7/2000 | Conklin et al. | |
| 6,103,499 A | 8/2000 | Markland et al. | |
| 6,113,896 A | 9/2000 | Lazarus et al. | |
| 6,180,607 B1 | 1/2001 | Davies et al. | |
| 6,214,966 B1 | 4/2001 | Harris | |
| 6,258,351 B1 | 7/2001 | Harris | |
| 6,333,402 B1 | 12/2001 | Markland et al. | |
| 6,348,558 B1 | 2/2002 | Harris et al. | |
| 6,362,254 B2 | 3/2002 | Harris et al. | |
| 6,362,276 B1 | 3/2002 | Harris et al. | |
| 6,376,604 B2 | 4/2002 | Kozlowski | |
| 6,413,507 B1 | 7/2002 | Bentley et al. | |
| 6,423,498 B1 | 7/2002 | Markland et al. | |
| 6,432,397 B1 | 8/2002 | Harris | |
| 6,455,639 B1 | 9/2002 | Yasukohchi et al. | |
| 6,515,100 B2 | 2/2003 | Harris | |
| 6,576,235 B1 | 6/2003 | Williams et al. | |
| 6,610,281 B2 | 8/2003 | Harris | |
| 6,624,246 B2 | 9/2003 | Kozlowski | |
| 6,664,331 B2 | 12/2003 | Harris et al. | |
| 6,710,125 B2 | 3/2004 | Kozlowski | |
| 6,774,180 B2 | 8/2004 | Kozlowski et al. | |
| 6,783,965 B1 | 8/2004 | Sherman et al. | |
| 6,814,982 B2* | 11/2004 | Poncin et al. | 424/499 |
| 6,989,369 B2* | 1/2006 | Ladner et al. | 514/12 |
| 7,078,383 B2* | 7/2006 | Ley et al. | 514/12 |
| 2002/0102703 A1* | 8/2002 | Sheppard et al. | 435/226 |
| 2002/0111460 A1 | 8/2002 | Holloway | |
| 2003/0100070 A1 | 5/2003 | Holloway et al. | |
| 2003/0153046 A1* | 8/2003 | Jensen et al. | 435/69.1 |
| 2003/0175919 A1 | 9/2003 | Ley et al. | |
| 2003/0223977 A1 | 12/2003 | Ley et al. | |
| 2004/0038893 A1 | 2/2004 | Ladner et al. | |
| 2004/0049018 A1* | 3/2004 | Bailon et al. | 530/402 |
| 2004/0053206 A1 | 3/2004 | Cicardi et al. | |
| 2004/0062746 A1 | 4/2004 | Martinez et al. | |
| 2004/0062748 A1 | 4/2004 | Martinez et al. | |
| 2004/0106747 A1* | 6/2004 | Bailon et al. | 525/418 |
| 2004/0126361 A1 | 7/2004 | Saifer et al. | |
| 2004/0171794 A1 | 9/2004 | Ladner et al. | |
| 2006/0228331 A1* | 10/2006 | Peschke et al. | 424/85.2 |
| 2007/0020252 A1 | 1/2007 | Ladner et al. | |
| 2007/0065407 A1* | 3/2007 | Patten et al. | 424/85.7 |
| 2007/0100133 A1* | 5/2007 | Beals et al. | 530/350 |

FOREIGN PATENT DOCUMENTS

| | | |
|---|---|---|
| WO | WO 93/14120 | 7/1993 |
| WO | WO 93/14121 | 7/1993 |
| WO | WO 93/14122 | 7/1993 |
| WO | WO 95/21601 | 8/1995 |
| WO | 9620278 | 7/1996 |
| WO | 02092147 | 11/2002 |
| WO | 02094200 | 11/2002 |
| WO | 2005021556 | 3/2005 |
| WO | 2005021557 | 3/2005 |
| WO | WO 2005/021556 | 3/2005 |

OTHER PUBLICATIONS

Basu, A., et al., 2006, "Structure-function engineering of interferon-[beta]-1b for improving stability, solubility, potency, immunogenicity, and pharmacokinetic properties by site-selective mono-PEGylation", Bioconjugate Chemistry, vol. 17, pp. 618-630.*

Dhalluin, C., et al., 2005, "Structural, Kinteic, and thermodynamic analysis of the binding of the 40kDa PEG-interferon-[alpha]-2a and its individual positional isomers to the extracellular domain of the receptor IFNAR2", Bioconjugate Chemistry, vol. 16, pp. 518-527.*

Cantor, et al., "Elastin and Elastases in Lung Disease", Chapter 16, vol. II, p. 159-168.

Depiopharm Brochure "Engineered Protein Inhibitor of Human Neutrophil Elastase EPI-hNE4 (DX-890)" Dated Oct. 2004, printed from www.debio.com/e/pdf/fiche_epi_hne4_e.pdf.

Delacourt et al. "Protection against acute lung injury by intravenons or intratracheal pretreatment with EPI-HNE-4, a new potent neutrophil elastase inhibitor." Am J Respir Cell Mol Biol. Mar. 2002;26(3):290-7.

Delgado et al., "The Uses and Properties of PEG-linked Proteins", Critical Review in Therapeutic Drug Carrier Systems, vol. 9, Nos. 3, 4, pp. 249-304, (1992).

Donnelly et al. (2003) "Therapy for chronic obstructive pulmonary disease in the $21^{st}$ century" Drugs 63:1973-98.

Goodson, R. et al., "Site-Directed Pegylation of Recombinant Interleukin-2 at its Glycosylation Site", Bio Technology, vol. 8, 343-346, (1990).

Katre, N. V. et al., "Chemical modification of recombinant interleukin 2 by polyethylene glycol increases its potency in the murine Meth A sarcoma model", Proc. Natl. Acad. Sci., 84, 1487-1491, (1987).

Katre N. V., J., "Immunogenicity of Recombinant Il-2 Modified by Covalent Attachment of Polyethylene Glycol". Immunol. 144:209-213 (1990).

Kelly, et al., "Diabetes Insipidus in Uricase-Deficient Mice: A Model for Evaluating Therapy with Poly(Ethylene Glycol)-Modified", J Am Soc Nephrol. 12:1001-1009, (2001).

Markland W et al., "Selection for protease inhibitors using bacteriophage display." Methods Enzymol. 1996;267:28-51.

Maxfield, et al., "Conformation of poly(ethylene oxide) in the solid state, melt and solution measured by Raman scattering", Polymer 16,505-509 (1975).

Molineux, "Pegylation: Engineering Improved Pharmaceuticals for Enhanced Therapy", Cancer Treatment Reviews, Apr. 2002, 28, Supplement A: 13-16.

Poznansky, M. J. et al., "Growth hormone-albumin conjugates Reduced renal toxicity and altered plasma clearance", vol. 239:18-22 (1988).

Roberts, et al., "Chemistry for peptide and protein PEGylation", Advanced Drug Delivery Reviews 54:459-476 (2002).

Abuchowski, A. et al., "Alteration of Immunological Properties of Bovine-Serum Albumin by Covalent Attachment of Polyethylene Glycol", J. Bio. Chem., 252, 3578-3581, (1977).

Abuchowski, A. et al., "Cancer Therapy with Chemically Modified Enzymes. I. Antitumor Properties of Polyethylene Glycol-Asparaginase Conjugates", Cancer Biochem. Biophys. vol. 7, 175-186, (1984).

Abuchkowski, A. et al., "Effect of Covalent Attachment of Polyethylene Glycol on Immunogenicity and Circulating Life of Bovine", J. Biol. Chem. 252:3582-3586 (1977).

Sherman, et al., Chapter 11: "Conjugation of High-Molecular Weight Poly(ethylene glycol) to Cytokines: Granulocyte-Macrophage Colony-Stimulating Factors as Model Substrates", American Chemical Society, 155-169 (1997).

Travis, et al., "Pulmonary Perspective: Potential Problems in Designing Elastase Inhibitors for Therapy", Am. Rev. Respir. Dig. 143: 1412-1415 (1991).

Wark et al. (2002) DX-890, iDRUGS, 5:586-9.

Xu et al. "The crystal structure of bikunin from the inter-alpha-inhibitor complex: a serine protease inhibitor with two Kunitz domains." J Mol Biol. Mar. 13, 1998;276(5):955-66.

Enzon Pharmaceuticals, Macromolecular Engineering Technologies, pp. 1-14, (2004).

Nektar™—Transforming Therapeutics, Nektar Molecular Engineering: Polyethylene Glycol and Derivatives for Advanced PEGylation, pp. 1-20, (catalog-2003).

Nektar™—Transforming Therapeutics, Nektar Advanced PEGylation: Polyethylene Glycol and Derivatives for Advanced PEGylation, pp. 1-24, (Catalog - 2004).

NOF Corporation, PEG Derivatives, Phospholipid and Drug Delivery Materials for Pharmaceuticals, pp. 1-46, (Catalog 2003-1st).

NOF Corporation, PEG Derivatives, Phospholipid and Drug Delivery Materials for Pharmaceuticals, pp. 1-50, (Catalog 2003-2nd).

NOF Corporation, "PEG Derivatives, Phospholipid and Drug Delivery Materials for Pharmaceutical Products and Formulation," pp. 1-59, (Catalog Ver. 8 - Apr. 2006).

Polypure, Products; PEG amines; PEG acids and amino acids; PEG thiols and disulfides; BIOTINS, (Apr. 2004).

Polypure, Products; PEG amines; PEG acids and amino acids; PEG thiols and disulfides; BIOTINS, (Apr. 2005).

Quanta Biodesign, Labeling, Derivatization and Crosslinking Reagents for Biological and Related Materials with dPEG™, pp. 1-38, (Mar. 12, 2004).

Quanta Biodesign, Labeling, Modification and Crosslinking Reagents incorporating our unique monodispersed dPEG™, pp. 1-31, (Nov. 5, 2004).

Quanta Biodesign, Leading innovator, producer and provider of monodisperse discrete PEG™ (dPEG™) derivatives, (Product Catalog), pp. 1-51, (Updated: Jul. 18, 2005).

Quanta Biodesign, Leading innovator, producer and provider of monodisperse discrete PEG™ (dPEG™) derivatives, (Product Catalog), pp. 1-51, (Updated: Nov. 17, 2005).

Shearwater Polymers, Inc. pp. 2-49 (Catalog - Mar. 1995).

Shearwater Polymers, Inc., Polythylene Glycol and Derivatives, pp. 1-50, (Catalog - Jul. 1997).

Shearwater Polymers, Inc., Polythylene Glycol Derivatives: Functionalized Biocompatible Polymers for Research and Pharmaceuticals, pp. 1-50, (Catalog - 2000).

Shearwater Corporation, Polythylene Glycol and Derivatives for Biomedical Applications, pp. 1-17, (Catalog - 2001).

International Search Report from PCT Application No. PCT/US2004/028256, 2005.

Supplementary European Search Report dated Jan. 19, 2009 from EP App. No. 04782687.0.

Supplementary European Search Report dated Jan. 20, 2009 from EP App. No. 04786615.7.

Veronese, F.M., "Peptide and protein PEGylation: a review of problems and solutions", Biomaterials, vol. 22, No. 5, Mar. 1, 2001, pp. 405-417.

* cited by examiner

PEGylation Scheme

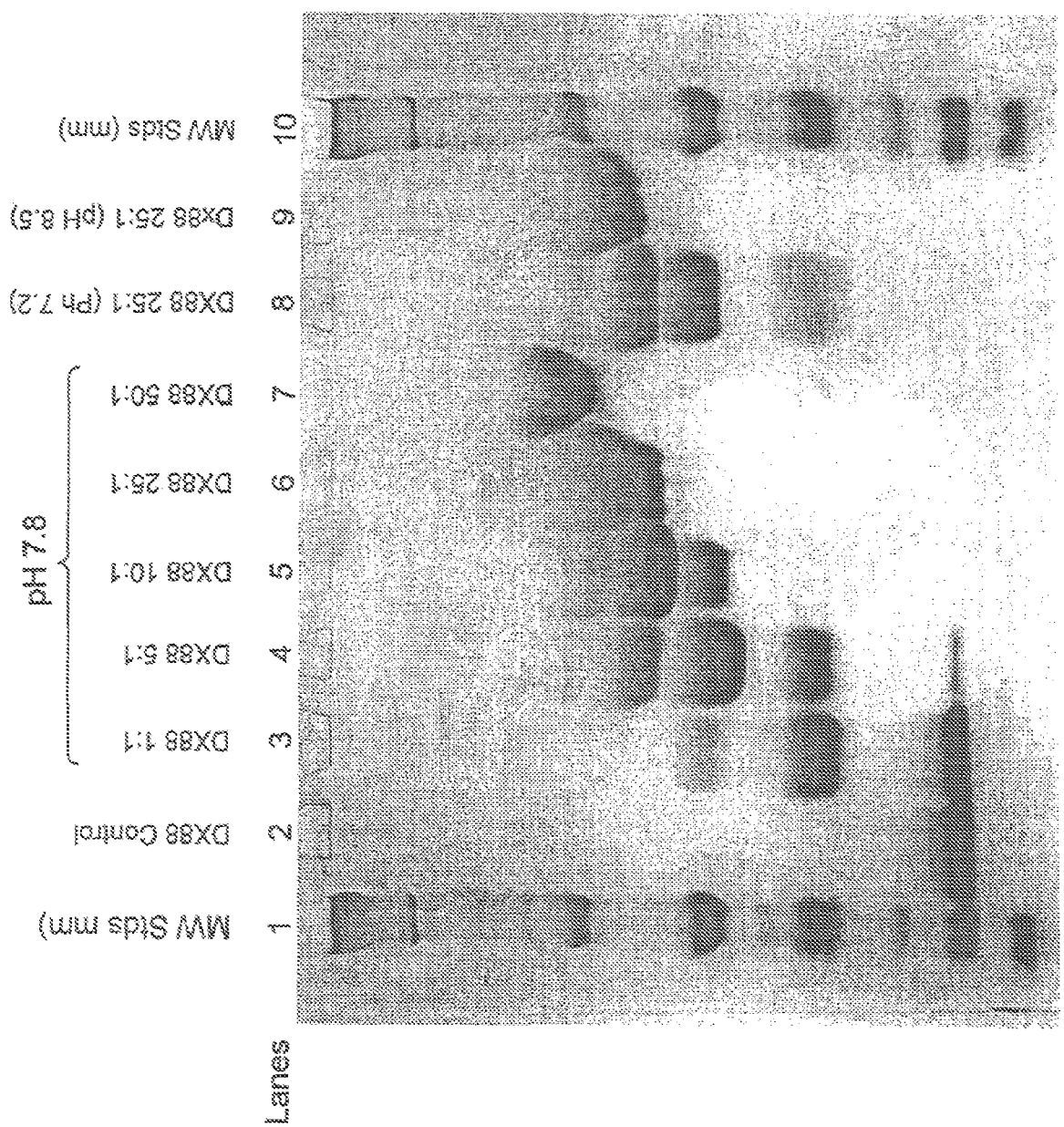

SEQUENCE LISTING

<160> NUMBER OF SEQ ID NOS: 25

<210> SEQ ID NO 1
<211> LENGTH: 304
<212> TYPE: PRT
<213> ORGANISM: Homo sapiens

<400> SEQUENCE: 1

Met Ile Tyr Thr Met Lys Lys Val His Ala Leu Trp Ala Ser Val Cys
 1               5                  10                  15

Leu Leu Leu Asn Leu Ala Pro Ala Pro Leu Asn Ala Asp Ser Glu Glu
             20                  25                  30

```
Asp Glu Glu His Thr Ile Ile Thr Asp Thr Glu Leu Pro Pro Leu Lys
             35                  40                  45

Leu Met His Ser Phe Cys Ala Phe Lys Ala Asp Asp Gly Pro Cys Lys
 50                  55                  60

Ala Ile Met Lys Arg Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                 85                  90                  95

Leu Glu Glu Cys Lys Lys Met Cys Thr Arg Asp Asn Ala Asn Arg Ile
                100                 105                 110

Ile Lys Thr Thr Leu Gln Gln Glu Lys Pro Asp Phe Cys Phe Leu Glu
            115                 120                 125

Glu Asp Pro Gly Ile Cys Arg Gly Tyr Ile Thr Arg Tyr Phe Tyr Asn
            130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
                180                 185                 190

Ala Val Asn Asn Ser Leu Thr Pro Gln Ser Thr Lys Val Pro Ser Leu
            195                 200                 205

Phe Glu Phe His Gly Pro Ser Trp Cys Leu Thr Pro Ala Asp Arg Gly
            210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
                260                 265                 270

Gln Arg Ile Ser Lys Gly Gly Leu Ile Lys Thr Lys Arg Lys Arg Lys
            275                 280                 285

Lys Gln Arg Val Lys Ile Ala Tyr Glu Glu Ile Phe Val Lys Asn Met
290                 295                 300

<210> SEQ ID NO 2
<211> LENGTH: 58
<212> TYPE: PRT
<213> ORGANISM: Bos taurus

<400> SEQUENCE: 2

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
             35                  40                  45

Glu Asp Cys Met Arg Thr Cys Gly Gly Ala
     50                  55

<210> SEQ ID NO 3
<211> LENGTH: 58
<212> TYPE: PRT
<213> ORGANISM: Homo sapiens

<400> SEQUENCE: 3
```

```
Ser Asp Asp Pro Cys Ser Leu Pro Leu Asp Glu Gly Ser Cys Thr Ala
 1               5                  10                  15

Tyr Thr Leu Arg Trp Tyr His Arg Ala Val Thr Glu Ala Cys His Pro
             20                  25                  30

Phe Val Tyr Gly Gly Cys Gly Asn Ala Asn Arg Phe Gly Thr Arg
         35                  40                  45

Glu Ala Cys Glu Arg Arg Cys Pro Pro Arg
 50                  55

<210> SEQ ID NO 4
<211> LENGTH: 58
<212> TYPE: PRT
<213> ORGANISM: Homo sapiens

<400> SEQUENCE: 4

Asn Ala Glu Ile Cys Leu Leu Pro Leu Asp Tyr Gly Pro Cys Arg Ala
 1               5                  10                  15

Leu Leu Leu Arg Tyr Tyr Tyr Asp Arg Tyr Thr Gln Ser Cys Arg Gln
             20                  25                  30

Phe Leu Tyr Gly Gly Cys Glu Gly Asn Ala Asn Asn Phe Tyr Thr Trp
         35                  40                  45

Glu Ala Cys Asp Asp Ala Cys Trp Arg Ile
 50                  55

<210> SEQ ID NO 5
<211> LENGTH: 58
<212> TYPE: PRT
<213> ORGANISM: Homo sapiens

<400> SEQUENCE: 5

Val Arg Glu Val Cys Ser Glu Gln Ala Glu Thr Gly Pro Cys Arg Ala
 1               5                  10                  15

Met Ile Ser Arg Trp Tyr Phe Asp Val Thr Glu Gly Lys Cys Ala Pro
             20                  25                  30

Phe Phe Tyr Gly Gly Cys Gly Gly Asn Arg Asn Asn Phe Asp Thr Glu
         35                  40                  45

Glu Tyr Cys Met Ala Val Cys Gly Ser Ala
 50                  55

<210> SEQ ID NO 6
<211> LENGTH: 58
<212> TYPE: PRT
<213> ORGANISM: Homo sapiens

<400> SEQUENCE: 6

Tyr Glu Glu Tyr Cys Thr Ala Asn Ala Val Thr Gly Pro Cys Arg Ala
 1               5                  10                  15

Ser Phe Pro Arg Trp Tyr Phe Asp Val Glu Arg Asn Ser Cys Asn Asn
             20                  25                  30

Phe Ile Tyr Gly Gly Cys Arg Gly Asn Lys Asn Ser Tyr Arg Ser Glu
         35                  40                  45

Glu Ala Cys Met Leu Arg Cys Phe Arg Gln
 50                  55

<210> SEQ ID NO 7
<211> LENGTH: 58
<212> TYPE: PRT
<213> ORGANISM: Homo sapiens
```

-continued

<400> SEQUENCE: 7

Lys Glu Asp Ser Cys Gln Leu Gly Tyr Ser Ala Gly Pro Cys Met Gly
1               5                   10                  15

Met Thr Ser Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
        35                  40                  45

Lys Glu Cys Leu Gln Thr Cys Arg Thr Val
    50                  55

<210> SEQ ID NO 8
<211> LENGTH: 59
<212> TYPE: PRT
<213> ORGANISM: Homo sapiens

<400> SEQUENCE: 8

Phe Gln Glu Pro Cys Met Leu Pro Val Arg His Gly Asn Cys Asn His
1               5                   10                  15

Glu Ala Gln Arg Trp His Phe Asp Phe Lys Asn Tyr Arg Cys Thr Pro
            20                  25                  30

Phe Lys Tyr Arg Gly Cys Glu Gly Asn Ala Asn Asn Phe Leu Asn Glu
        35                  40                  45

Asp Ala Cys Arg Thr Ala Cys Met Leu Ile Arg
    50                  55

<210> SEQ ID NO 9
<211> LENGTH: 56
<212> TYPE: PRT
<213> ORGANISM: Homo sapiens

<400> SEQUENCE: 9

Thr Glu Asp Tyr Cys Leu Asn Lys Val Gly Arg Cys Arg Gly Ser Phe
1               5                   10                  15

Pro Arg Trp Tyr Tyr Asp Pro Thr Glu Gln Ile Cys Lys Ser Phe Val
            20                  25                  30

Tyr Gly Gly Cys Leu Gly Asn Lys Asn Asn Tyr Leu Arg Glu Glu Glu
        35                  40                  45

Cys Ile Leu Ala Cys Arg Gly Val
    50                  55

<210> SEQ ID NO 10
<211> LENGTH: 58
<212> TYPE: PRT
<213> ORGANISM: Homo sapiens

<400> SEQUENCE: 10

Asp Lys Gly His Cys Val Asp Leu Pro Asp Thr Gly Leu Cys Lys Glu
1               5                   10                  15

Ser Ile Pro Arg Trp Tyr Tyr Asn Pro Phe Ser Glu His Cys Ala Arg
            20                  25                  30

Phe Thr Tyr Gly Gly Cys Tyr Gly Asn Lys Asn Asn Phe Glu Glu Glu
        35                  40                  45

Gln Gln Cys Leu Glu Ser Cys Arg Gly Ile
    50                  55

<210> SEQ ID NO 11
<211> LENGTH: 56
<212> TYPE: PRT
<213> ORGANISM: Homo sapiens

<400> SEQUENCE: 11

Ile Pro Ser Phe Cys Pro Lys Asp Glu Gly Leu Cys Ser Ala Asn Val
1               5                   10                  15

Thr Arg Tyr Tyr Phe Asn Pro Arg Tyr Arg Thr Cys Asp Ala Phe Thr
            20                  25                  30

Tyr Thr Gly Cys Gly Gly Asn Asp Asn Asn Phe Val Ser Arg Glu Asp
        35                  40                  45

Cys Lys Arg Ala Cys Ala Lys Ala
    50                  55

<210> SEQ ID NO 12
<211> LENGTH: 56
<212> TYPE: PRT
<213> ORGANISM: Homo sapiens

<400> SEQUENCE: 12

Ala Ala Cys Asn Leu Pro Ile Val Arg Gly Pro Cys Arg Ala Phe Ile
1               5                   10                  15

Gln Leu Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 13
<211> LENGTH: 58
<212> TYPE: PRT
<213> ORGANISM: Homo sapiens

<400> SEQUENCE: 13

Ile His Asp Phe Cys Leu Val Ser Lys Val Val Gly Arg Cys Arg Ala
1               5                   10                  15

Ser Met Pro Arg Trp Trp Tyr Asn Val Thr Asp Gly Ser Cys Gln Leu
            20                  25                  30

Phe Val Tyr Gly Gly Cys Asp Gly Asn Ser Asn Asn Tyr Leu Thr Lys
        35                  40                  45

Glu Glu Cys Leu Lys Lys Cys Ala Thr Val
    50                  55

<210> SEQ ID NO 14
<211> LENGTH: 58
<212> TYPE: PRT
<213> ORGANISM: Homo sapiens

<400> SEQUENCE: 14

Val Lys Ala Val Cys Ser Gln Glu Ala Met Thr Gly Pro Cys Arg Ala
1               5                   10                  15

Val Met Pro Arg Trp Tyr Phe Asp Leu Ser Lys Gly Lys Cys Val Arg
            20                  25                  30

Phe Ile Tyr Gly Gly Cys Gly Gly Asn Arg Asn Asn Phe Glu Ser Glu
        35                  40                  45

Asp Tyr Cys Met Ala Val Cys Lys Ala Met
    50                  55

<210> SEQ ID NO 15
<211> LENGTH: 58
<212> TYPE: PRT

<213> ORGANISM: Homo sapiens

<400> SEQUENCE: 15

Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg
            20                  25                  30

Phe Lys Tyr Gly Gly Cys Leu Gly Asn Met Asn Asn Phe Glu Thr Leu
        35                  40                  45

Glu Glu Cys Lys Asn Ile Cys Glu Asp Gly
    50                  55

<210> SEQ ID NO 16
<211> LENGTH: 61
<212> TYPE: PRT
<213> ORGANISM: Homo sapiens

<400> SEQUENCE: 16

Val Pro Lys Val Cys Arg Leu Gln Val Ser Val Asp Asp Gln Cys Glu
1               5                   10                  15

Gly Ser Thr Glu Lys Tyr Phe Phe Asn Leu Ser Ser Met Thr Cys Glu
            20                  25                  30

Lys Phe Phe Ser Gly Gly Cys His Arg Asn Arg Ile Glu Asn Arg Phe
        35                  40                  45

Pro Asp Glu Ala Thr Cys Met Gly Phe Cys Ala Pro Lys
    50                  55                  60

<210> SEQ ID NO 17
<211> LENGTH: 58
<212> TYPE: PRT
<213> ORGANISM: Homo sapiens

<400> SEQUENCE: 17

Leu Pro Asn Val Cys Ala Phe Pro Met Glu Lys Gly Pro Cys Gln Thr
1               5                   10                  15

Tyr Met Thr Arg Trp Phe Phe Asn Phe Glu Thr Gly Glu Cys Glu Leu
            20                  25                  30

Phe Ala Tyr Gly Gly Cys Gly Gly Asn Ser Asn Asn Phe Leu Arg Lys
        35                  40                  45

Glu Lys Cys Glu Lys Phe Cys Lys Phe Thr
    50                  55

<210> SEQ ID NO 18
<211> LENGTH: 58
<212> TYPE: PRT
<213> ORGANISM: Homo sapiens

<400> SEQUENCE: 18

Met His Ser Phe Cys Ala Phe Lys Ala Asp Asp Gly Pro Cys Lys Ala
1               5                   10                  15

Ile Met Lys Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 19
<211> LENGTH: 58

```
<212> TYPE: PRT
<213> ORGANISM: Homo sapiens

<400> SEQUENCE: 19

Gly Pro Ser Trp Cys Leu Thr Pro Ala Asp Arg Gly Leu Cys Arg Ala
 1               5                  10                  15

Asn Glu Asn Arg Phe Tyr Tyr Asn Ser Val Ile Gly Lys Cys Arg Pro
             20                  25                  30

Phe Lys Tyr Ser Gly Cys Gly Gly Asn Glu Asn Asn Phe Thr Ser Lys
         35                  40                  45

Gln Glu Cys Leu Arg Ala Cys Lys Lys Gly
     50                  55

<210> SEQ ID NO 20
<211> LENGTH: 58
<212> TYPE: PRT
<213> ORGANISM: Homo sapiens

<400> SEQUENCE: 20

Glu Thr Asp Ile Cys Lys Leu Pro Lys Asp Glu Gly Thr Cys Arg Asp
 1               5                  10                  15

Phe Ile Leu Lys Trp Tyr Tyr Asp Pro Asn Thr Lys Ser Cys Ala Arg
             20                  25                  30

Phe Trp Tyr Gly Gly Cys Gly Gly Asn Glu Asn Lys Phe Gly Ser Gln
         35                  40                  45

Lys Glu Cys Glu Lys Val Cys Ala Pro Val
     50                  55

<210> SEQ ID NO 21
<211> LENGTH: 58
<212> TYPE: PRT
<213> ORGANISM: Homo sapiens

<400> SEQUENCE: 21

Lys Gln Asp Val Cys Glu Met Pro Lys Glu Thr Gly Pro Cys Leu Ala
 1               5                  10                  15

Tyr Phe Leu His Trp Trp Tyr Asp Lys Lys Asp Asn Thr Cys Ser Met
             20                  25                  30

Phe Val Tyr Gly Gly Cys Gln Gly Asn Asn Asn Phe Gln Ser Lys
         35                  40                  45

Ala Asn Cys Leu Asn Thr Cys Lys Asn Lys
     50                  55

<210> SEQ ID NO 22
<211> LENGTH: 267
<212> TYPE: PRT
<213> ORGANISM: Homo sapiens

<400> SEQUENCE: 22

Met Thr Leu Gly Arg Arg Leu Ala Cys Leu Phe Leu Ala Cys Val Leu
 1               5                  10                  15

Pro Ala Leu Leu Leu Gly Gly Thr Ala Leu Ala Ser Glu Ile Val Gly
             20                  25                  30

Gly Arg Arg Ala Arg Pro His Ala Trp Pro Phe Met Val Ser Leu Gln
         35                  40                  45

Leu Arg Gly Gly His Phe Cys Gly Ala Thr Leu Ile Ala Pro Asn Phe
     50                  55                  60

Val Met Ser Ala Ala His Cys Val Ala Asn Val Asn Val Arg Ala Val
65                  70                  75                  80
```

```
Arg Val Val Leu Gly Ala His Asn Leu Ser Arg Arg Glu Pro Thr Arg
                85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
        115                 120                 125

Ile Asn Ala Asn Val Gln Val Ala Gln Leu Pro Ala Gln Gly Arg Arg
    130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
    210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His
                260                 265

<210> SEQ ID NO 23
<211> LENGTH: 56
<212> TYPE: PRT
<213> ORGANISM: Artificial Sequence
<220> FEATURE:
<223> OTHER INFORMATION: Synthetically generated peptide

<400> SEQUENCE: 23

Glu Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 24
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 24

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
```

-continued

```
                50                  55                  60

<210> SEQ ID NO 25
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 25

Glu Ala Met His Ser Phe Cys Ala Phe Lys Ala Glu Thr Gly Pro Cys
  1               5                  10                  15

Arg Ala Arg Phe Asp Arg Trp Phe Phe Asn Ile Phe Thr Arg Gln Cys
                 20                  25                  30

Glu Glu Phe Ile Tyr Gly Gly Cys Glu Gly Asn Gln Asn Arg Phe Glu
             35                  40                  45

Ser Leu Glu Glu Cys Lys Lys Met Cys Thr Arg Asp
         50                  55                  60
```

POLY-PEGYLATED PROTEASE INHIBITORS

CROSS-REFERENCE TO RELATED APPLICATIONS

This application is a continuation of U.S. application Ser. No. 10/931,153, now abandoned, which was filed on Aug. 30, 2004, which claims the benefit of U.S. Provisional Application Ser. No. 60/498,845, filed on Aug. 29, 2003, and of U.S. Provisional Application Ser. No. 60/598,967, filed on Aug. 4, 2004.

BACKGROUND

The invention relates to modified protease inhibitors.

SUMMARY

In one aspect, the invention features a compound that include: a) a polypeptide including a Kunitz domain that specifically binds and/or inhibits a protease; and b) a plurality of non-protein moieties that are physically associated with the polypeptide and increases the molecular weight of the compound. The term "poly-PEGylated Kunitz domain" refers herein to the afore-mentioned compound. Typically, the non-protein moieties of a poly-PEGylated Kunitz domain include polyethylene glycol.

The compound (i.e., the polypeptide plus the plurality of non-protein moieties) has a molecular weight of greater than 12, 14 or 16 kDa. In one embodiment, each non-protein moiety has an average molecular weight of between 3 and 20, 3 and 12 kDa, 3 and 10 kDa, 3 and 8 kDa, 4 and 6 kDa, e.g., about 4, 5, 6, 7, or 8 kDa.

The protease that is bound and/or inhibited can be, for example, an elastase (e.g., human neutrophil elastase (hNE)), a plasmin, a kallikrein, or other protease, e.g., a protease described herein. For example, the protease can be a serine protease.

In one embodiment, non-protein moieties are attached to each available primary amine on the Kunitz domain, e.g., the N-terminal primary amine and any solvent-accessible primary amines, e.g., accessible primary amines of lysine side chains in the Kunitz domain. For example, all possible primary amines are conjugated to one of the non-protein moieties. The Kunitz domain may have at least one, two, three, or four lysines. For example, the Kunitz domain may have only one, two, three, four, or five lysines. In one embodiment, the polypeptide has an N-terminal primary amine. In another embodiment, the polypeptide does not include an N-terminal primary amine (e.g., the polypeptide can be chemically modified, e.g., with a non-polymeric compound, at its N-terminal primary amine so that the polypeptide does not include a primary amine at that position).

A non-protein moiety can be attached at 2 or more of the primary amines in the polypeptide. For example, all lysines or all lysines that have a solvent accessible primary amine are attached to a non-protein moiety. Preferably, the Kunitz domain does not include a lysine within one of its binding loops, e.g., about residues corresponding to amino acids 11-21 of BPTI and 31-42 of BPTI. Lysines within such binding loops can be replaced, e.g., with arginine residues. For example, the polypeptide is attached to at least three of molecules of the polymer. Each lysine of the polypeptide, or one, two, three or more of the lysines can be attached to a molecule of the polymer. Unless otherwise stated, when it is said that a primary amine, e.g., that of a particular lysine or at the N terminus, is modified or has a non-protein moiety attached thereto, it is understood that the specified primary amine position on every molecule in a preparation may not be so modified. The preparations need not be perfectly homogeneous to be within the invention. Homogeneity is desirable in some embodiments but it need not be absolute. In preferred embodiments, at least 60, 70, 80, 90, 95, 97, 98, 99, or 100% of a primary amine which is designated as modified will have a non-protein moiety attached thereto. Other embodiments however, include preparations that contains a mixture of species in which most of the molecules, e.g., at least 60, 70, 80, 90, 95, 97, 98, 99, or 100% are PEGylated at two or more sites but the sites (and in some cases the number of sites modified) on molecules in the preparation will vary. E.g., some molecules will have lysines A, B, and D modified while other molecules will have the amino terminus and lysines A, B, C, and D modified.

In one embodiment, the non-protein moiety includes a hydrophilic polymer, e.g., a substantially homogeneous polymer. The polymer can be branched or unbranched. For example, the moiety of polymer has a molecular weight (e.g., an average molecular weight of the moieties added to the compound) that is less than 20, 18, 15, 12, 10, 8, 7, or 6 or at least 1.5, 2, 2.5, 3, 5, 6, 10 kDa, e.g., about 5 kDa. In one embodiment, the sum of the molecular weight of the PEG moieties on the compound is at least 15, 20, 25, 30, or 35, and/or less than 60, 50, 40, 35, 30, 25, or 23 kDa.

In one embodiment, the polymer is a polyalkylene oxide. For example, at least 20, 30, 50, 70, 80, 90, or 95% of the copolymer blocks of the polymer are ethylene glycol. In one embodiment, the polymer is polyethylene glycol.

In one embodiment, the compound has the following structure:

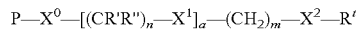

wherein P is the polypeptide,
each of R' and R" is, independently, H, or $C_1$-$C_{12}$ alkyl;
$X^0$ is O, N—$R^1$, S, or absent, wherein $R^1$ is H, $C_1$-$C_{12}$ alkyl or aryl,
$X^1$ is O, N—$R^2$, S, wherein $R^2$ is H, alkyl or aryl,
$X^2$ is O, N—$R^3$, S, or absent, wherein $R^3$ is H, alkyl or aryl,
each n is between 1 and 5, e.g., 2,
a is at least 4,
m is between 0 and 5, and
$R^t$ is H, $C_1$-$C_{12}$ alkyl or aryl.
R' and R" can be H. In one embodiment, R' or R" is independently, H, or C1-C4, C1-C6, or C1-C10 alkyl.

In one embodiment, the compound has the following structure:

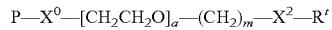

wherein P is the polypeptide,
a is at least 4,
m is between 0 and 5,
$X^2$ is O, N—$R^1$, S, or absent, wherein $R^1$ is H, alkyl or aryl,
$X^0$ is O, N—$R^2$, S, or absent, wherein $R^2$ is H, alkyl or aryl,
and
$R^t$ is H, $C_1$-$C_{12}$ alkyl or aryl. For example, $X^2$ is O, and $R^t$ is $CH_3$. (The use of mPEG is preferred.)

In one embodiment, the Kunitz domain polypeptide is less than 14, 8, or 7 kDa in molecular weight. In one embodiment, the Kunitz domain polypeptide includes only one Kunitz domain. Generally, the compound includes only one Kunitz domain, but in some embodiments, may include more than one.

In one embodiment, the Kunitz domain includes the amino acid sequence of DX-890, DX-88, or DX-1000 or an amino acid sequence that differs by at least one, but fewer than six, five, four, three, or two amino acid differences (e.g., substitutions, insertions, or deletions) from the amino acid sequence of DX-890, DX-88, or DX-1000. Typically, the Kunitz domain does not naturally occur in humans. The Kunitz domain may include an amino acid sequence that differs by fewer than ten, seven, or four amino acids from a human Kunitz domain.

In one embodiment, the $K_i$ of the compound is within a factor of 0.5 to 1.5, 0.8 to 1.2, 0.3 to 3.0, 0.1 to 10.0, or 0.02 to 50.0 of the $K_i$ of the unmodified polypeptide for elastase. For example, the $K_i$ for hNE can be less than 100, 50, 18, 12, 10, or 9 pM.

In one embodiment, the compound has a circulatory half life of the longest-lived component ("longest phase circulatory half life") in a rabbit or mouse model that is at least 1.5, 2, 4, or 8 fold greater than a substantially identical compound that does not include the polymer. The compound can have a longest phase circulatory half life in a rabbit or mouse model that has an amplitude at least 1.5, 2, 2.5, or 4 fold greater than a substantially identical compound that does not include the non-protein moiety. The compound can have an alpha-phase circulatory half life in a rabbit or mouse model that has an amplitude at least 20, 30, 40, or 50% smaller than a substantially identical compound that does not include the non-protein moiety. For example, the compound has a longest phase circulatory half life with an amplitude of at least 40, 45, 46, 50, 53, 54, 60, or 65%. In one embodiment, the compound has a beta phase circulatory half life in a mouse or rabbit model of at least 2, 3, 4, 5, 6, or 7 hours. In one embodiment, the compound has a longest phase circulatory half life in a 70 kg human of at least 6 hours, 12 hours, 24 hours, 2 days, 5 days, 7 days, or 10 days.

In one embodiment, the compound has a longest phase circulatory half life in a rabbit model of at least 4200 minutes, 4700 minutes, or 4980 minutes (or about 83 hours). In one embodiment, the compound has a longest phase circulatory half-life that is longer than a similarly sized molecule with the same Kunitz domain, but only a single PEG moiety (i.e., a mono-PEGylated version of the same Kunitz domain). The longest phase half-life can be at least 5, 10, 20, 30, or 50% longer. In one embodiment, in a mouse, the longest phase circulatory half life has an amplitude of greater than 50, 55, 60, or 65%. The longest phase half life can be, e.g., greater than 550, 600, 700, 750, 900, 1000, 1100 minutes.

In one embodiment, the compound has increased solubility (e.g., 1.5, 2, 4, or 8 fold greater) in an aqueous solution having a pH between 5 and 8 and an ionic strength less than the ionic strength of 0.5 M NaCl than the polypeptide that does not include the non-protein moiety.

In one embodiment, the polyethylene glycol is attached by coupling monomethoxy-PEG propionaldehyde or monomethoxy-PEG succinimidyl propionic acid to the polypeptide. The compound can formed by coupling of mPEG ($CH_3$—(O—$CH_2$—$CH_2$)$_n$—) at a pH that enables attachment to accessible amino groups on lysine side chains and to the N-terminal amino group, e.g., a pH 6.8 to 8.8, e.g., between 7.4 and 8.8.

In another aspect, the invention features a compound that includes (1) a polypeptide including the amino acid sequence of DX-890, DX-88, or DX-1000 or an amino acid sequence that differs by at least one, but fewer than six, five, four, three, or two amino acid differences (e.g., substitutions, insertions, or deletions) from the amino acid sequence of DX-890, DX-88, or DX-1000, and (2) a plurality of polyethylene glycol moieties. Each polyethylene glycol moiety can be less than 20, 19, 18, 15, 12, 11, 10, 9, 8, 7, or 6 kDa in molecular weight and is attached. Each polyethylene moiety can be attached to the polypeptide by a single covalent bond.

In one embodiment, a molecule of polyethylene glycol is attached to each lysine side chain of the polypeptide, e.g., where the polypeptide includes more than one lysine, e.g., two, three or four lysines. For example, the polypeptide is identical to the amino acid sequence of DX-890 and a molecule of polyethylene glycol is attached to each of the four lysine side chains of DX-890, and optionally also to the N-terminus. In another example, the polypeptide is identical to the amino acid sequence of DX-88 or DX-1000 and a molecule of polyethylene glycol is attached to each of the three lysine side chains of DX-88 or DX-1000, and, optionally, also to the N-terminus. In one embodiment, the molecules of polyethylene glycol are between 4 and 12 kDa in molecular weight. In one embodiment, the polyethylene glycol is attached to the N-terminus and to each accessible lysine side chain.

In one embodiment, the amino acid sequence differs by at least one amino acid from the amino acid sequence of DX-890. The amino acid sequence is identical to the amino acid sequence of DX-890 at one or more positions (e.g., at least two, three, five, seven, ten, twelve, thirteen, fourteen, or all) corresponding to positions 5, 13, 14, 16, 17, 18, 19, 30, 31, 32, 34, 38, 39, 51, and 55 according to the BPTI numbering.

In another aspect, the invention features a preparation that comprises Kunitz domain polypeptides that specifically bind and inhibit a protease. At least 40, 50, 70, 80, 85, 90, 92, 95, 97, 98, 99, or 99.5% of the Kunitz domain polypeptides in the preparation (i) bind and inhibit the protease, and (ii) have a polyethylene glycol moiety attached at a first common site and a polyethylene glycol moiety attached at a second common site. Typically, the average molecular weight of each attached polyethylene glycol moiety is less than 12, 10, or 8 kDa. In one embodiment, the designated population of Kunitz domain polypeptides further have a polyethylene glycol moiety attached at the third common site and a polyethylene glycol moiety attached at the fourth common site. For example, the designated population of Kunitz domain polypeptides have a polyethylene glycol moiety attached to each accessible primary amine and/or an N-terminal primary amine.

In one embodiment, each of the Kunitz domain polypeptides in the preparation binds and inhibits the protease. For example, Kunitz domain polypeptides that are not members of the designated population also bind and inhibit a protease, e.g., the same or a different protease.

The Kunitz domain polypeptides of the population can include, for example, other features described herein.

The invention also features a preparation that includes a compound described herein, e.g., above. For example, the compound is present at a concentration of at least 0.1, 1, 2, or 5 mg of polypeptide per milliliter, e.g., in a solution between pH 6-8. In one embodiment, the compound produces a major peak by size exclusion chromatography that includes at least 70% the compound relative to the injectate. In one embodiment, the molecular weight of 95% of the species of the compound are within 5, 4, 3, 2, or 1 kDa of the average molecular weight of the compound.

In another aspect, the invention features a pharmaceutical preparation that includes (1) a compound described herein, and (2) a pharmaceutically acceptable carrier. In one embodiment, at least 60, 70, 80, 85, 90, 95, 97, 98, 99, or 100% of the compounds in the preparation have an identical distribution of PEG molecules attached thereto. The use of chemical reaction in which all available primary amines (e.g., all solvent accessible primary amines, or all primary amines) are modified can be used to provide a preparation in which the compounds have an identical distribution of PEG molecules. Of course, some variation will be present in the molecule weight of the moieties attached to different primary amines on a given molecule or among molecules since there is variation about an average molecular weight for the PEG reagent used in the chemical reaction. The preparation can also be made using a process that provides a greater than 25, 30, 40, 50, 60, 70, 75, 80, or 85% yield for input protein.

In one embodiment, the preparation is aqueous and the compound is present at a concentration of at least 0.1 mg of polypeptide per milliliter. In one embodiment, injection of the preparation into a mouse results in less than 50, 30, 25, 15, or 10% of the compound is an SEC peak with higher mobility than the preparation after 12 hours.

The preparation can be suitable for pulmonary delivery or for gastrointestinal delivery (e.g., ingestion, rectal, etc.).

In another aspect, the invention features a pharmaceutical preparation that includes (1) a compound described herein, and (2) a pharmaceutically acceptable carrier. In one embodiment, at least 60, 70, 80, 85, 90, 95, 97, 98, 99, or 100% of the polypeptides in the preparation have at least 2, 3 or 4 primary amines modified with a non-protein moiety. The preparation can contain a mixture of species in which most of the molecules, e.g., at least 60, 70, 80, 90, or 95% are PEGylated at least 2 (or 3 or 4) sites but the sites (and in some cases the number of sites modified) on molecules in the preparation will vary. E.g., some molecules will have lysines A, B, and D modified while other molecules will have the amino terminus and lysines A, B, C, and D modified. In some embodiments, the preparation can include a small number of compounds that are inactive (e.g., less than 5, 2, 1, or 0.1%), but generally, most of the compounds (e.g., at least 50%, 90, 95, 98, 99, 99.5, or 99.9%) in the preparation are active, e.g., can inhibit a protease.

In some aspects of the invention, the non-protein moiety attached to different sites will be the same, in terms of identity or size. In other aspects, a first non-protein moiety is attached at a first primary amine, and a second non-protein moiety which is different, e.g., by type or size, is attached to a different primary amine. E.g., it may be desirable to attach a PEG of a first size to the primary amine of the N terminus but to attach a PEG of a different size to a lysine position.

The invention also features a medical device that includes a dispenser and a compartment that includes a pharmaceutical preparation described herein. For example, the dispenser is configured to generate an inhalable form of the pharmaceutical preparation. The invention also features an implantable medical device that includes a dispenser and a compartment that includes a pharmaceutical preparation described herein wherein the dispenser is configured to delivery the pharmaceutical preparation into the circulatory system of a subject. The invention also features a suppository that includes a pharmaceutical preparation described herein.

In another aspect, the invention features a preparation that includes a poly-pegylated Kunitz domain. The preparation can be substantially (e.g., at least 70, 75, 80, 85, 90, 95, or 100%) monodisperse. For example, the poly-PEGylated compound is present at a concentration of at least 0.05, 0.1, 0.2, 0.5, 0.8, 1.0, 1.5, 2.0, or 2.5 milligrams of polypeptide per milliliter or between 0.05 and 10 milligrams of polypeptide per milliliter. In one embodiment, the preparation is dry. For example, the preparation includes particles or is in the form of a powder.

In another aspect, the invention features a compound that includes a polypeptide including the amino acid sequence of DX-890, DX-88, or DX-1000 or other Kunitz domain sequence described herein in which at least one lysine is substituted with a non-lysine amino acid, e.g., arginine. The compound is useful for reducing the number of lysines to which PEG is coupled, e.g., without a substantial change in activity, to produce a substantially homogenous conjugate. In one embodiment, the amino acid sequence (e.g., of DX-890) has three lysine substitutions and a single remaining lysine. In another embodiment, the amino acid has one or two lysine substitutions. In one embodiment, the compound further includes a non-protein moiety, e.g., a hydrophilic polymer described herein. The polymer can be coupled to the remaining lysine residues, e.g., single remaining lysine (e.g., the first, second, third, or fourth lysine).

In another aspect, the invention features a preparation (e.g., an aqueous preparation) that includes: a compound that includes a Kunitz domain conjugated to a plurality of moieties of a hydrophilic and substantially homogeneous polymer. For example, the concentration of Kunitz domain component alone is greater than 2 mg per ml, the pH of the preparation is greater than 3, and the ionic strength of the preparation is less than the ionic strength of 0.5 M NaCl. In one embodiment, the Kunitz domain includes the amino acid sequence of DX-890, DX-88, or DX-1000 or an amino acid sequence that differs by at least one, but fewer than six, five, four, three, or two amino acid differences (e.g., substitutions, insertions, or deletions) from the amino acid sequence of DX-890. The invention also provides a sealed container that includes the preparation. The container can be opaque to light. The container can include printed information on an external region of the container.

In another aspect, the invention features a method that includes: providing a polypeptide that includes a Kunitz domain; contacting the polypeptide to a hydrophilic polymer (e.g., a polyalkylene oxide) that includes a single reactive group that can form a covalent bond with the polypeptide under conditions suitable for bond formation at a plurality of available sites (e.g., a plurality of primary amines, e.g., all available primary amines), thereby providing a modified protease inhibitor.

In one embodiment, the hydrophilic polymer is monoactivated. For example, the hydrophilic polymer is alkoxy-terminated. In one embodiment, the polymer includes a succinimidyl group.

In one embodiment, the polymer is a polyethylene glycol, e.g., monomethoxy-polyethylene glycol. For example, the polymer is mPEG propionaldehyde or mPEG succinimidyl propionic acid.

In one embodiment, the conditions are between pH 6.5 and 9.0, e.g., between 7.5 and 8.5. In one embodiment, the hydrophilic polymer is covalently attached to the N-terminus of the polypeptide. In another embodiment, the hydrophilic polymer is covalently attached to a lysine side chain of the polypeptide.

The method can further include separating polypeptides that have a single attached polymer from other products and reactants. The method can further include chromatographically separating products of the contacting, e.g., using ion exchange chromatography or size exclusion chromatography.

The invention also features a modified Kunitz domain prepared by a method described herein, e.g., the above method.

In another aspect, the invention features a method of treating a disorder characterized by excessive or undesired activity of a protease. The method includes: administering to a subject having the disorder or suspected of having the disorder to pharmaceutical composition comprising a compound or preparation described herein. The compound or preparation includes a Kunitz domain polypeptide that inhibits the protease. For example, a preparation has at least a certain percentage of molecules of the Kunitz domain polypeptide in which a hydrophilic polymer is attached to a first common site and a second common site. For example, at least a certain percentage of molecules of the Kunitz domain polypeptide further include the hydrophilic polymer attached to a third, fourth, and optionally a fifth common site.

In one embodiment, the protease is elastase. For example, the Kunitz domain polypeptide comprises the amino acid sequence of DX-890 or a sequence that differs by at least one, but fewer than six amino acid alterations from DX-890. Exemplary disorders that can be treated using a Kunitz domain that inhibits elastase (e.g., human neutrophil elastase) include cystic fibrosis, COPD, and an inflammatory disorder.

In one embodiment, the protease is a kallikrein. For example, the Kunitz domain polypeptide comprises the amino acid sequence of DX-88 or a sequence that differs by at least one, but fewer than six amino acid alterations from DX-88. Exemplary disorders that can be treated using a Kunitz domain that inhibits a kallikrein include disorders of coagulation, fibrinolysis, hypotensions, inflammation, hemophilia, post-operative bleeding, peri-operative bleeding, and hereditary angioedema.

In one embodiment, the protease is plasmin and the Kunitz domain polypeptide comprises the amino acid sequence of DX-1000 or a sequence that differs by at least one, but fewer than six amino acid alterations from DX-1000. Exemplary disorders that can be treated using a Kunitz domain that inhibits plasmin include fibrinolysis or fibrinogenolysis, excessive bleeding associated with thrombolytics, post-operative bleeding, peri-operative bleeding, and inappropriate androgenesis.

In another aspect, the invention features a method of treating or preventing a pulmonary disorder. The method includes administering a compound described herein to a subject, e.g., in an amount effective to ameliorate at least one symptom of the disorder. For example, the compound includes a) a polypeptide including a Kunitz domain that specifically binds and inhibits an elastase (e.g., human neutrophil elastase (hNE)); and b) a non-protein moiety that is physically associated with the polypeptide and increases the molecular weight of the compound. For example, the compound includes (1) a polypeptide including the amino acid sequence of DX-890 or an amino acid sequence that differs by at least one, but fewer than six, five, four, three, or two amino acid differences (e.g., substitutions, insertions, or deletions) from the amino acid sequence of DX-890, and (2) polyethylene glycol wherein the sum of the polyethylene glycol moieties is at least 15, 18, 20, 25, 27, or 30 kDa in molecular weight.

In one embodiment, the compound is administered no more than once every 12, 24, 36, or 72 hours. In another embodiment, the compound is administered no more than once every four, seven, ten, twelve, or fourteen days. The compound can be administered once or at multiple times (e.g., regularly).

In one embodiment, the administering includes pulmonary delivery. For example, the administering includes actuation of an inhaler and/or nebulization. In one embodiment, the administering includes delivery of the composition directly or indirectly into the circulatory system. For example, the administering includes injection or intravenous delivery.

In one embodiment, the subject has cystic fibrosis or a genetic defect in the cystic fibrosis gene. In another embodiment, the subject has chronic obstructive pulmonary disease.

The symptom can be lung tissue integrity or an index of tissue destruction.

In another aspect, the invention features a method of treating or preventing a inflammatory disorder. The method includes: administering a compound described herein to a subject, e.g., in an amount effective to ameliorate at least one symptom of the disorder. For example, the compound includes a) a polypeptide including a Kunitz domain that specifically binds and inhibits an elastase (e.g., human neutrophil elastase (hNE)); and b) a plurality of non-protein moieties that are physically associated with the polypeptide and increase the molecular weight of the compound. For example, the compound includes (1) a polypeptide including the amino acid sequence of DX-890 or an amino acid sequence that differs by at least one, but fewer than six, five, four, three, or two amino acid differences (e.g., substitutions, insertions, or deletions) from the amino acid sequence of DX-890, and (2) a plurality of polyethylene glycol moieties, e.g., wherein each polyethylene glycol moiety is less than 20, 18, 16, 12, 10, 9, 8, or 7 kDa in molecular weight.

In one embodiment, the disorder is an inflammatory bowel disorder, e.g., Crohn's disease or ulcerative colitis. In one embodiment, the compound is delivered by a suppository.

In one embodiment, the compound is administered no more than once every 12, 24, 36, or 72 hours. In another embodiment, the compound is administered no more than once every four, seven, ten, twelve, or fourteen days. The compound can be administered once or at multiple times (e.g., regularly).

In another aspect, the invention features a method of treating or preventing a disorder characterized at least in part by inappropriate elastase activity or neutrophil activity. The method includes administering a compound described herien to a subject, e.g., in an amount effective to ameliorate at least one symptom of the disorder or to alter elastase or neutrophil activity, e.g., to reduce elastase-mediated proteolysis. For example, the disorder is rheumatoid arthritis.

In one embodiment, the compound is administered no more than once every 12, 24, 36, or 72 hours. In another embodiment, the compound is administered no more than once every four, seven, ten, twelve, or fourteen days. The compound can be administered once or at multiple times (e.g., regularly).

Many of the examples provided herein describe methods and compositions that relate to Kunitz domains and a particular protease target—elastase. However, these methods and compositions can be modified to provide corresponding methods and compositions that relate to other targets, e.g., other proteases or other proteins, e.g., protease other than Kunitz domains, particularly proteins that include one or more lysine residues. For example, the lysines may be positioned at a site where their modification does not interfere with function. Similarly the described methods and compositions can be modified to corresponding methods and compositions that relate to polypeptides that do not include a Kunitz domain or that include a Kunitz domain and other types of domains.

As used herein, "binding affinity" refers to the apparent association constant or Ka. The Ka is the reciprocal of the dissociation constant (Kd). A ligand may, for example, have a binding affinity of at least $10^5, 10^6, 10^7, 10^8, 10^9, 10^{10}, 10^{11}$, or $10^{12}$ $M^{-1}$ for a particular target molecule. Higher affinity binding of a ligand to a first target relative to a second target can be indicated by a higher Ka (or a smaller numerical value Kd) for binding the first target than the Ka (or numerical value Kd) for binding the second target. In such cases the ligand has specificity for the first target relative to the second target. Ka measurements for binding to hNE are typically made under the following conditions: 50 mM HEPES, pH 7.5, 150 mM NaCl, and 0.1% Triton X-100 at 30° C. using 100 pM of the hNE.

Binding affinity can be determined by a variety of methods including equilibrium dialysis, equilibrium binding, gel filtration, ELISA, surface plasmon resonance, or spectroscopy (e.g., using a fluorescence assay). These techniques can be used to measure the concentration of bound and free ligand as a function of ligand (or target) concentration. The concentration of bound ligand ([Bound]) is related to the concentration of free ligand ([Free]) and the concentration of binding sites for the ligand on the target where (N) is the number of binding sites per target molecule by the following equation:

$$[Bound] = N \cdot [Free]/((1/K_a) + [Free])$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2 fold higher.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 95, 98, or 99% pure on a weight-weight basis.

An "epitope" refers to the site on a target compound that is bound by a ligand, e.g., a polypeptide ligand such as a Kunitz domain, small peptide, or antibody. In the case where the target compound is a protein, for example, an epitope may refer to the amino acids that are bound by the ligand. Such amino acids may be contiguous or non-contiguous with respect to the underlying polypeptide backbone. Overlapping epitopes include at least one common amino acid residue.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of Kunitz domains, the second domain has the same specificity and, for example, has at least 0.5, 5, or 50% of the binding affinity of the first domain. A sufficient degree of identity may be about 85%, 90%, 91%, 92%, 93%, 94%, 95%, 96%, 97%, 98%, 99% or higher.

Sequences similar or homologous (e.g., at least about 85% sequence identity) to the sequences disclosed herein are also part of this application. In some embodiment, the sequence identity can be about 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

As used herein, the term "homologous" is synonymous with "similarity" and means that a sequence of interest differs from a reference sequence by the presence of one or more amino acid substitutions (although modest amino acid insertions or deletions) may also be present. Presently preferred means of calculating degrees of homology or similarity to a reference sequence are through the use of BLAST algorithms (available from the National Center of Biotechnology Information (NCBI), National Institutes of Health, Bethesda Md.), in each case, using the algorithm default or recommended parameters for determining significance of calculated sequence relatedness. The percent identity between two amino acid or nucleotide sequences can also be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. Accordingly, nucleic acids that hybridize with appropriate stringency to nucleic acids that encode a polypeptide described herein are provided as are polypeptides that are encode by such nucleic acids. Such polypeptides can be similarly modified as described herein.

It is understood that a polypeptide described herein (e.g., a polypeptide that includes a Kunitz domain) may have mutations relative to a particular polypeptide described herein (e.g., a conservative or non-essential amino acid substitutions), which do not have a substantial effect on the polypeptide functions. Whether or not a particular substitution will be tolerated, i.e., will not adversely affect desired biological properties, such as binding activity can be determined as described in Bowie, et al. (1990) *Science* 247:1306-1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

The terms "polypeptide" or "peptide" (which may be used interchangeably) refer to a polymer of three or more amino acids linked by a peptide bond, e.g., between 3 and 30, 12 and 60, or 30 and 300, or over 300 amino acids in length. The polypeptide may include one or more unnatural amino acids. Typically, the polypeptide includes only natural amino acids. A "protein" can include one or more polypeptide chains. Accordingly, the term "protein" encompasses polypeptides. A protein or polypeptide can also include one or more modifications, e.g., a glycosylation, amidation, phosphorylation, and so forth. The term "small peptide" can be used to describe a polypeptide that is between 3 and 30 amino acids in length, e.g., between 8 and 24 amino acids in length.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it.

The term "aryl" refers to an aromatic monocyclic, bicyclic, or tricyclic hydrocarbon ring system, wherein any ring atom capable of substitution can be substituted by a substituent. Examples of aryl moieties include, but are not limited to, phenyl, naphthyl, and anthracenyl.

The details of one or more embodiments of the invention are set forth in the accompanying drawings and the description below. Other features, objects, and advantages of the invention will be apparent from the description and drawings, and from the claims. All published patent applications, patents, and references cited herein are incorporated by reference in their entirety. In particular, U.S. Pat. Nos. 5,663,143; 5,223,409, 6,010,080, 6,103,499 and 6,333,402 are incorporated by reference in their entireties.

BRIEF DESCRIPTION OF THE DRAWINGS

FIG. 9 shows exemplary results of DX-88 poly-PEGylation at various rations by SDS-PAGE analysis.

DETAILED DESCRIPTION

Figure 1:
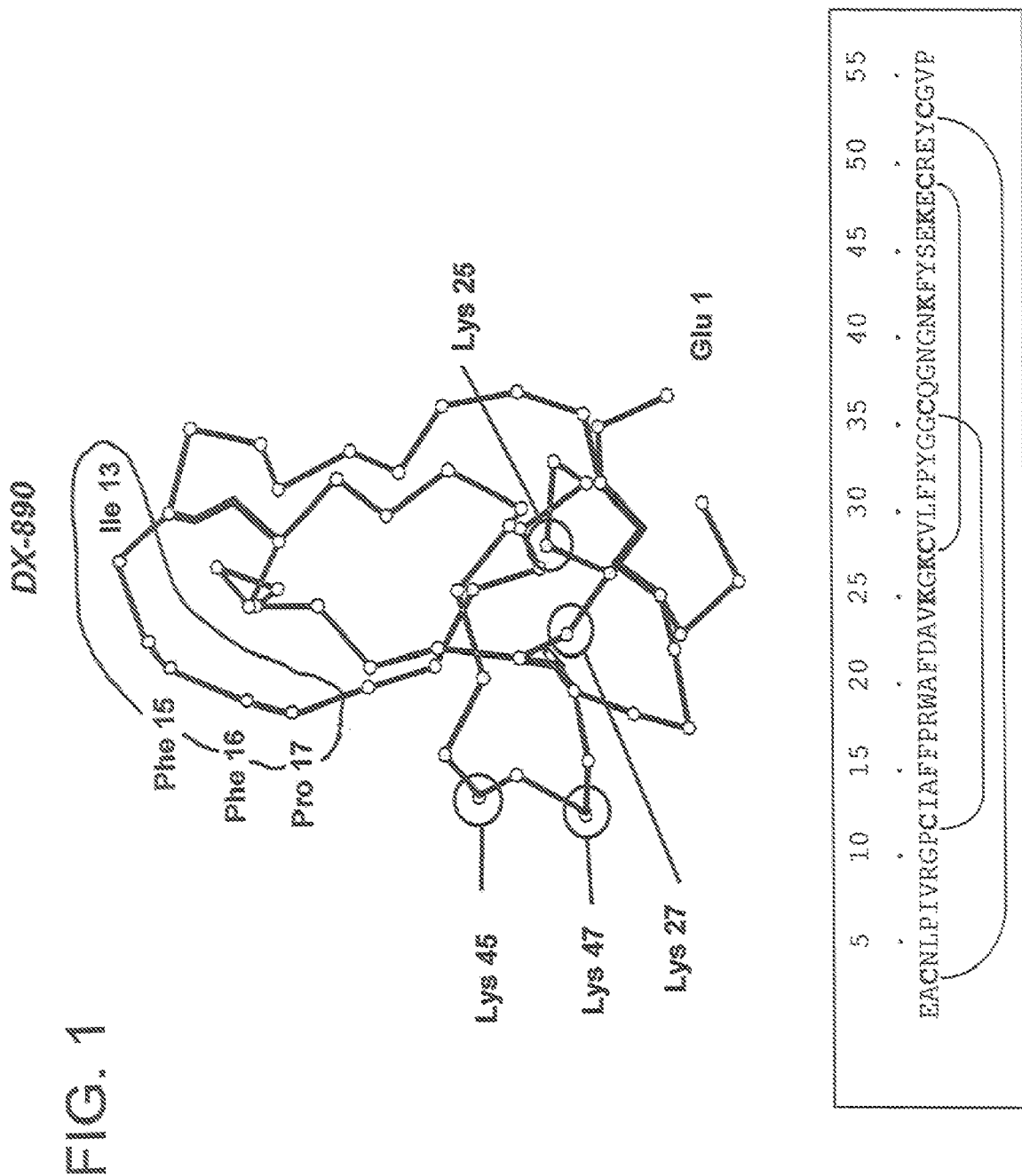
FIG. 1 depicts the structure of DX-890 (SEQ ID NO:23) and the position of its four lysine residues.

The invention provides, in part, compounds that bind to and inhibit a protease (e.g., an elastase, e.g., a neutrophil elastase). The compounds include (i) a polypeptide that includes a Kunitz domain and (ii) a plurality of moieties (such as polymer moieties) that increases the molecular weight of the compounds relative to the polypeptide alone. The addition of the moieties to the compound can increase the in vivo circulating half life of the compound. In some embodiments, the compounds can inhibit neutrophil elastase with high affinity and selectivity.

Polymers

A variety of moieties can be used to increase the molecular weight of a polypeptide that includes a Kunitz domain or other protease inhibitor. In one embodiment, the moiety is a polymer, e.g., a water soluble and/or substantially non-antigenic polymer such as a homopolymer or a non-biological polymer. Substantially non-antigenic polymers include, e.g., polyalkylene oxides or polyethylene oxides. The moiety may improve stabilization and/or retention of the Kunitz domain in circulation, e.g., in blood, serum, lymph, or other tissues, e.g., by at least 1.5, 2, 5, 10, 50, 75, or 100 fold. A plurality of moieties are attached to a Kunitz domain. For example, the polypeptide is attached to at least three moieties of the polymer. Each lysine of the polypeptide can be attached to a moiety of the polymer.

Suitable polymers can vary substantially by weight. For example, it is possible to use polymers having average molecular weights ranging from about 200 Daltons to about 40 kDa, e.g., 1-20 kDa, 4-12 kDa or 3-8 kDa, e.g., about 4, 5, 6, or 7 kDa. In one embodiment, the average molecular weight of individual moieties of the polymer that are associated with the compound are less than 20, 18, 17, 15, 12, 10, 8, or 7 kDa. The final molecular weight can also depend upon the desired effective size of the conjugate, the nature (e.g. structure, such as linear or branched) of the polymer, and the degree of derivatization.

A non-limiting list of exemplary polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. The polymer can be a hydrophilic polyvinyl polymers, e.g. polyvinylalcohol and polyvinylpyrrolidone. Additional useful polymers include polyoxyalkylenes such as polyoxyethylene, polyoxypropylene, and block copolymers of polyoxyethylene and polyoxypropylene (Pluronics); polylactic acid; polyglycolic acid; polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, cellulose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. In some embodiments, the polymer includes a variety of different copolymer blocks.

The polypeptide that includes a Kunitz domain can be physically associated with the polymer in a variety of ways. Typically, the polypeptide is covalently linked to the polymer at a plurality of sites. For example, the polypeptide is conjugated to the polymer at a plurality of primary amines, e.g., all accessible primary amines or all primary amines. Other compounds can also be attached to the same polymer, e.g., a cytotoxin, a label, or another targeting agent, e.g., another ligand that binds to the same target as the Kunitz domain or a ligand that binds to another target, e.g., a an unrelated ligand. Other compounds may also be attached to the polypeptide.

In one embodiment, the polymer is water soluble prior to conjugation to the polypeptide (although need not be). Generally, after conjugation to the polypeptide, the product is water soluble, e.g., exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid conjugation of one polymer to multiple protein molecules. Mono-activated, alkoxy-terminated polyalkylene oxides (PAO's), e.g., monomethoxy-terminated polyethylene glycols (mPEG's); $C_{1-4}$ alkyl-terminated polymers; and bis-activated polyethylene oxides (glycols) can be used for conjugation to the polypeptide. See, e.g., U.S. Pat. No. 5,951,974.

In its most common form, poly(ethylene glycol), PEG, is a linear or branched polyether terminated with hydroxyl groups. Linear PEG can have the following general structure:

$$HO-(CH_2CH_2O)_n-CH_2CH_2-OH$$

PEG can be synthesized by anionic ring opening polymerization of ethylene oxide initiated by nucleophilic attack of a hydroxide ion on the epoxide ring. Particularly useful for polypeptide modification is monomethoxy PEG, mPEG, having the general structure:

$$CH_3O-(CH_2CH_2O)_n-CH_2CH_2-OH$$

For further descriptions, see, e.g., Roberts et al. (2002) *Advanced Drug Delivery Reviews* 54:459-476. In one embodiment, the polymer units used for conjugation are mono-disperse or otherwise highly homogenous, e.g., present in a preparation in which 95% or all molecules are with 7, 5, 4, 3, 2, or 1 kDa of one another. In another embodiment, the polymer units are poly-disperse.

It is possible to select reaction conditions that reduce cross-linking between polymer units or conjugation to multiple polypeptides and to purify the reaction products through gel filtration or ion exchange chromatography to recover substantially homogenous derivatives, e.g., derivatives that include only a single Kunitz domain polypeptide. In other embodiments, the polymer contains two or more reactive groups for the purpose of linking multiple polypeptides (e.g., multiple units of the Kunitz domain polypeptide) to the polymer. Again, gel filtration or ion exchange chromatography can be used to recover the desired derivative in substantially homogeneous form.

The polypeptide that includes a Kunitz domain is generally attached to a plurality of PEG molecules. For example, to form a compound that is larger than 20 or 30 kDa, a Kunitz domain (about 7 kDa) can be attached to at least three 8 kDa molecules of PEG. Other combinations are possible, e.g., at least two, four, or five molecules of PEG. The molecular weight of the PEG molecules can be selected so that the final molecular weight of the compound is equal to or larger than a desired molecular weight (e.g., between 17-35, or 20-25, or 27-33 kDa). The plurality of PEG molecules can be attached to any region of the Kunitz domain, preferably at least 5, 10, or 15 Angstroms from a region that interacts with a target, or at least 2, 3, or 4 residues from an amino acid that interacts with a target. The PEG molecules can be attached, e.g., to lysine residues or a combination of lysine residues and the N-terminus.

A covalent bond can be used to attach a polypeptide (e.g., a polypeptide that includes a Kunitz domain) to a polymer, for example, conjugation to the N-terminal amino group and epsilon amino groups found on lysine residues, as well as other amino, imino, carboxyl, sulfhydryl, hydroxyl or other hydrophilic groups. The polymer may be covalently bonded directly to the polypeptide without the use of a multifunctional (ordinarily bifunctional) crosslinking agent. Covalent binding to amino groups can be accomplished by known chemistries based upon cyanuric chloride, carbonyl diimidazole, aldehyde reactive groups (PEG alkoxide plus diethyl acetyl of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylcloroformate activated PEG.) Carboxyl groups can be derivatized by coupling PEG-primary amine using carbodiimide. Sulfhydryl groups can be derivatized by coupling to maleimido-substituted PEG (see, e.g., WO 97/10847) or PEG-maleimide (e.g., commercially available from Shearwater Polymers, Inc., Huntsville, Ala.). Alternatively, free amino groups on the polypeptide (e.g. epsilon amino groups on lysine residues) can be thiolated with 2-imino-thiolane (Traut's reagent) and then coupled to maleimide-containing derivatives of PEG, e.g., as described in Pedley et al., Br. J. Cancer, 70: 1126-1130 (1994).

Functionalized PEG polymers that can be attached to a polypeptide that includes Kunitz domain include polymers that are commercially available, e.g., from Shearwater Polymers, Inc. (Huntsville, Ala.). Such PEG derivatives include, e.g., amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives may vary depending on the polypeptide, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc.

Kunitz Domains

As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI sequence provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3 or 2 amino acids of the following spacing between positions corresponding to: 5 to 55, 14 to 38, and 30 to 51, according to the numbering of the BPTI sequence provided below. The BPTI sequence can be used a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., (1990) Protein Engineering, 3(7):591-598; Hynes et al., (1990) Biochemistry, 29:10018-10022) are known. At least seventy Kunitz domain sequences are known. Known human homologues include three Kunitz domains of LACI (Wun et al., (1988) J. Biol. Chem. 263(13):6001-6004; Girard et al., (1989) Nature, 338:518-20; Novotny et al, (1989) J. Biol. Chem., 264(31): 18832-18837) two Kunitz domains of Inter-α-Trypsin Inhibitor, APP-I (Kido et al., (1988) J. Biol. Chem., 263(34):18104-18107), a Kunitz domain from collagen, and three Kunitz domains of TFPI-2 (Sprecher et al., (1994) PNAS USA, 91:3353-3357). LACI is a human serum phosphoglycoprotein with a molecular weight of 39 kDa (amino acid sequence in Table 1) containing three Kunitz domains.

TABLE 1

Exemplary Natural Kunitz Domains

```
LACI:         1  MIYTMKKVHA LWASVCLLLN LAPAPLNAds eedeehtiit dtelpplklM
(SEQ ID      51  HSFCAFKADD GPCKAIMKRF FFNIFTRQCE EFIYGGCEGN QNRFESLEEC
NO.1)       101  KKMCTRDnan riikttlqqe kpdfCfleed pgiCrgyitr yfynnqtkqC
            151  erfkyqqClg nmnnfetlee CkniCedgpn gfqvdnygtq lnavnnsltp
            201  qstkvpslfe fhgpswCltp adrglCrane nrfyynsvig kCrpfkysgC
            251  ggnennftsk qeClraCkkg fiqriskggl iktkrkrkkq rvkiayeeif
            301  vknm
The signal sequence (1-28) is uppercase and underscored
LACI-K1 is uppercase
LACI-K2 is underscored
LACI-K3 is bold BETI                  1          2          3          4          5
(SEQ ID       12345678901234567890123456789012345678901234567890123456 78
NO:2)         RPDFCLEPPYTGPCKARI IRYFYNAKAGLCQTFVYGGCRAKRNNFKSAEDCMRTCGGA
```

The conjugates of a polypeptide that includes a Kunitz domain and a polymer can be separated from the unreacted starting materials using chromatographic methods, e.g., by gel filtration or ion exchange chromatography, e.g., HPLC. Heterologous species of the conjugates are purified from one another in the same fashion. Resolution of different species (e.g. containing one or two PEG residues) is also possible due to the difference in the ionic properties of the unreacted amino acids. See, e.g., WO 96/34015.

The Kunitz domains above are referred to as LACI-K1 (residues 50 to 107), LACI-K2 (residues 121 to 178), and LACI-K3 (213 to 270). The cDNA sequence of LACI is reported in Wun et al. (J. Biol. Chem., 1988, 263(13):6001-6004). Girard et al. (Nature, 1989, 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

Proteins containing exemplary Kunitz domains include the following, with SWISS-PROT Accession Numbers in parentheses:

```
A4_HUMAN    (P05067), A4_MACFA    (P53601), A4_MACMU   (P29216),
A4_MOUSE    (P12023), A4_RAT      (P08592), A4_SAISC   (Q95241),
AMBP_PLEPL  (P36992), APP2_HUMAN  (Q06481), APP2_RAT   (P15943),
AXP1_ANTAF  (P81547), AXP2_ANTAF  (P81548), BPT1_BOVIN (P00974),
BPT2_BOVIN  (P04815), CA17_HUMAN  (Q02388), CA36_CHICK (P15989),
CA36_HUMAN  (P12111), CRPT_BOOMI  (P81162), ELAC_MACEU (O62845),
ELAC_TRIVU  (Q29143), EPPI_HUMAN  (O95925), EPPI_MOUSE (Q9DA01),
HTIB_MANSE  (P26227), IBP_CARCR   (P00993), IBEC_BOVIN (P00976),
IBPI_TACTR  (P16044), IBPS_BOVIN  (P00975), ICS3_BOMMO (P07481),
IMAP_DROFU  (P11424), IP52_ANESU  (P10280), ISC1_BOMMO (P10831),
ISC2_BOMMO  (P10832), ISH1_STOHE  (P31713), ISH2_STOHE (P81129),
ISIK_HELPO  (P00994), ISP2_GALME  (P81906), IVB1_BUNFA (P25660),
IVB1_BUNMU  (P00987), IVB1_VIPAA  (P00991), IVB2_BUNMU (P00989),
IVB2_DABRU  (P00990), IVB2_HEMHA  (P00985), IVB2_NAJNI (P00986),
IVB3_VIPAA  (P00992), IVBB_DENPO  (P00983), IVBC_NAJNA (P19859),
IVBC_OPHHA  (P82966), IVBE_DENPO  (P00984), IVBI_DENAN (P00980),
IVBI_DENPO  (P00979), IVBK_DENAN  (P00982), IVBK_DENPO (P00981),
IVBT_ERIMA  (P24541), IVBT_NAJNA  (P20229), MCPI_MELCP (P82968),
SBPI_SARBU  (P26228), SPT3_HUMAN  (P49223), TKD1_BOVIN (Q28201),
TKD1_SHEEP  (Q29428), TXCA_DENAN  (P81658), UPTI_PIG   (Q29100),
AMBP_BOVIN  (P00978), AMBP_HUMAN  (P02760), AMBP_MERUN (Q62577),
AMBP_MESAU  (Q60559), AMBP_MOUSE  (Q07456), AMBP_PIG   (P04366),
AMBP_RAT    (Q64240), IATR_HORSE  (P04365), IATR_SHEEP (P13371),
SPT1_HUMAN  (Q43278), SPT1_MOUSE  (Q9R097), SPT2_HUMAN (O43291),
SPT2_MOUSE  (Q9WU03), TFP2_HUMAN  (P48307), TFP2_MOUSE (O35536),
TFPI_HUMAN  (P10646), TFPI_MACMU  (Q28864), TFPI_MOUSE (O54819),
TFPI_RABIT  (P19761), TFPI_RAT    (Q02445), YN81_CAEEL (Q03610)
```

TABLE 2

The amino-acid sequences of 19 human Kunitz domains.
Amino-acid sequences of 19 Human Kunitz Domains Binding loops are underscored.

Collagen A1 VII (SEQ ID NO:3)
SDDPCSLPLDEGSCTAYTLRWYHRAVTEACHPFVYGGCGGNANRFGTREACERRCPPR TFPI2-K1 (SEQ ID NO:4)
NAEICLLPLDYGPCRALLLRYYYDRYTQSCRQFLYGGCEGNANNFYTWEACDDACWRI AppI (SEQ ID NO:5)
VREVCSEQAETGPCRAMISRWYFDVTEGKCAPFFYGGCGGNRNNFDTEEYCMAVCGSA Hep GF AI T2, K2 (SEQ ID NO:6)
YEEYCTANAVTGPCRASFPRWYFDVERNSCNNFIYGGCRGNKNSYRSEEACMLRCFRQ

ITI, K1 (SEQ ID NO:7)
KEDSCQLGYSAGPCMGMTSRYFYNGTSMACETFQYGGCMGNGNNFVTEKECLQTCRTV

Chrome20 (SEQ ID NO:8)
FQEPCMLPVRHGNCNHEAQRWHFDFKNYRCTPFKYRGCEGNANNFLNEDACRTACMLIR

TABLE 2-continued

The amino-acid sequences of 19 human Kunitz domains.
Amino-acid sequences of 19 Human Kunitz Domains Binding loops are underscored.

Hep GF AI T1, K1 (SEQ ID NO:9)
TEDYCLASN<u>KVGRCRGSFPRW</u>YYDPTEQIC<u>KSFVYGGCLGNK</u>NNYLREEE
CILACRGV

Hep GF AI T1, K2 (SEQ ID NO:10)
DKGHCVDLP<u>DTGLCKESIPRW</u>YYNPFSEHC<u>ARFTYGGCYGNK</u>NNFEEEQQ
CLESCRGI

TFPI2-K3 (SEQ ID NO:11)
IPSFCYSPK<u>DEGLCSANVTRY</u>YFNPRYRTC<u>DAFTYTGCGGND</u>NNFVSRED
CKRACAKA

ITI, K2 (SEQ ID NO:12)
AACNLPI<u>VRGPCRAFIQLW</u>AFDAVKGKC<u>VLFPYGGCQGNG</u>NKFYSEKECR
EYCGVP

Hep GF AI T2, K1 (SEQ ID NO:13)
IHDFCLVSK<u>VVGRCRASMPRW</u>WYNVTDGSC<u>QLFVYGGCDGNS</u>NNYLTKEE
CLKKCATV

App2 (SEQ ID NO:14)
VKAVCSQEA<u>MTGPCRAVMPRW</u>YFDLSKGKC<u>VRFIYGGCGGNR</u>NNFESEDY
CMAVCKAM

TFPI1 K2 = LACI-D2 (SEQ ID NO:15)
KPDFCFLEE<u>DPGICRGYITRY</u>FYNNQTKQC<u>ERFKYGGCLGNM</u>NNFETLEE
CKNICEDG

TFPI2-K2 (SEQ ID NO:16)
VPKVCRLQVS<u>VDDQCEGSTEKY</u>FFNLSSMTC<u>EKFFSGGCHRNR</u>IENRFPD
EATCMGFCAPK

HKI B9 (SEQ ID NO:17)
LPNVCAFPM<u>EKGPCQTYMTRW</u>FFNFETGEC<u>ELFAYGGCGGNS</u>NNFLRKEK
CEKFCKFT

TFPI1 K1 = LACI-D1 (SEQ ID NO:18)
MHSFCAFK<u>ADDGPCKAIMKRF</u>FFNIFTRQC<u>EEFIYGGCEGNQ</u>NRFESLEE
CKKMCTRD

TFPI1 K3 = LACI-D3 (SEQ ID NO:19)
GPSWCLTPA<u>DRGLCRANENRF</u>YYNSVIGKC<u>RPFKYSGCGGNE</u>NNFTSKQE
CLRACKKG

Collagen A3 (SEQ ID NO:20)
ETDICKLPK<u>DEGTCRDFILKW</u>YYDPNTKSC<u>ARFWYGGCGGNE</u>NKFGSQKE
CEKVCAPV CAB37635 (SEQ ID NO:21)
KQDVCEMPK<u>ETGPCLAYFLHW</u>WYDKKDNTC<u>SMFVYGGCQGNN</u>NNFQSKAN
CLNTCKNK End Table 2.

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda Md.), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314. The SMART database (Simple Modular Architecture Research Tool, EMBL, Heidelberg, Del.) of HMMs as described in Schultz et al. (1998), *Proc. Natl. Acad. Sci. USA* 95:5857 and Schultz et al. (2000) *Nucl. Acids Res* 28:231. The SMART database contains domains identified by profiling with the hidden Markov models of the HMMer2 search program (R. Durbin et al. (1998) *Biological sequence analysis: probabilistic models of proteins and nucleic acids*. Cambridge University Press). The database also is annotated and monitored. The ProDom protein domain database consists of an automatic compilation of homologous domains (Corpet et al. (1999), *Nucl. Acids Res.* 27:263-267). Current versions of ProDom are built using recursive PSI-BLAST searches (Altschul et al. (1997) *Nucleic Acids Res.* 25:3389-3402; Gouzy et al (1999) *Computers and Chemistry* 23:333-340.) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. 30:235-238(2002).

Useful Kunitz domains for selecting protease inhibitors can include Kunitz domains that have a framework region with a particular number of lysine residues. In one implementation, frameworks with four lysine residues are useful and can be modified, e.g., by attachment of PEG moieties of average molecular weight between 3-8 kDa, e.g., about 5 kDa. For example, the ITI framework has four lysines. In another implementation, frameworks with three lysines are useful and can be modified e.g., by attachment of PEG moieties of average molecular weight between 4-10 kDa, e.g., about 5 kDa or 7 kDa. LACI is one such framework. Frameworks can also be altered to include fewer or additional lysines, for example, to reduce the number of lysines that are within five, four, or three residues of a binding loop, or to introduce a sufficient number of lysines that the protein can be modified with small PEG moieties (e.g., between 3-8 kDa PEG moieties) to increase the size of the protein and stability of the protein in vivo.

Kunitz domains interact with target protease using, primarily, amino acids in two loop regions ("binding loops"). The first loop region is between about residues corresponding to amino acids 11-21 of BPTI. The second loop region is between about residues corresponding to amino acids 31-42 of BPTI. An exemplary library of Kunitz domains varies one or more amino acid positions in the first and/or second loop regions. Particularly useful positions to vary include: positions 13, 16, 17, 18, 19, 31, 32, 34, and 39 with respect to the sequence of BPTI. At least some of these positions are expected to be in close contact with the target protease.

The "framework region" of a Kunitz domain is defined as those residues that are a part of the Kunitz domain, but specifically excluding residues in the first and second binding loops regions, i.e., about residues corresponding to amino acids 11-21 of BPTI and 31-42 of BPTI.

Conversely, residues that are not at these particular positions or which are not in the loop regions may tolerate a wider range of amino acid substitution (e.g., conservative and/or non-conservative substitutions) than these amino acid positions.

Elastase-Inhibiting Kunitz domains

One exemplary polypeptide that binds to and inhibits human neutrophil elastase (hNE) is DX-890 (also known as "EPI-hNE4"). DX-890 is a highly specific and potent (Ki=4×

$10^{-12}$ M) inhibitor of human neutrophil elastase (hNE). DX-890 includes the following amino acid sequence:

```
                                         (SEQ ID NO:23)
Glu Ala Cys Asn Leu Pro Ile Val Arg Gly Pro Cys

Ile Ala Phe Phe Pro Arg Trp Ala Phe Asp Ala Val

Lys Gly Lys Cys Val Leu Phe Pro Tyr Gly Gly Cys

Gln Gly Asn Gly Asn Lys Phe Tyr Ser Glu Lys Glu

Cys Arg Glu Tyr Cys Gly Val Pro
```

DX-890 is derived from the second Kunitz-type domain of inter-α-inhibitor protein (ITI-D2) and can be produced by fermentation in *Pichia pastoris*. It includes 56 amino acids, with a predicted MW of 6,237 Daltons. DX-890 is resistant to oxidative and proteolytic inactivation.

In vitro, ex vivo and in vivo pharmacological studies have demonstrated hNE inhibitory capacity and the protective effect of DX-890 against lesions induced by hNE of sputum from cystic fibrosis children (see ref. Delacourt et al. 2002). Acute and subchronic 4-week studies of aerosolised DX-890 in cynomolgus monkeys showed no signs of clinical or biological toxicity, nor of histopathological lesions induced by the administration of DX-890.

In clinical studies using healthy human volunteers, DX-890 was found to be safe for administration by inhalation at 8 increasing doses (up to 120 minutes of DX-890 in saline resulting in an inhaled mass of about 72 mg).

Some of the consequences of elastase activity include: cleavage of complement receptors and C3bi; cleavage of immunoglobulins; degradation of elastin (and consequently plugging of airways, structural damage, bronchiectasis); secretion of macromolecules; increased interleukin-8; increase in PMN (and consequently release of oxygen, hydrogen peroxide, leukotriene B4 and interleukin-8); and persistence of bacteria. Inhibitors of elastase can be used to reduce one or more of these activities.

DX-890 can be used as an anti-inflammatory drug targeted against neutrophil mediated inflammation, e.g., in pulmonary CF lesions. Exemplary pulmonary indications include Cystic Fibrosis (CF), Acute Respiratory Distress Syndrome (ARDS), and Chronic Obstructive Pulmonary Disease (COPD). In CF patients, the balance between proteinases and their inhibitors may become severely disturbed. Activated polymorphonuclear leukocytes (PMN) produce human neutrophil elastase (hNE) and other proteases. hNE is considered to be a key cause of lung tissue damage associated with cystic fibrosis. Inhibition of hNE is therefore a logical avenue for treatment of CF lung disease since it attacks the original source of damage rather than ameliorating symptoms and consequences of the damage.

It is possible, for example, to deliver DX-890 to the lung by nebulization. DX-890 activity was detected in broncho-alveolar lavages of volunteer inhaling nebulized DX-890. 12 healthy volunteers received during 14 days a single daily dose of DX-890, by nebulization lasting 5 or 20 minutes, corresponding to estimated inhaled mass of 3.75 or 15 mg respectively. Tolerability was excellent; no significant adverse event was reported. No clinical or biological abnormalities were observed.

With respect to pulmonary indications, DX-890 can be used to treat, for example, Cystic Fibrosis (CF), Acute Respiratory Distress Syndrome (ARDS) and Chronic Obstructive Pulmonary Disease (COPD).

There are also known correlations between the structure of DX-890 and its ability to bind to hNE. See, e.g., U.S. Pat. No. 5,663,143. U.S. Pat. No. 5,663,143 also describes other Kunitz domains that inhibit elastase. These and related domains (e.g., domains at least 70, 75, 80, 85, 90, or 95% identical) can also be used.

Exemplary Kunitz domains that inhibit plasma kallikrein are described, for example, in U.S. Pat. No. 6,057,287.

Exemplary Kunitz domains that inhibit plasmin are described, for example, in U.S. Pat. No. 6,103,499.

TABLE 3

Exemplary Amino Acids for hNE inhibitors
Some preferred Amino acids in hNE-inhibiting
Kunitz domains Position Allowed amino acids
at amino acid positions corresponding to
respective positions in BPTI

| | |
|---|---|
| 5 | C |
| 10 | YSVN |
| 11 | TARQP |
| 12 | G |
| 13 | PAV |
| 14 | C |
| 15 | IV |
| 16 | AG |
| 17 | FILVM |
| 18 | F |
| 19 | PSQKR |
| 20 | R |
| 21 | YWF |
| 30 | C |
| 31 | QEV |
| 32 | TLP |
| 33 | F |
| 34 | VQP |
| 35 | Y |
| 36 | G |
| 37 | G |
| 38 | C |
| 39 | MQ |
| 40 | GA |
| 41 | N |
| 42 | G |
| 43 | N |
| 45 | F |
| 51 | C |
| 55 | C |

"Protection against acute lung injury by intravenous or intratracheal pretreatment with EPI-HNE4, a new potent neutrophil elastase inhibitor." Delacourt C, Herigault S, Delclaux C, et al. Am J Respir Cell Mol Biol 2002;26:290-7 and Grimbert et al. (2003) "Characteristics of EPI-hNE4 aerosol: a new elastase inhibitor for treatment of cystic fibrosis" J Aerosol Med. 16(2):121-9.

Identifying Kunitz Domains and Other Protease Inhibitors

A variety of methods can be used to identify a protein that binds to and/or inhibits a protease. These methods can be used to identify natural and non-naturally occurring Kunitz domains that can be used as components of the compounds described herein.

For example, a Kunitz domain can be identified from a library of proteins in which each of a plurality of library members includes a varied Kunitz domain. A variety of amino acids can be varied in the domain. See, e.g., U.S. Pat. No. 5,223,409; U.S. Pat. No. 5,663,143, and U.S. Pat. No. 6,333, 402. Kunitz domains can varied, e.g., using DNA mutagenesis, DNA shuffling, chemical synthesis of oligonucleotides (e.g., using codons as subunits), and cloning of natural genes. See, e.g., U.S. Pat. No. 5,223,409 and U.S. 2003-0129659.

The library can be an expression library that is used to produce proteins. The proteins can be arrayed, e.g., using a protein array. U.S. Pat. No. 5,143,854; De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 0/98534, WO01/83827, WO02/12893, WO 00/63701, WO 01/40803 and WO 99/51773.

The proteins can also be displayed on a replicable genetic package, e.g., in the form of a phage library such as a phage display, yeast display library, ribosome display, or nucleic acid-protein fusion library. See, e.g., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982 for examples of phage display and other methods. See, e.g., Boder and Wittrup (1997) *Nat. Biotechnol.* 15:553-557 and WO 03/029456 for examples of yeast cell display and other methods. See, e.g., Mattheakis et al (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30. and Schaffitzel et al. (1999) *J Immunol Methods.* 231(1-2):119-35 for examples of ribosome display and other methods. See, e.g., Roberts and Szostak (1997) *Proc. Natl. Acad. Sci. USA* 94:12297-12302, and U.S. Pat. No. 6,207,446 for examples of nucleic acid-protein fusions. Such libraries can be screened in a high throughput format. See, e.g., U.S. 2003-0129659.

Libraries of Kunitz domains can be generated by varying one or more binding site loop amino acid residues using a Kunitz domain described herein, e.g., a Kunitz domain having a framework described herein, e.g., a modified or naturally occurring framework region. In one embodiment, the residues that are varied are varied among a plurality of amino acids. The plurality is chosen such that lysine is unavailable.

Screening Display Libraries

This section describes exemplary methods of screening a display library to identify a polypeptide that interacts with an elastase. These methods can be modified to identify other polypeptides that interact with other targets, e.g., other proteases or other proteins. The methods can also be modified and used in combination with other types of libraries, e.g., an expression library or a protein array, and so forth.

In an exemplary display library screen, a phage library is contacted with and allowed to bind to the target elastase protein (e.g., an active or an inactivated form (e.g., mutant or chemically inactivated protein) or a fragment thereof). To facilitate separation of binders and non-binders in the screening process, it is often convenient to immobilize the elastase on a solid support, although it is also possible to first permit binding to elastase in solution and then segregate binders from non-binders by coupling the target compound to a support. By way of illustration, when incubated in the presence of the elastase, phage displaying a polypeptide that interacts with elastase form a complex with the elastase immobilized on a solid support whereas non-binding phage remain in solution and may be washed away with buffer. Bound phage may then be liberated from the elastase by a number of means, such as changing the buffer to a relatively high acidic or basic pH (e.g., pH 2 or pH 10), changing the ionic strength of the buffer, adding denaturants, adding a competitor, adding a host cell which can be infected, or other known means.

For example, to identify elastase-binding peptides, elastase can be adsorbed to a solid surface, such as the plastic surface of wells in a multi-well assay plate. Subsequently, an aliquot of a phage display library is added to a well under appropriate conditions that maintain the structure of the immobilized elastase and the phage, such as pH 6-7. Phage in the libraries that display polypeptides that bind the immobilized elastase are bound to the elastase and are retained in the well. Non-binding phage can be removed. It is also possible to include a blocking agent or competing ligand during the binding of the phage library to the immobilized elastase.

Phage bound to the immobilized elastase may then be eluted by washing with a buffer solution having a relatively strong acid pH (e.g., pH 2) or an alkaline pH (e.g., pH 8-9). The solutions of recovered phage that are eluted from the elastase are then neutralized and may, if desired, be pooled as an enriched mixed library population of phage displaying elastase binding peptides. Alternatively the eluted phage from each library may be kept separate as a library-specific enriched population of elastase binders. Enriched populations of phage displaying elastase binding peptides may then be grown up by standard methods for further rounds of screening and/or for analysis of peptide displayed on the phage and/or for sequencing the DNA encoding the displayed binding peptide.

One of many possible alternative screening protocols uses elastase target molecules that are biotinylated and that can be captured by binding to streptavidin, for example, coated on particles.

Recovered phage may then be amplified by infection of bacterial cells, and the screening process may be repeated with the new pool of phage that is now depleted in non-elastase binders and enriched in elastase binders. The recovery of even a few binding phage may be sufficient to carry the process to completion. After a few rounds of selection, the gene sequences encoding the binding moieties derived from selected phage clones in the binding pool are determined by conventional methods, revealing the peptide sequence that imparts binding affinity of the phage to the target. An increase in the number of phage recovered after each round of selection and the recovery of closely related sequences indicate that the screening is converging on sequences of the library having a desired characteristic.

After a set of binding polypeptides is identified, the sequence information may be used to design other, secondary libraries. For example, the secondary libraries can explore a smaller segment of sequence space in more detail than the initial library. In some embodiments, the secondary library includes proteins that are biased for members having additional desired properties, e.g., sequences that have a high percentage identity to a human protein.

Display technology can also be used to obtain polypeptides that are specific to particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library Iterative Selection. In one preferred embodiment, display library technology is used in an iterative mode. A first display library is used to identify one or more proteins that interacts with a target. These identified proteins are then varied using a mutagenesis method to form a second display library. Higher affinity proteins are then selected from the second library, e.g., by using higher stringency or more competitive binding and washing conditions.

In some implementations, the mutagenesis is targeted to regions known or likely to be at the binding interface. Some exemplary mutagenesis techniques include: error-prone PCR (Leung et al. (1989) *Technique* 1:11-15), recombination, DNA shuffling using random cleavage (Stemmer (1994) *Nature* 389-391; termed "nucleic acid shuffling"), RACHITT™ (Coco et al. (2001) *Nature Biotech.* 19:354), site-directed mutagenesis (Zoller et al (1987) *Nucl Acids Res* 10:6487-6504), cassette mutagenesis (Reidhaar-Olson (1991) *Methods Enzymol.* 208:564-586) and incorporation of degenerate oligonucleotides (Griffiths et al. (1994) *EMBO J.* 13:3245). For Kunitz domains, many positions near the binding interface are known. Such positions include, for example, positions 13, 16, 17, 18, 19, 31, 32, 34, and 39 with respect to the sequence of BPTI. (according to the BPTI numbering in U.S. Pat. No. 6,333,402). Such positions can be held constant and other positions can be varied or these positions themselves may be varied.

In one example of iterative selection, the methods described herein are used to first identify proteins from a display library that bind an elastase with at least a minimal binding specificity for a target or a minimal activity, e.g., an equilibrium dissociation constant for binding of greater than 1 nM, 10 nM, or 100 nM. The nucleic acid sequences encoding the initial identified proteins are used as a template nucleic acid for the introduction of variations, e.g., to identify a second protein ligand that has enhanced properties (e.g., binding affinity, kinetics, or stability) relative to the initial protein ligand.

Off-Rate Selection. Since a slow dissociation rate can be predictive of high affinity, particularly with respect to interactions between proteins and their targets, the methods described herein can be used to isolate proteins with a desired kinetic dissociation rate (i.e. reduced) for a binding interaction to a target.

To select for slow dissociating proteins from a display library, the library is contacted to an immobilized target, e.g., immobilized elastase. The immobilized target is then washed with a first solution that removes non-specifically or weakly bound biomolecules. Then the immobilized target is eluted with a second solution that includes a saturation amount of free target, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards display library members that bind to a non-target molecule, e.g., a protease other than elastase, such as trypsin. In one embodiment, the non-target molecule is elastase that has been activated by treatment with an irreversibly bound inhibitor, e.g., a covalent inhibitor.

In one implementation, a so-called "negative selection" step or "depletion" is used to discriminate between the target and a related, but distinct or an unrelated non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data are compared (e.g., using a computer and software) to identify library members that specifically bind to the target.

Modifying and Varying Polypeptides

It is also possible to vary a protein described herein to obtain useful variant protein that has similar or improved or altered properties. Typically, a number of variants are possible. A variant can be prepared and then tested, e.g., using a binding assay described herein (such as fluorescence anisotropy).

One type of variant is a truncation of a ligand described herein or isolated by a method described herein. In this example, the variant is prepared by removing one or more amino acid residues of the ligand from the N or C terminus. In some cases, a series of such variants is prepared and tested. Information from testing the series is used to determine a region of the ligand that is essential for binding the elastase protein. A series of internal deletions or insertions can be similarly constructed and tested. For Kunitz domains, it can be possible to remove, e.g., between one and five residues or one and three residues that are N-terminal to $C_5$, the first cysteine, and between one and five residues or one and three residues that are C-terminal to $C_{55}$, the final cysteine, wherein each of the cysteines corresponds to a respectively numbered cysteine in BPTI.

Another type of variant is a substitution. In one example, the ligand is subjected to alanine scanning to identify residues that contribute to binding activity. In another example, a library of substitutions at one or more positions is constructed. The library may be unbiased or, particularly if multiple positions are varied, biased towards an original residue. In some cases, the substitutions are all conservative substitutions.

Another type of variant includes one or more non-naturally occurring amino acids. Such variant ligands can be produced by chemical synthesis or modification. One or more positions can be substituted with a non-naturally occurring amino acid. In some cases, the substituted amino acid may be chemically related to the original naturally occurring residue (e.g., aliphatic, charged, basic, acidic, aromatic, hydrophilic) or an isostere of the original residue.

It may also be possible to include non-peptide linkages and other chemical modifications. For example, part or all of the ligand may be synthesized as a peptidomimetic, e.g., a peptoid (see, e.g., Simon et al. (1992) *Proc. Natl. Acad. Sci. USA* 89:9367-71 and Horwell (1995) *Trends Biotechnol.* 13:132-4). See also other modifications discussed below.

Characterization of Binding Interactions

The binding properties of a protein (e.g., a polypeptide that includes a Kunitz domain) can be readily assessed using various assay formats. For example, the binding property of a protein can be measured in solution by fluorescence anisotropy, which provides a convenient and accurate method of determining a dissociation constant ($K_D$) or association constant (Ka) of the protein for a particular target. In one such procedure, the protein to be evaluated is labeled with fluorescein. The fluorescein-labeled protein is mixed in wells of a multi-well assay plate with various concentrations of the particular target (e.g., elastase). Fluorescence anisotropy measurements are carried out using a fluorescence polarization plate reader.

ELISA. The binding interactions can also be analyzed using an ELISA assay. For example, the protein to be evaluated is contacted to a microtitre plate whose bottom surface has been coated with the target, e.g., a limiting amount of the target. The molecule is contacted to the plate. The plate is washed with buffer to remove non-specifically bound molecules. Then the amount of the protein bound to the plate is determined by probing the plate with an antibody that recognizes the protein. For example, the protein can include an epitope tag. The antibody can be linked to an enzyme such as alkaline phosphatase, which produces a calorimetric product when appropriate substrates are provided. In the case where a display library member includes the protein to be tested, the antibody can recognize a region that is constant among all display library members, e.g., for a phage display library member, a major phage coat protein.

Homogeneous Assays. A binding interaction between a protein and a particular target can be analyzed using a homogenous assay, i.e., after all components of the assay are added, additional fluid manipulations are not required. For example, fluorescence energy transfer (FET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). By titrating the amount of the first or second binding molecule, a binding curve can be generated to estimate the equilibrium binding constant.

Surface Plasmon Resonance (SPR). A binding interaction between a protein and a particular target can be analyzed using SPR. For example, after sequencing of a display library member present in a sample, and optionally verified, e.g., by ELISA, the displayed protein can be produced in quantity and assayed for binding the target using SPR. SPR or real-time Biomolecular Interaction Analysis (BIA) detects biospecific interactions in real time, without labeling any of the interactants (e.g., BIAcore). Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander, S. and Urbaniczky, C. (1991) *Anal. Chem.* 63:2338-2345; Szabo et al. (1995) *Curr. Opin. Struct. Biol.* 5:699-705.

Information from SPR can be used to provide an accurate and quantitative measure of the equilibrium dissociation constant ($K_d$), and kinetic parameters, including $k_{on}$ and $k_{off}$, for the binding of a biomolecule to a target. Such data can be used to compare different biomolecules. For example, proteins selected from a display library can be compared to identify individuals that have high affinity for the target or that have a slow $k_{off}$. This information can also be used to develop structure-activity relationship (SAR) if the biomolecules are related. For example, if the proteins are all mutated variants of a single parental antibody or a set of known parental antibodies, variant amino acids at given positions can be identified that correlate with particular binding parameters, e.g., high affinity and slow $k_{off}$.

Additional methods for measuring binding affinities include fluorescence polarization (FP) (see, e.g., U.S. Pat. No. 5,800,989), nuclear magnetic resonance (NMR), and binding titrations (e.g., using fluorescence energy transfer).

Other solution measures for studying binding properties include fluorescence resonance energy transfer (FRET) and NMR.

Characterization of Elastase Inhibition

With respect to embodiments in which the compound includes a polypeptide that has a Kunitz domain specific for elastase, it may be useful to characterize the ability of the polypeptide to inhibit elastase.

Kunitz domains can be screened for binding to elastase and for inhibition of elastase proteolytic activity. Kunitz domains can be selected for their potency and selectivity of inhibition of elastase. In one example, elastase and its substrate are combined under assay conditions permitting reaction of the protease with its substrate. The assay is performed in the absence of the Kunitz domain, and in the presence of increasing concentrations of the Kunitz domain. The concentration of test compound at which 50% of the elastase activity is inhibited by the test compound is the $IC_{50}$ value (Inhibitory Concentration) or $EC_{50}$ (Effective Concentration) value for that compound. Within a series or group of Kunitz domain, those having lower $IC_{50}$ or $EC_{50}$ values are considered more potent inhibitors of the elastase than those compounds having higher $IC_{50}$ or $EC_{50}$ values. Preferred compounds according to this aspect have an $IC_{50}$ value of 100 nM or less as measured in an in vitro assay for inhibition of elastase activity.

Kunitz domain can also be evaluated for selectivity toward elastase. A test compound is assayed for its potency toward a panel of serine proteases and other enzymes and an $IC_{50}$ value is determined for each peptide. A Kunitz domain that demonstrates a low $IC_{50}$ value for the elastase enzyme, and a higher $IC_{50}$ value for other enzymes within the test panel (e.g., trypsin, plasmin, kallikrein), is considered to be selective toward elastase. Generally, a compound is deemed selective if its $IC_{50}$ value is at least one order of magnitude less than the next smallest $IC_{50}$ value measured in the panel of enzymes.

Specific methods for evaluating inhibition of elastase are described in the Example below.

It is also possible to evaluate Kunitz domain activity in vivo or in samples (e.g., pulmonary lavages) of subjects to which a compound described herein has been administered.

Protease Targets

Proteases are involved in a wide variety of biological processes, including inflammation and tissue injury. Serine proteases produced by inflammatory cells, including neutrophils, are implicated in various disorders, such as pulmonary emphysema. Neutrophil elastase is a serine protease produced by polymorphonuclear leukocytes with activity against extracellular matrix components and pathogens. Pulmonary emphysema is characterized by alveolar destruction leading to a major impairment in lung function.

A deficiency of a serine protease inhibitor, α1-protease inhibitor (API, or α1-PI, formerly known as α-1 antitrypsin) is a risk factor for the development of pulmonary emphysema (Laurell, C. B. and Eriksson, S. (1963) *Scand. J. Clin. Lab. Invest.* 15:132-140; Brantly, M. L., et al. (1988) *Am. Rev. Respir. Dis.* 138:327-336). API deficiency may lead to uncontrolled activity of neutrophil elastase and contribute to the destruction of lung tissue in pulmonary emphysema. Likewise, API inactivation and chronic inflammation can lead to excess neutrophil elastase activity and pathologic destruction of pulmonary tissue.

Human neutrophil elastase consists of approximately 218 amino acid residues, contains 2 asparagine-linked carbohydrate side chains, and is joined together by 2 disulfide bonds (Sinha, S., et al. *Proc. Nat. Acad. Sci.* 84: 2228-2232, 1987). It is normally synthesized in the developing neutrophil as a proenzyme but stored in the primary granules in its active form, ready with full enzymatic activity when released from the granules, normally at sites of inflammation (Gullberg U, et al. *Eur J Haematol.* 1997; 58:137-153; Borregaard N, Cowland J B. *Blood.* 1997; 89:3503-3521).

Other exemplary protease targets include: plasmin, kallikrein, Factor VIa, Factor XIa, thrombin, urokinase, and Factor IIa. Classes of relevant proteases include: proteases associated with blood coagulation, proteases associated with complement, proteases that digest extracellular matrix components, proteases that digest basement membranes, and proteases associated with endothelial cells. For example, the protease is a serine protease.

Protein Production

Recombinant production of polypeptides. Standard recombinant nucleic acid methods can be used to express a polypeptide component of a compound described herein (e.g., a polypeptide that includes a Kunitz domain). Generally, a nucleic acid sequence encoding the polypeptide is cloned into a nucleic acid expression vector. If the polypeptide is sufficiently small, e.g., the protein is a peptide of less than 50 amino acids, the protein can be synthesized using automated organic synthetic methods.

The expression vector for expressing the polypeptide can include a segment encoding the polypeptide and regulatory sequences, for example, a promoter, operably linked to the coding segment. Suitable vectors and promoters are known to those of skill in the art and are commercially available for generating the recombinant constructs of the present invention. See, for example, the techniques described in Sambrook & Russell, *Molecular Cloning: A Laboratory Manual*, 3$^{rd}$ Edition, Cold Spring Harbor Laboratory, N.Y. (2001) and Ausubel et al., *Current Protocols in Molecular Biology* (Greene Publishing Associates and Wiley Interscience, N.Y. (1989).

Scopes (1994) *Protein Purification: Principles and Practice*, New York:Springer-Verlag and other texts provide a number of general methods for purifying recombinant (and non-recombinant) proteins.

Synthetic production of peptides. The polypeptide component of a compound can also be produced by synthetic means. See, e.g., Merrifield (1963) *J. Am. Chem. Soc.*, 85: 2149. For example, the molecular weight of synthetic peptides or peptide mimetics can be from about 250 to about 8,0000 Daltons. A peptide can be modified, e.g., by attachment to a moiety that increases the effective molecular weight of the peptide. If the peptide is oligomerized, dimerized and/or derivatized, e.g., with a hydrophilic polymer (e.g., to increase the affinity and/or activity of the peptides), its molecular weights can be greater and can range anywhere from about 500 to about 50,000 Daltons.

Pharmaceutical Compositions

Also featured is a composition, e.g., a pharmaceutically acceptable composition, that includes a poly-PEGylated Kunitz domain. In one embodiment, the Kunitz domain binds to a protease such as elastase, plasmin, or kallikrein. As used herein, "pharmaceutical compositions" encompass compounds (e.g., labeled compounds) for diagnostic (e.g., in vivo imaging) use as well as compounds for therapeutic or prophylactic use.

As used herein, "pharmaceutically acceptable carrier" includes any and all solvents, dispersion media, coatings, antibacterial and antifungal agents, isotonic and absorption delaying agents, and the like that are physiologically compatible. In one embodiment, the carrier is other than water. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for administration of humans with antibodies. The preferred mode of administration is parenteral (e.g., intravenous, subcutaneous, intraperitoneal, intramuscular). In a preferred embodiment, the compound is administered by intravenous infusion or injection. In another preferred embodiment, the compound is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions typically must be sterile and stable under the conditions of manufacture and storage. A pharmaceutical composition can also be tested to insure it meets regulatory and industry standards for administration. For example, endotoxin levels in the preparation can be tested using the Limulus amebocyte lysate assay (e.g., using the kit from Bio Whittaker lot # 7L3790, sensitivity 0.125 EU/mL) according to the USP 24/NF 19 methods. Sterility of pharmaceutical compositions can be determined using thioglycollate medium according to the USP 24/NF 19 methods. For example, the preparation is used to inoculate the thioglycollate medium and incubated at 35° C. for 14 or more days. The medium is inspected periodically to detect growth of a microorganism.

The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The poly-PEGylated Kunitz domains described herein can be administered by a variety of methods known in the art. For many applications, the route/mode of administration is intravenous injection or infusion. For example, for therapeutic applications, the compound can be administered by intravenous infusion at a rate of less than 30, 20, 10, 5, or 1 mg/min to reach a dose of about 1 to 100 mg/m² or 7 to 25 mg/m². The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978. Pharmaceutical formulation is a well-established art, and is further described in Gennaro (ed.), Remington: The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

In certain embodiments, the composition may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compound may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules are also known.

In certain embodiments, the compound can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade (1989) *J. Clin. Pharmacol.* 29:685).

Also within the scope of the invention are kits comprising poly-PEGylated Kunitz domain and instructions for use, e.g., treatment, prophylactic, or diagnostic use. In one embodiment, the kit includes (a) the compound, e.g., a composition that includes the compound, and, optionally, (b) informational material. The informational material can be descriptive, instructional, marketing or other material that relates to the methods described herein and/or the use of the compound for the methods described herein. For example, in the case of a Kunitz domain that inhibits elastase activity, the informational material describes methods for administering the compound to reduce elastase activity or to treat or prevent a pulmonary disorder (e.g., CF or COPD), an inflammatory disorder (e.g., IBD), or a disorder characterized by excessive elastase activity.

In one embodiment, the informational material can include instructions to administer the compound in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., a human having, or at risk for a disorder characterized by excessive elastase activity. The informational material can include information about production of the compound, molecular weight of the compound, concentration, date of expiration, batch or production site information, and so forth. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the compound and/or its use in the methods described herein. Of course, the informational material can also be provided in any combination of formats.

In addition to the compound, the composition of the kit can include other ingredients, such as a solvent or buffer, a stabilizer or a preservative, and/or a second agent for treating a condition or disorder described herein, e.g. a pulmonary (e.g., CF or COPD) or inflammatory (e.g., IBD or RA) disorder. Alternatively, the other ingredients can be included in the kit, but in different compositions or containers than the compound. In such embodiments, the kit can include instructions for admixing the compound and the other ingredients, or for using the compound together with the other ingredients.

The compound can be provided in any form, e.g., liquid, dried or lyophilized form. It is preferred that the compound be substantially pure and/or sterile. When the compound is provided in a liquid solution, the liquid solution preferably is an aqueous solution, with a sterile aqueous solution being preferred. When the compound is provided as a dried form, reconstitution generally is by the addition of a suitable solvent. The solvent, e.g., sterile water or buffer, can optionally be provided in the kit.

The kit can include one or more containers for the composition containing the compound. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate Elements of the kit are contained within a single, undivided container. For example, the composition is contained in a bottle, vial or syringe that has attached thereto the informational material in the form of a label. In some embodiments, the kit includes a plurality (e.g., a pack) of individuals containers, each containing one or more unit dosage forms (e.g., a dosage form described herein) of the compound. For example, the kit includes a plurality of syringes, ampules, foil packets, or blister packs, each containing a single unit dose of the compound. The containers of the kits can be air tight, waterproof (e.g., impermeable to changes in moisture or evaporation), and/or light-tight.

In one embodiment wherein the compound contains a polypeptide that binds to an elastase, the instructions for diagnostic applications include the use of the compound to detect elastase, in vitro, e.g., in a sample, e.g., a biopsy or cells from a patient having a pulmonary disorder, or in vivo. In another embodiment, the instructions for therapeutic applications include suggested dosages and/or modes of administration in a patient with a pulmonary disorder. The kit can further contain a least one additional reagent, such as a diagnostic or therapeutic agent, e.g., a diagnostic or therapeutic agent as described herein, and/or one or more additional agents to treat the pulmonary disorder (e.g., another elastase inhibitor), formulated as appropriate, in one or more separate pharmaceutical preparations.

Treatments

A poly-PEGylated Kunitz domain has therapeutic and prophylactic utilities.

In one embodiment, poly-PEGylated Kunitz domain inhibits an elastase, e.g., a neutrophil elastase. The compound can be administered to a subject to treat, prevent, and/or diagnose a variety of disorders, such as diseases characterized by unwanted or aberrant elastase activity. For example, the disease or disorder can be characterized by enhanced elastolytic activity of neutrophils. The disease or disorder may result from an increased neutrophil burden on a tissue, e.g., an epithelial tissue such as the epithelial surface of the lung. For example, polypeptide that inhibits elastase can be used to treat or prevent pulmonary diseases such as cystic fibrosis (CF) or chronic obstructive pulmonary disorder (COPD), e.g., emphysema. The compound can also be administered to cells, tissues, or organs in culture, e.g., in vitro or ex vivo.

Poly-PEGylated Kunitz domains that inhibit other proteases can also be used to treat or prevent disorders associated with the activity of such other respective proteases.

As used herein, the term "treat" or "treatment" is defined as the application or administration of poly-PEGylated Kunitz domain, alone or in combination with, a second agent to a subject, e.g., a patient, or application or administration of the agent to an isolated tissue or cell, e.g., cell line, from a subject, e.g., a patient, who has a disorder (e.g., a disorder as described herein), a symptom of a disorder or a predisposition toward a disorder, with the purpose to cure, heal, alleviate, relieve, alter, remedy, ameliorate, improve or affect the disorder, the symptoms of the disorder or the predisposition toward the disorder. Treating a cell refers to the inhibition, ablation, killing of a cell in vitro or in vivo, or otherwise reducing capacity of a cell, e.g., an aberrant cell, to mediate a disorder, e.g., a disorder as described herein (e.g., a pulmonary disorder). In one embodiment, "treating a cell" refers to a reduction in the activity and/or proliferation of a cell, e.g., a leukocyte or neutrophil. Such reduction does not necessarily indicate a total elimination of the cell, but a reduction, e.g., a statistically significant reduction, in the activity or the number of the cell.

As used herein, an amount of a poly-PEGylated Kunitz domain effective to treat a disorder, or a "therapeutically effective amount" refers to an amount of the compound which is effective, upon single or multiple dose administration to a subject, in treating a subject, e.g., curing, alleviating, relieving or improving at least one symptom of a disorder in a subject to a degree beyond that expected in the absence of such treatment. For example, the disorder can be a pulmonary disorder, e.g., a pulmonary disorder described herein.

A "locally effective amount" refers to the amount (e.g., concentration) of the compound which is effective at detectably modulating activity of a target protein (e.g., elastase) in a tissue, e.g., in a region of the lung exposed to elastase, or a elastase-producing cell, such as a neutrophil. Evidence of modulation can include, e.g., increased amount of substrate, e.g., reduced proteolysis of the extracellular matrix.

As used herein, an amount of poly-PEGylated Kunitz domain effective to prevent a disorder, or a "prophylactically effective amount" of the compound refers to an amount of an elastase-binding compound, e.g., a polypeptide-polymer compound described herein, which is effective, upon single- or multiple-dose administration to the subject, in preventing or delaying the occurrence of the onset or recurrence of a disorder, e.g., a pulmonary disorder.

The terms "induce," "inhibit," "potentiate," "elevate," "increase," "decrease" or the like, e.g., which denote quantitative differences between two states, refer to a difference, e.g., a statistically significant difference (e.g., $P<0.05$, 0.02, or 0.005), between the two states.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

An exemplary, non-limiting range for a therapeutically or prophylactically effective amount of a compound described herein is 0.1-20 mg/kg, more preferably 1-10 mg/kg. The compound can be administered by intravenous infusion at a rate of less than 20, 10, 5, or 1 mg/min to reach a dose of about 1 to 50 mg/m$^2$ or about 5 to 20 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are only exemplary.

A pharmaceutical composition may include a "therapeutically effective amount" or a "prophylactically effective amount" of a compound described herein, e.g., a compound that includes a polypeptide that binds and inhibits a protease (e.g., elastase). A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects. A "therapeutically effective dosage" preferably inhibits a measurable parameter, e.g., an increase in pulmonary function, relative to untreated subjects. The ability of a compound to inhibit a measurable parameter can be evaluated in an animal model system predictive of efficacy in a human disorder. Alternatively, this property of a composition can be evaluated by examining the ability of the compound to inhibit, such inhibition in vitro by assays known to the skilled practitioner, e.g., an assay described herein.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

As used herein, the term "subject" is intended to include human and non-human animals. The term "non-human animals" of the invention includes all vertebrates, e.g., non-mammals (such as chickens, amphibians, reptiles) and mammals, such as non-human primates, sheep, dog, cow, pig, etc.

In one embodiment, the subject is a human subject. Alternatively, the subject can be a non-human mammal expressing a human neutrophil elastase or an endogenous non-human neutrophil elastase protein or an elastase-like antigen to which an elastase-binding compound cross-reacts. A compound of the invention can be administered to a human subject for therapeutic purposes (discussed further below). Moreover, an elastase-binding compound can be administered to a non-human mammal expressing the elastase-like antigen to which the compound binds (e.g., a primate, pig or mouse) for veterinary purposes or as an animal model of human disease. Regarding the latter, such animal models may be useful for evaluating the therapeutic efficacy of the compound (e.g., testing of dosages and time courses of administration).

The subject method can be used on cells in culture, e.g. in vitro or ex vivo. The method can be performed on cells present in a subject, as part of an in vivo (e.g., therapeutic or prophylactic) protocol. For in vivo embodiments, the contacting step is effected in a subject and includes administering the elastase-binding compound to the subject under conditions effective to permit both binding of the compound to a target (e.g., an elastase) in the subject.

The compounds which inhibit elastase can reduce elastase-mediated degradation and its sequelae, such as persistent infection and inflammation, leading to destruction of tissue (e.g., destruction of airway epithelium).

Methods of administering compounds are described in "Pharmaceutical Compositions". Suitable dosages of the compounds used will depend on the age and weight of the subject and the particular drug used. The compounds can be used as competitive agents to inhibit, reduce an undesirable interaction, e.g., between a natural or pathological agent and the elastase, e.g., between the extracellular matrix and elastase.

In one embodiment, the compounds are used to kill or ablate cells that express elastase in vivo. The compounds can be used by themselves or conjugated to an agent, e.g., a cytotoxic drug, radioisotope. This method includes: administering the compound alone or attached to a cytotoxic drug, to a subject requiring such treatment.

The terms "cytotoxic agent" and "cytostatic agent" refer to agents that have the property of inhibiting the growth or proliferation (e.g., a cytostatic agent), or inducing the killing of cells.

Poly-PEGylated Kunitz domain may also be used to deliver a variety of drugs including therapeutic drugs, a compound emitting radiation, molecules of plants, fungal, or bacterial origin, biological proteins, and mixtures thereof. For example, the Kunitz domain can be used to target the payload to a region of a subject which includes a protease that specifically interacts with the Kunitz domain.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. Procedures for preparing enzymatically active polypeptides of the immunotoxins are described in WO 84/03508 and WO 85/03508. Examples of cytotoxic moieties that can be conjugated to the antibodies include adriamycin, chlorambucil, daunomycin, methotrexate, neocarzinostatin, and platinum.

In the case of polypeptide toxins, recombinant nucleic acid techniques can be used to construct a nucleic acid that encodes the polypeptide including a Kunitz domain and the cytotoxin (or a polypeptide component thereof) as translational fusions. The recombinant nucleic acid is then expressed, e.g., in cells and the encoded fusion polypeptide isolated. Then the fusion protein is physically associated with a moiety that increases the molecular weight of the compound, e.g., to stabilize half-life in vivo, and then attached to a moiety (e.g., a polymer).

Procedures for conjugating proteins with the cytotoxic agents have been previously described. For conjugating chlorambucil with proteins, see, e.g., Flechner (1973) *European Journal of Cancer*, 9:741-745; Ghose et al. (1972) *British Medical Journal*, 3:495-499; and Szekerke, et al. (1972) *Neoplasma*, 19:211-215. For conjugating daunomycin and adriamycin to proteins, see, e.g., Hurwitz, E. et al. (1975) *Cancer Research*, 35:1175-1181 and Amon et al. (1982) *Cancer Surveys*, 1:429-449. For preparing protein-ricin conjugates, see, e.g., U.S. Pat. No. 4,414,148 and by Osawa, T., et al. (1982) *Cancer Surveys*, 1:373-388 and the references cited therein. Coupling procedures as also described in EP 226 419.

Also encompassed by the present invention is a method of killing or ablating which involves using the compound for prophylaxis. For example, these materials can be used to prevent or delay development or progression of a lung disease.

Use of the therapeutic methods of the present invention to treat lung diseases has a number of benefits. Since the polypeptide portion of the compound specifically recognizes elastase, other tissue is spared and high levels of the agent are delivered directly to the site where therapy is required. Treatment in accordance with the present invention can be effectively monitored with clinical parameters. Alternatively, these parameters can be used to indicate when such treatment should be employed.

Pulmonary Disorders and Methods and Formulations hNE inhibitor polypeptides that are physically associated with a moiety (e.g., a polymer) can be used to treat pulmonary disorders such as emphysema, cystic fibrosis, COPD, bronchitis, pulmonary hypertension, acute respiratory distress syndrome, interstitial lung disease, asthma, smoke intoxication, bronchopulmonary dysplasia, pneumonia, thermal injury, and lung transplant rejection.

Cystic Fibrosis. Cystic fibrosis (CF) is a genetic disease affecting approximately 30,000 children and adults in the United States. A defect in the CF gene causes the body to produce an abnormally thick, sticky mucus that clogs the lungs and leads to life-threatening lung infections. A diagnostic for the genetic disorder includes a sweat test which can include measuring chloride concentration in sweat collected on gauze or filter paper, measuring sodium concentration in sweat collected on gauze or filter paper, and pilocarpine delivery and current density in sweat collection. The gene that causes CF has been identified and a number of mutations in the gene are known.

In one embodiment, a hNE inhibitor polypeptide that is physically associated with a moiety (e.g., a polymer) is used to ameliorate at least one symptom of CF, e.g., to reduce pulmonary lesions in the lungs of a CF patient.

This compound can also be used to ameliorate at least one symptom of a chronic obstructive pulmonary disease (COPD). Emphysema, along with chronic bronchitis, is part of chronic obstructive pulmonary disease (COPD). It is a serious lung disease and is progressive, usually occurring in elderly patients. COPD causes over-inflation of structures in the lungs known as alveoli or air sacs. The walls of the alveoli break down resulting in a decrease in the respiratory ability of the lungs. Patients with this disease may first experience shortness of breath and cough. One clinical index for evaluating COPD is the destructive index which measures a measure of alveolar septal damage and emphysema, and has been proposed as a sensitive index of lung destruction that closely reflects functional abnormalities, especially loss of elastic recoil. See, e.g., Am Rev Respir Dis 1991 July; 144(1):156-9. The compound can be used to reduce the destructive index in a patient, e.g., a statistically significant amount, e.g., at least 10, 20, 30, or 40% or at least to within 50, 40, 30, or 20% of normal of a corresponding age and gender-matched individual.

In one aspect, the invention provides a composition that poly-PEGylated Kunitz domain that is an hNE inhibitor for treatment of a pulmonary disorder (e.g., cystic fibrosis, COPD). The composition can be formulated for inhalation or other mode of pulmonary delivery. Accordingly, the compounds described herein can be administered by inhalation to pulmonary tissue. The term "pulmonary tissue" as used herein refers to any tissue of the respiratory tract and includes both the upper and lower respiratory tract, except where otherwise indicated. A hNE inhibitor polypeptide that is physically associated with a moiety (e.g., a polymer) can be administered in combination with one or more of the existing modalities for treating pulmonary diseases.

In one example the compound is formulated for a nebulizer. In one embodiment, the compound can be stored in a lyophilized form (e.g., at room temperature) and reconstituted in solution prior to inhalation. In another embodiment, the compound is stored at an acidic pH (e.g., a pH less than 5, 4, or 3) and then combined with a neutralizing buffer having a basic pH prior to inhalation.

It is also possible to formulate the compound for inhalation using a medical device, e.g., an inhaler. See, e.g., U.S. Pat. No. 6,102,035 (a powder inhaler) and U.S. Pat. No. 6,012,454 (a dry powder inhaler). The inhaler can include separate compartments for the active compound at an acidic pH and the neutralizing buffer and a mechanism for combining the compound with a neutralizing buffer immediately prior to atomization. In one embodiment, the inhaler is a metered dose inhaler.

The three common systems used to deliver drugs locally to the pulmonary air passages include dry powder inhalers (DPIs), metered dose inhalers (MDIs) and nebulizers. MDIs, the most popular method of inhalation administration, may be used to deliver medicaments in a solubilized form or as a dispersion. Typically MDIs comprise a Freon or other relatively high vapor pressure propellant that forces aerosolized medication into the respiratory tract upon activation of the device. Unlike MDIs, DPIs generally rely entirely on the inspiratory efforts of the patient to introduce a medicament in a dry powder form to the lungs. Nebulizers form a medicament aerosol to be inhaled by imparting energy to a liquid solution. Direct pulmonary delivery of drugs during liquid ventilation or pulmonary lavage using a fluorochemical medium has also been explored. These and other methods can be used to deliver a hNE inhibitor polypeptide that is physically associated with a moiety (e.g., a polymer).

For example, for administration by inhalation, poly-PEGylated Kunitz domain that inhibits hNE are delivered in the form of an aerosol spray from pressured container or dispenser which contains a suitable propellant or a nebulizer. The compound may be in the form of a dry particle or as a liquid. Particles that include the compound can be prepared, e.g., by spray drying, by drying an aqueous solution of the poly-PEGylated Kunitz domain that inhibits hNE with a charge neutralizing agent and then creating particles from the dried powder or by drying an aqueous solution in an organic modifier and then creating particles from the dried powder.

The compound may be conveniently delivered in the form of an aerosol spray presentation from pressurized packs or a nebulizer, with the use of a suitable propellant, e.g., dichlorodifluoromethane, trichlorofluoromethane, dielilorotetrafluoroctliane, carbon dioxide or other suitable gas. In the case of a pressurized aerosol, the dosage unit may be determined by providing a valve to deliver a metered amount. Capsules and cartridges for use in an inhaler or insufflator may be formulated containing a powder mix of the poly-PEGylated Kunitz domain that inhibits hNE and a suitable powder base such as lactose or starch, if the particle is a formulated particle. In addition to the formulated or unformulated compound, other materials such as 100% DPPC or other surfactants can be mixed with the poly-PEGylated Kunitz domain that inhibit hNE to promote the delivery and dispersion of formulated or unformulated compound. Methods of preparing dry particles are described, for example, in PCT Publication WO 02/32406.

The poly-PEGylated Kunitz domain that inhibits hNE, e.g., as dry aerosol particles, when administered can be rapidly absorbed and can produce a rapid local or systemic therapeutic result. Administration can be tailored to provide detectable activity within 2 minutes, 5 minutes, 1 hour, or 3 hours of administration. In some embodiments, the peak activity can be achieved even more quickly, e.g., within one half hour or even within ten minutes. Alternatively, a poly-PEGylated Kunitz domain that inhibits hNE can be formulated for longer biological half-life can be used as an alternative to other modes of administration, e.g., such that the compound enters circulation from the lung and is distributed to other organs or to a particular target organ.

In one embodiment, poly-PEGylated Kunitz domain that inhibits hNE is delivered in an amount such that at least 5% of the mass of the polypeptide is delivered to the lower respiratory tract or the deep lung. Deep lung has an extremely rich capillary network. The respiratory membrane separating capillary lumen from the alveolar air space is very thin ($\leqq 6$ μm) and extremely permeable. In addition, the liquid layer lining the alveolar surface is rich in lung surfactants. In other embodiments, at least 2%, 3%, 5%, 10%, 20%, 30%, 40%, 50%, 60%, 70%, or 80% of the composition of a poly-PEGylated Kunitz domain that inhibits hNE is delivered to the lower respiratory tract or to the deep lung. Delivery to either or both of these tissues results in efficient absorption of the compound and high bioavailability. In one embodiment, the compound is provided in a metered dose using, e.g., an inhaler or nebulizer. For example, the compound is delivered in a dosage unit form of at least about 0.02, 0.1, 0.5, 1, 1.5, 2, 5, 10, 20, 40, or 50 mg/puff or more.

The percent bioavailability can be calculated as follows: the percent bioavailability=$(AUC_{non-invasive}/AUC_{i.v.\ or\ s.c.}) \times (dose_{i.v.\ or\ s.c.}/dose_{non-invasive}) \times 100$.

Although not necessary, delivery enhancers such as surfactants can be used to further enhance pulmonary delivery. A "surfactant" as used herein refers to a compound having a hydrophilic and lipophilic moiety, which promotes absorption of a drug by interacting with an interface between two immiscible phases. Surfactants are useful in the dry particles for several reasons, e.g., reduction of particle agglomeration, reduction of macrophage phagocytosis, etc. When coupled with lung surfactant, a more efficient absorption of the compound can be achieved because surfactants, such as DPPC, will greatly facilitate diffusion of the compound. Surfactants are well known in the art and include but are not limited to phosphoglycerides, e.g., phosphatidylcholines, L-alpha-phosphatidylcholine dipalmitoyl (DPPC) and diphosphatidyl glycerol (DPPG); hexadecanol; fatty acids; polyethylene glycol (PEG); polyoxyethylene-9-; auryl ether; palmitic acid; oleic acid; sorbitan trioleate (Span 85); glycocholate; surfactin; poloxomer; sorbitan fatty acid ester; sorbitan trioleate; tyloxapol; and phospholipids.

IBD and Methods and Formulations Therefor

In one embodiment, a poly-PEGylated Kunitz domain that inhibits hNE is used to ameliorate at least one symptom of an inflammatory bowel disease, e.g., ulcerative colitis or Crohn's disease.

Inflammatory bowel diseases (IBD) are generally chronic, relapsing intestinal inflammation. IBD refers to two distinct disorders, Crohn's disease and ulcerative colitis (UC). Both diseases may involve either a dysregulated immune response to GI tract antigens, a mucosal barrier breach, and/or an adverse inflammatory reaction to a persistent intestinal infection (see, e.g., MacDermott, R. P., J Gastroenterology, 31:907:-916 (1996)).

In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. The clinical symptoms of IBD are intermittent rectal bleeding, crampy abdominal pain, weight loss and diarrhea. Diagnosis of IBD is based on the clinical symptoms, the use of a barium enema, but direct visualization (sigmoidoscopy or colonoscopy) is the most accurate test.

Symptoms of IBD include, for example, abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). A clinical index can also be used to monitor IBD such as the Clinical Activity Index for Ulcerative Colitis. See also, e.g., Walmsley et al. *Gut.* 1998 July; 43(1):29-32 and Jowett et al. (2003) Scand J Gastroenterol. 38(2):164-71.

In one embodiment, administration of the compound to a subject having or predisposed to having ulcerative colitis causes amelioration of the index, e.g., a statistically significant change in the index. The compound includes hNE inhibitor polypeptide that is physically associated with a moiety (e.g., a hydrophilic polymer)

In one embodiment, administration of the compound to a subject having or predisposed to having IBD causes amelioration of at least one symptom of IBD.

Crohn's disease, an idiopathic inflammatory bowel disease, is characterized by chronic inflammation at various sites in the gastrointestinal tract. While Crohn's disease most commonly affects the distal ileum and colon, it may manifest itself in any part of the gastrointestinal tract from the mouth to the anus and perianal area. The prognosis and diagnosis of Crohn's disease can be measured using a clinical index, e.g., Crohn's Disease Activity Index. See, e.g., American Journal of Natural Medicine, July/August 1997, and Best WR, et al., "Development of a Crohn's disease activity index." *Gastroenterology* 70:439-444, 1976. In one embodiment, administration of the compound to a subject having or predisposed to having Crohn's disease causes amelioration of the index, e.g., a statistically significant change in the index, or amelioration of at least one symptom of Crohn's disease.

Accordingly, in one aspect, the invention provides a composition that includes poly-PEGylated Kunitz domain that inhibits hNE for treatment of a bowel disease (e.g., a colitis such as ulcerative colitis, Crohn's disease or IBP) or other gastrointestinal or rectal disease. The composition can be formulated as a suppository. Suppositories can be formulated with base ingredients such as waxes, oils, and fatty alcohols with characteristics of remaining in solid state at room temperatures and melting at body temperatures. The active ingredients of this invention with or without optional therapeutic ingredients, like hydrocortisone (1.0%), topical anesthetics like benzocaine (1.0 to 6.0%) or others as already listed may be prepared at appropriate pH values; for example pH 5 liquid fatty alcohols, such as oleyl alcohol (range 45% to 65%) or solid higher fatty alcohols like cetyl or stearyl alcohol (30% to 50%). The base ingredients are well known in the art of this industry. See, e.g., U.S. Pat. Nos. 4,945,084 and 5,196,405.

The composition may also be used as an active ingredient in creams, lotions, ointments, sprays, pads, patches, enemas, foams and suppositories and others or in delivery vehicles such as micro-encapsulation in liposomes or glycospheres. Other delivery technologies include microsponges or the substitute cell membrane (Completech™) which entrap the active ingredients for both protection and for slower release. Rectal foams can be prepared as topical aerosol compositions may also be used, e.g., to treat (ulcerative colitis, Crohns colitis, and others).

Diagnostic Uses

A poly-PEGylated Kunitz domain has diagnostic utilities.

In one aspect, the present invention provides a diagnostic method for detecting the presence of a elastase protein, in vitro (e.g., a biological sample, such as tissue, biopsy or in vivo (e.g., in vivo imaging in a subject). The method includes: (i) contacting a sample with a poly-PEGylated Kunitz domain, e.g., a Kunitz domain that binds to a target protease, e.g., elastase, plasmin, or kallikrein; and (ii) detecting formation of a complex between the elastase ligand and the sample. The method can also include contacting a reference sample (e.g., a control sample) with the ligand, and determining the extent of formation of the complex between the ligand and the sample relative to the same for the reference sample. A change, e.g., a statistically significant change, in the formation of the complex in the sample or subject relative to the control sample or subject can be indicative of the presence of elastase in the sample.

Another method includes: (i) administering the compound to a subject; and (iii) detecting formation of a complex between the compound, and the target protease. The detecting can include determining location or time of formation of the complex.

The compound can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the compound and target protease can be detected by measuring or visualizing either the ligand bound to the target protease or unbound ligand. Conventional detection assays can be used, e.g., an enzyme-linked immunosorbent assays (ELISA), a radioimmunoassay (RIA) or tissue immunohistochemistry. Further to labeling the compound, the presence of target protease can be assayed in a sample by a competition immunoassay utilizing standards labeled with a detectable substance and an unlabeled protease ligand. In one example of this assay, the biological sample, the labeled standards and the compound are combined and the amount of labeled standard bound to the unlabeled ligand is determined. The amount of target protease in the sample is inversely proportional to the amount of labeled standard bound to the compound.

Fluorophore and chromophore labeled protein ligands can be prepared. A variety of suitable fluorescers and chromophores are described by Stryer (1968) *Science,* 162:526 and Brand, L. et al. (1972) *Annual Review of Biochemistry,* 41:843-868. The protein ligands can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein ligand can be used to detect the presence or localization of the a target protease in a sample, e.g., using fluorescent microscopy (such as confocal or deconvolution microscopy).

Protein Arrays. The compound can also be immobilized on a protein array. The protein array can be used as a diagnostic tool, e.g., to screen medical samples (such as isolated cells, blood, sera, biopsies, and the like). Methods of producing polypeptide arrays are described, e.g., above.

In vivo Imaging. In still another embodiment, the invention provides a method for detecting the presence of a target protease or a target protease-expressing tissue in vivo. The method includes (i) administering to a subject (e.g., a patient having a pulmonary or respiratory disorder) a compound that includes a Kunitz domain and that is polyPEGylated, conjugated to a detectable marker; (ii) exposing the subject to a means for detecting said detectable marker to the target protease-expressing tissues or cells. For example, the subject is imaged, e.g., by NMR or other tomographic means.

Examples of labels useful for diagnostic imaging in accordance with the present invention include radiolabels such as $^{131}I$, $^{111}In$, $^{123}I$, $^{99m}Tc$, $^{32}P$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed. The compound that includes the Kunitz domain can be labeled with such reagents using known techniques. For example, see Wensel and Meares (1983) *Radioimmunoimaging and Radioimmunotherapy,* Elsevier, New York for techniques relating to the radiolabeling of proteins and D. Colcher et al. (1986) *Meth. Enzymol.* 121: 802-816.

A radiolabeled compound of this invention can also be used for in vitro diagnostic tests. The specific activity of an isotopically-labeled compound depends upon the half-life, the isotopic purity of the radioactive label, and how the label is incorporated into the compound.

Procedures for labeling polypeptides (e.g., the polypeptide portion of the compound) with the radioactive isotopes (such as $^{14}C$, $^{3}H$, $^{35}S$, $^{125}I$, $^{32}P$, $^{131}I$) are generally known. For example, tritium labeling procedures are described in U.S. Pat. No. 4,302,438. Iodinating, tritium labeling, and $^{35}S$ labeling procedures, e.g., as adapted for murine monoclonal antibodies, are described, e.g., by Goding, J. W. (*Monoclonal antibodies: principles and practice: production and application of monoclonal antibodies in cell biology, biochemistry, and immunology* 2nd ed. London; Orlando: Academic Press, 1986. pp 124-126) and the references cited therein. Other procedures for iodinating polypeptides, are described by Hunter and Greenwood (1962) *Nature* 144:945, David et al. (1974) *Biochemistry* 13:1014-1021, and U.S. Pat. Nos. 3,867, 517 and 4,376,110. Radiolabeling elements which are useful in imaging include $^{123}I$, $^{131}I$, $^{111}In$, and $^{99m}Tc$, for example. Procedures for iodinating polypeptides are described by Greenwood, F. et al. (1963) *Biochem. J.* 89:114-123; Marchalonis, J. (1969) *Biochem. J.* 113:299-305; and Morrison, M. et al. (1971) *Immunochemistry* 289-297. Procedures for $^{99m}Tc$-labeling are described by Rhodes, B. et al. in Burchiel, S. et al. (eds.), *Tumor Imaging: The Radioimmunochemical Detection of Cancer*, New York: Masson 111-123 (1982) and the references cited therein. Procedures suitable for $^{111}In$-labeling antibodies are described by Hnatowich, D. J. et al. (1983) *J. Immul. Methods*, 65:147-157, Hnatowich, D. et al. (1984) *J. Applied Radiation*, 35:554-557, and Buckley, R. G. et al. (1984) *F.E.B.S.* 166:202-204.

In the case of a radiolabeled compound, the compound is administered to the patient, is localized to the tissue the antigen with which the compound interacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 µm to about 10 nM in diameter). Particles can have ferromagnetic, antiferromagnetic or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like.

The compounds can also be labeled with an indicating group containing of the NMR-active $^{19}F$ atom, or a plurality of such atoms inasmuch as (i) substantially all of naturally abundant fluorine atoms are the $^{19}F$ isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) *Scientific American*, 246:78-88 to locate and image cancerous tissues.

Also within the scope of the invention are kits comprising the compound that binds to a target protease and instructions for use, e.g., the use of the compound (e.g., poly-PEGylated Kunitz domain) to detect the target protease, in vitro, e.g., in a sample, e.g., a biopsy or cells from a patient having a pulmonary disorder, or in vivo, e.g., by imaging a subject. The kit can further contain a least one additional reagent, such as a label or additional diagnostic agent. For in vivo use the compound can be formulated as a pharmaceutical composition.

An exemplary amino acid sequence of a human neutrophil elastase: (Also listed in GenBank® under: gi|4503549|ref|NP_001963.1| elastase 2, neutrophil [*Homo sapiens*])

```
                                            (SEQ ID NO:22)
MTLGRRLACLFLACVLPALLLGGTALASEIVGGRRARPHAWPFMVSLQLR

GGHFCGATLIAPNFVMSAAHCVANVNVRAVRVVLGAHNLSRREPTRQVFA

VQRIFENGYDPVNLLNDIVILQLNGSATINANVQVAQLPAQGRRLGNGVQ

CLAMGWGLLGRNRGIASVLQELNVTVVTSLCRRSNVCTLVRGRQAGVCFG

DSGSPLVCNGLIHGIASFVRGGCASGLYPDAFAPVAQFVNWIDSIIQRSE

DNPCPHPRDPDPASRTH
```

The following non-limiting examples further illustrate aspects of the invention:

EXAMPLE

Peptides and small proteins are rapidly cleared from circulation in vivo. The rapid clearance often greatly limits therapeutic potency. High doses and frequent administration are needed to achieve therapeutic effects.

DX-890 consists of 56 amino acids, contains three intramolecular disulfide bonds, and has a molecular weight of 6,237 Da. For primary amine-based coupling, there are five potential PEGylation sites on DX-890, each of the four lysine residues and the N-terminus. Use of mPEG succinimidyl propionic acid can be used to couple PEG to each of these sites, e.g., at four lysine residues and the N-terminus. The PEG reagent that can be used may be mPEG that has an average molecular weight of about 5 kDa.

The reaction can be allowed to proceed to completion at a pH that permits modification of the amino groups on the lysine side chains and to the N-terminus. For example, the pH can be greater than 7.5, e.g., between 7.8 and 8.5. The reaction is quenched, e.g., with Tris. The reaction can be loaded onto an ion exchange or size exclusion column and fractions that contain PEGylated DX-890 are collected. These relevant fractions can be dialyzed, further purified, and then stored or analyzed.

DX-1000, a human plasmin inhibitor, is a Kunitz domain with fewer lysines than DX-890. It has a three available lysines and an N-terminus for modification with mPEG. DX-1000 can be combined with an mPEG succinimidyl propionic acid reagent having an average molecular weight of about 5 kDa or 7 kDa. DX-1000 can be modified and purified, e.g., as described for DX-890. U.S. Pat. No. 6,103,499 also describes other plasmin inhibitors, including DX-1000 related inhibitors. Kunitz domains having sequences or conforming to motifs described in U.S. Pat. No. 6,103,499 can be modified as described herein.

DX-88, a kallikrein inhibitor is a Kunitz domain with fewer lysines than DX-890. It has a three available lysines and an N-terminus for modification with mPEG. DX-88 can be combined with an mPEG succinimidyl propionic acid reagent having an average molecular weight of about 5 kDa or 7 kDa. DX-88 can be modified and purified, e.g., as described for DX-890. U.S. Pat. No. 6,333,402 also describes other kallikrein inhibitors, including DX-88 related inhibitors. See, e.g., Tables 6 and 103 described therein. Kunitz domains having sequences or conforming to motifs described in U.S. Pat. No. 6,333,402 can be modified as described herein.

Figure 2:
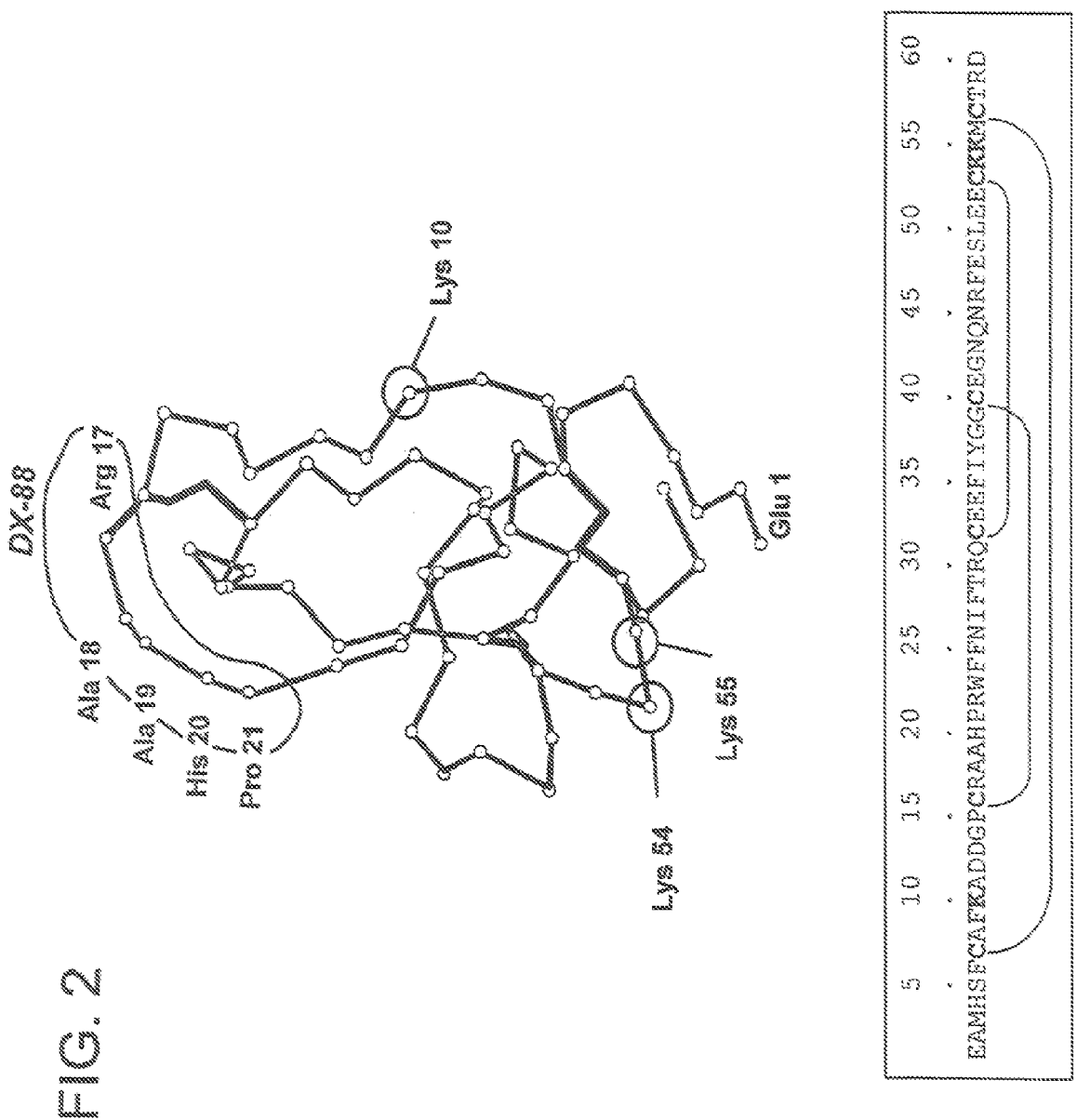
FIG. 2 depicts the structure of DX-88 (SEQ ID NO:24) and the position of its three lysine residues.
Figure 3:
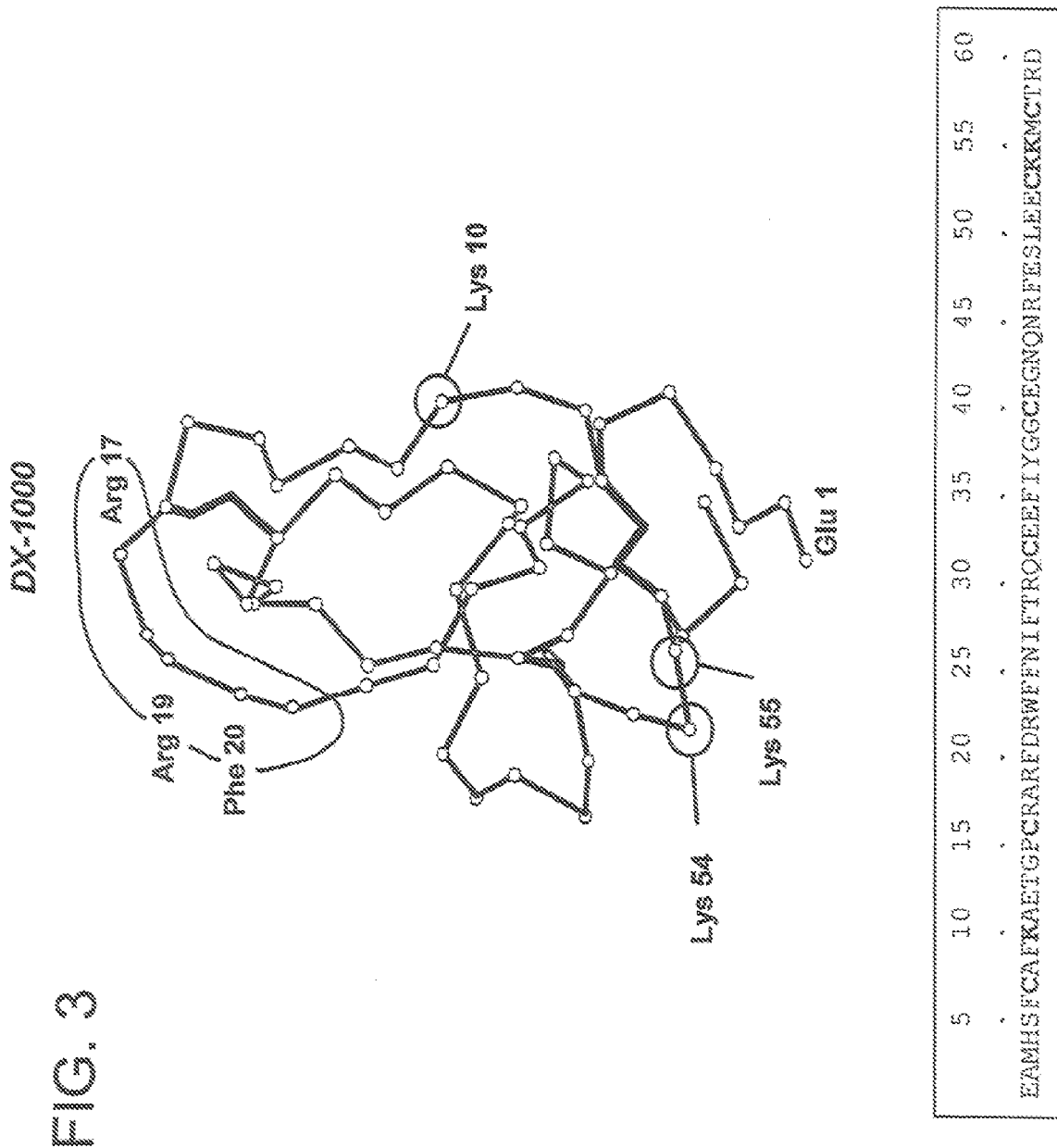
FIG. 3 depicts the structure of DX-1000 (SEQ ID NO:25) and the position of its three lysine residues.
Figure 4:
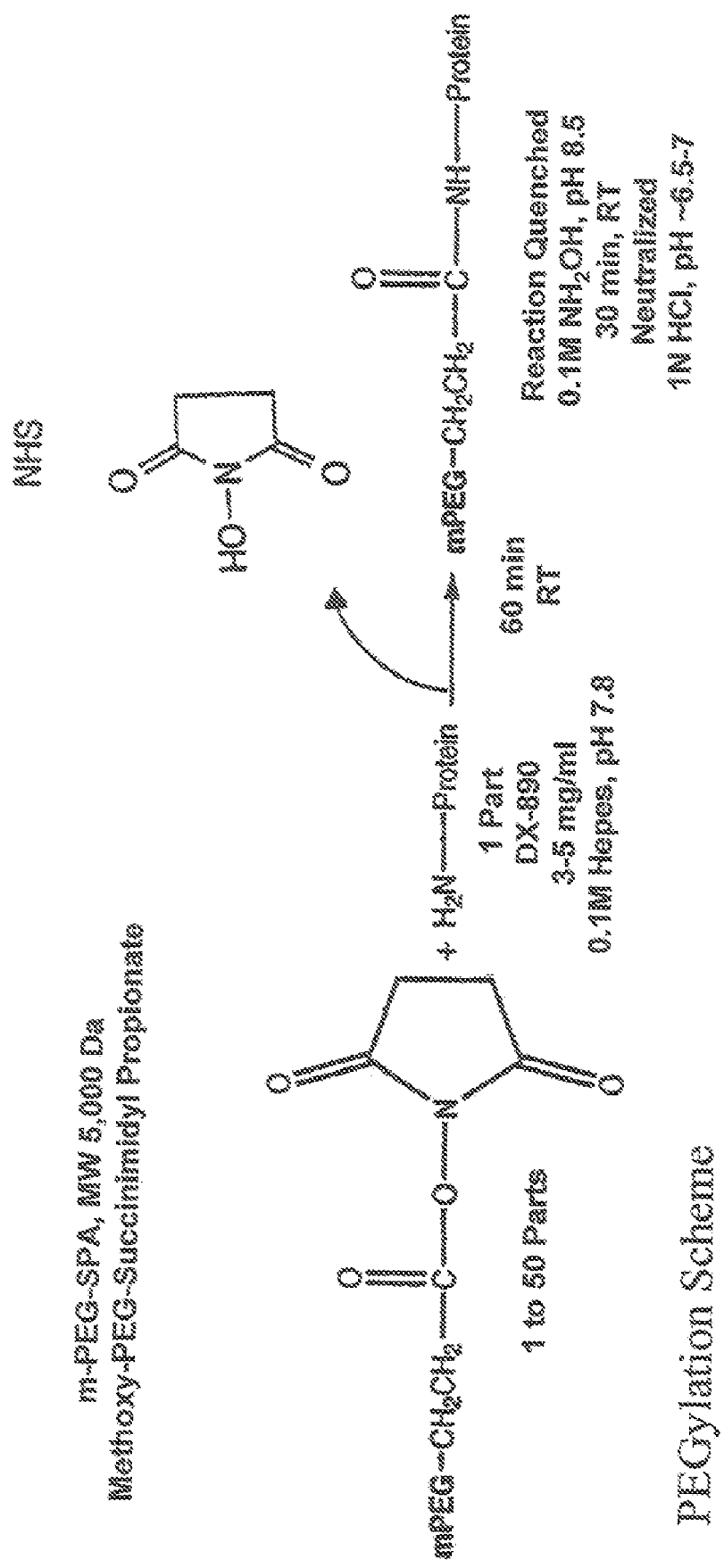
FIG. 4 is an exemplary PEGylation scheme. The reaction pH can be run at a pH of between 7.8 and 8.5.
Figure 5:
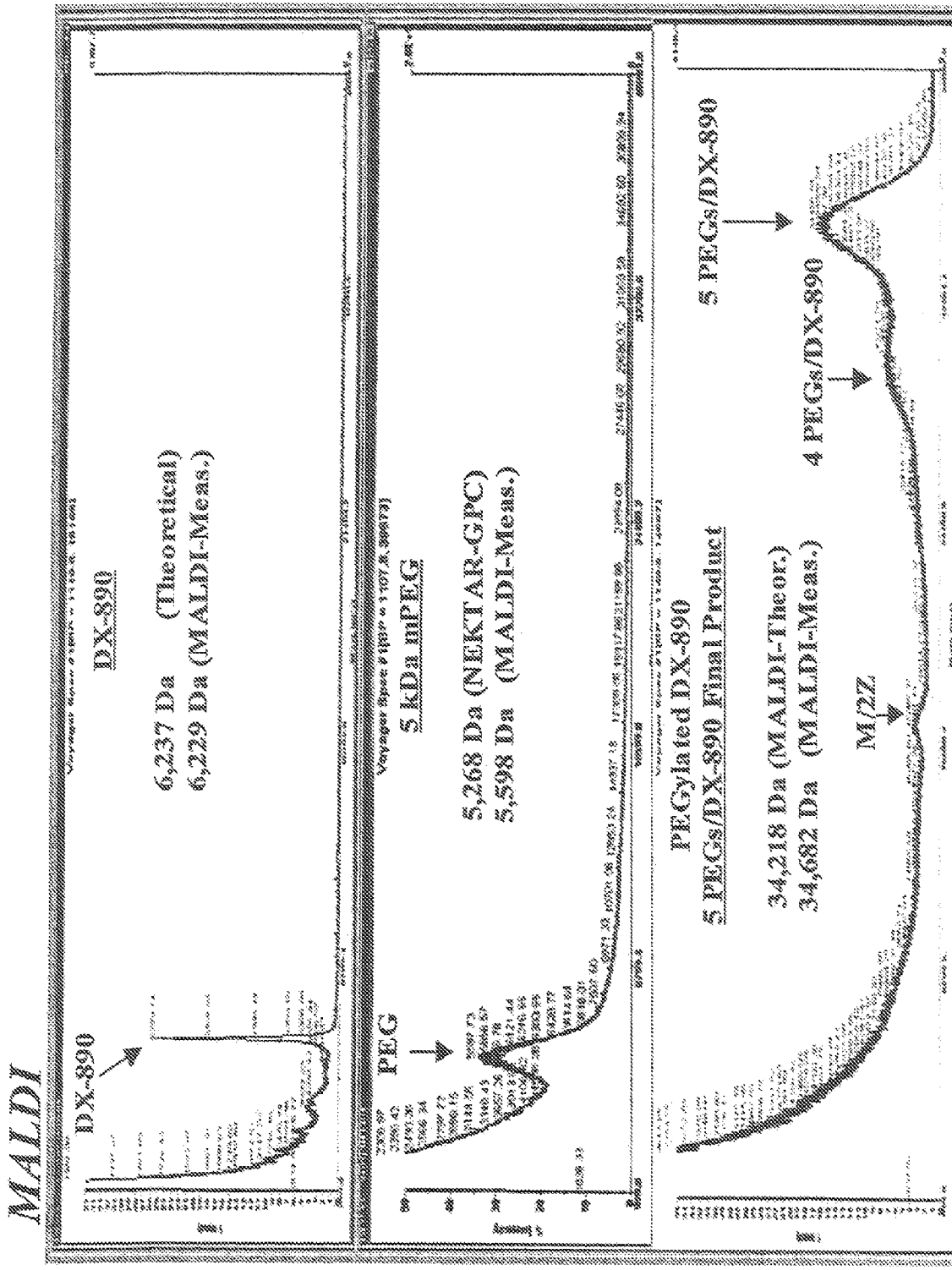
FIG. 5 shows results of an exemplary MALDI analysis.
Figure 6A:
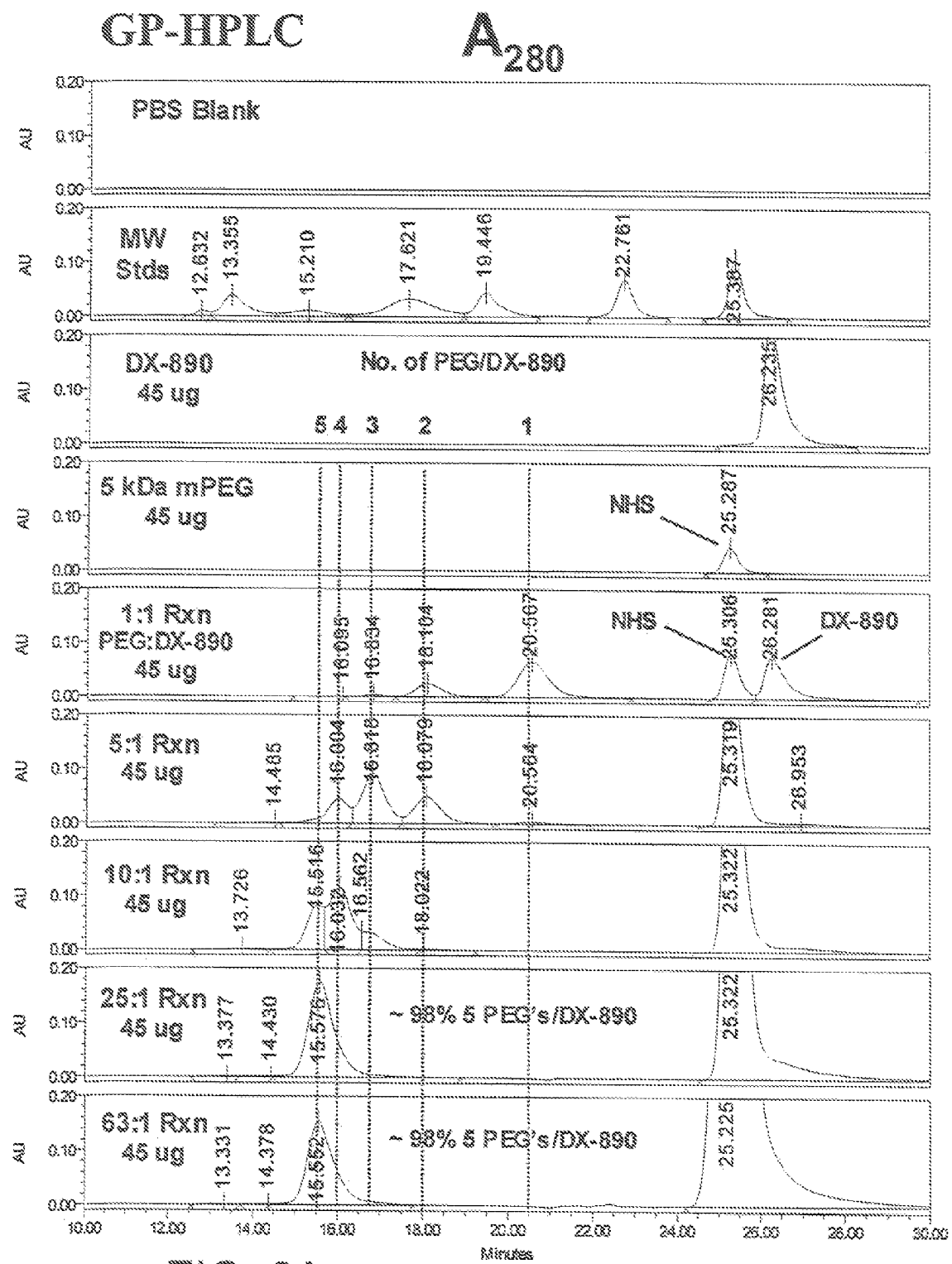
FIG. 6 shows results of exemplary GP-HPLC runs.
Figure 6B:
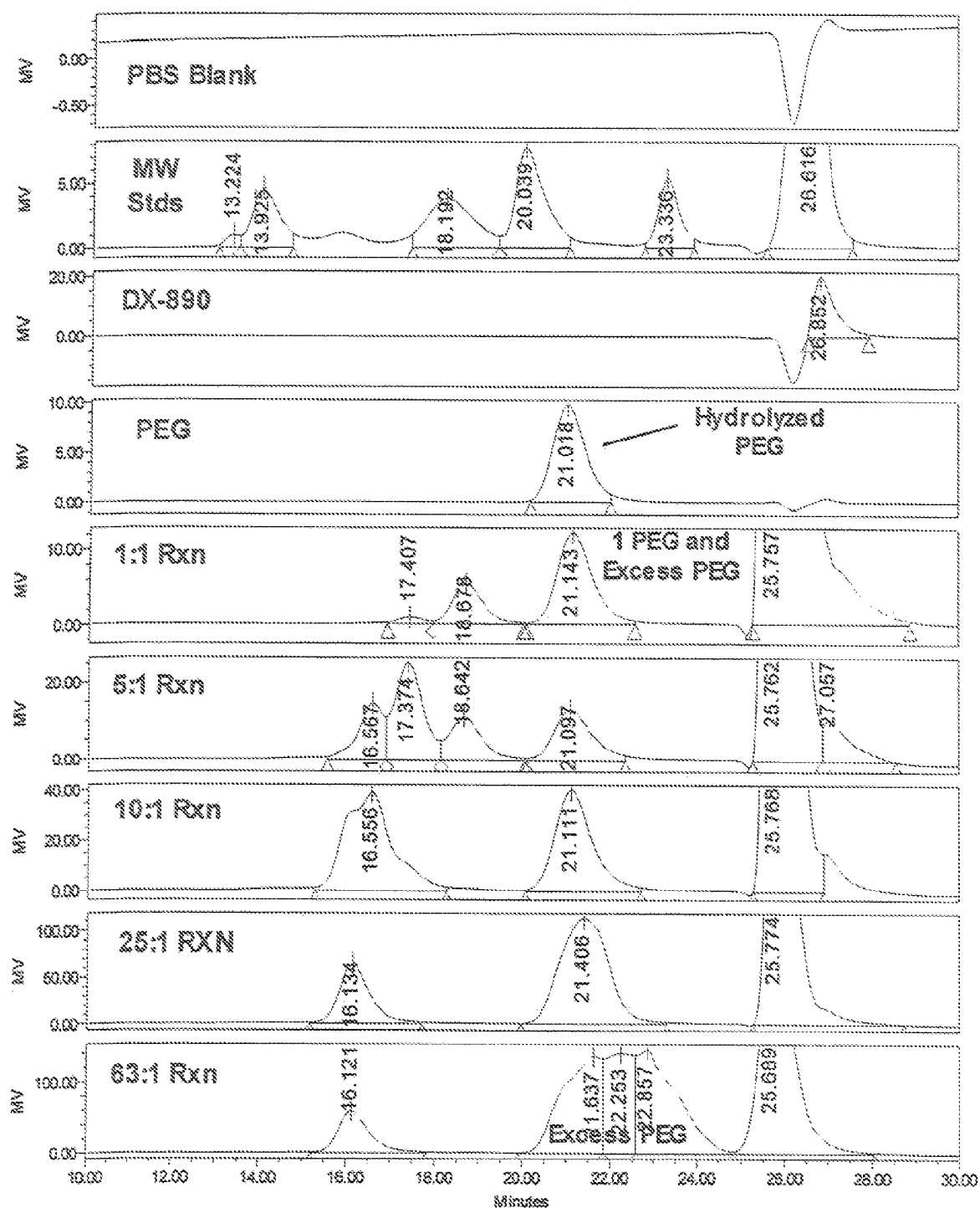
Figure 7:
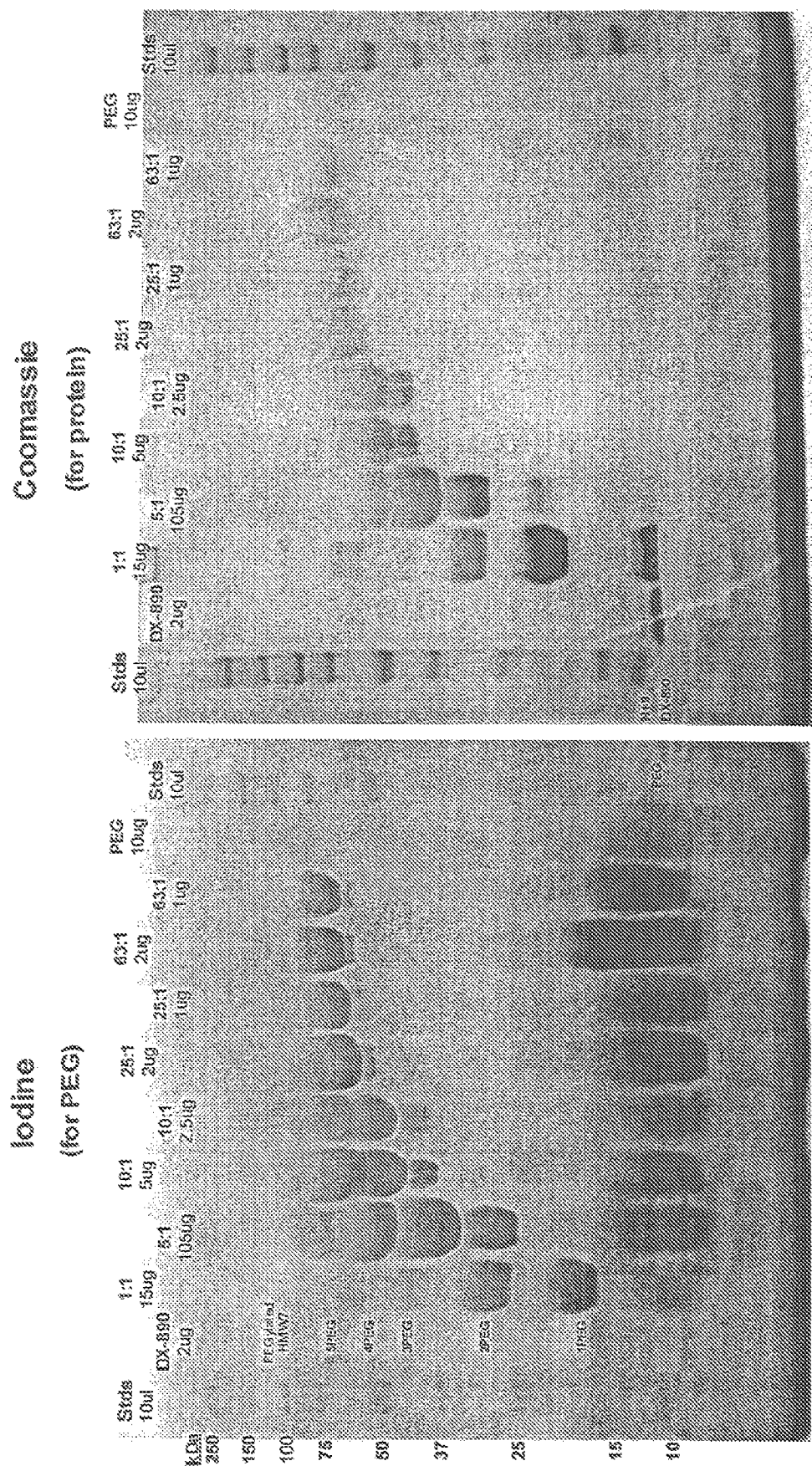
FIG. 7 shows exemplary results of SDS-PAGE analysis.
Figure 8A:
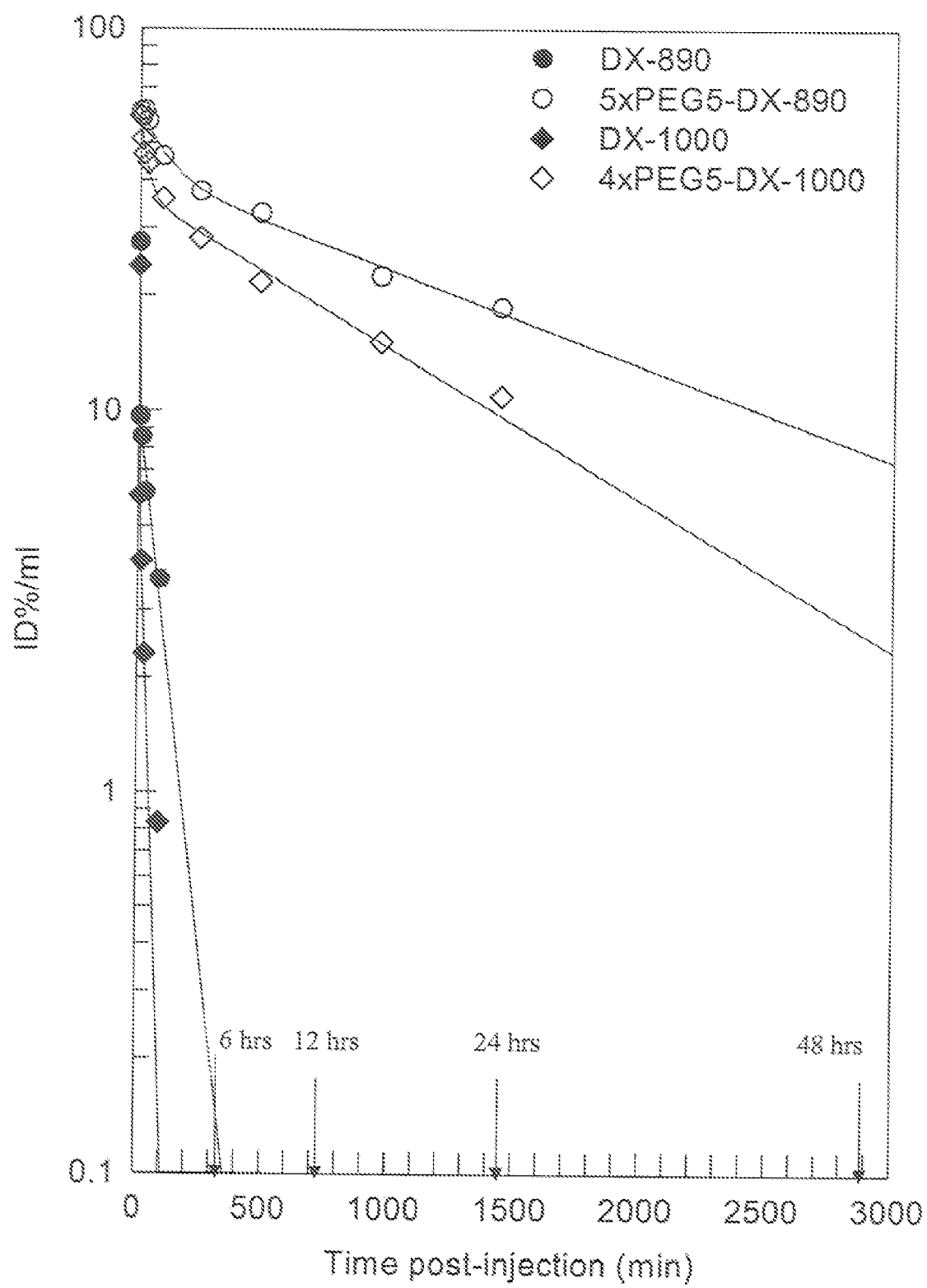
FIG. 8*a* shows exemplary results of clearance studies in mice and 8*b* shows clearance studies in rabbits. The data were plotted using a double 4-parameter exponential decay.
Figure 8B:
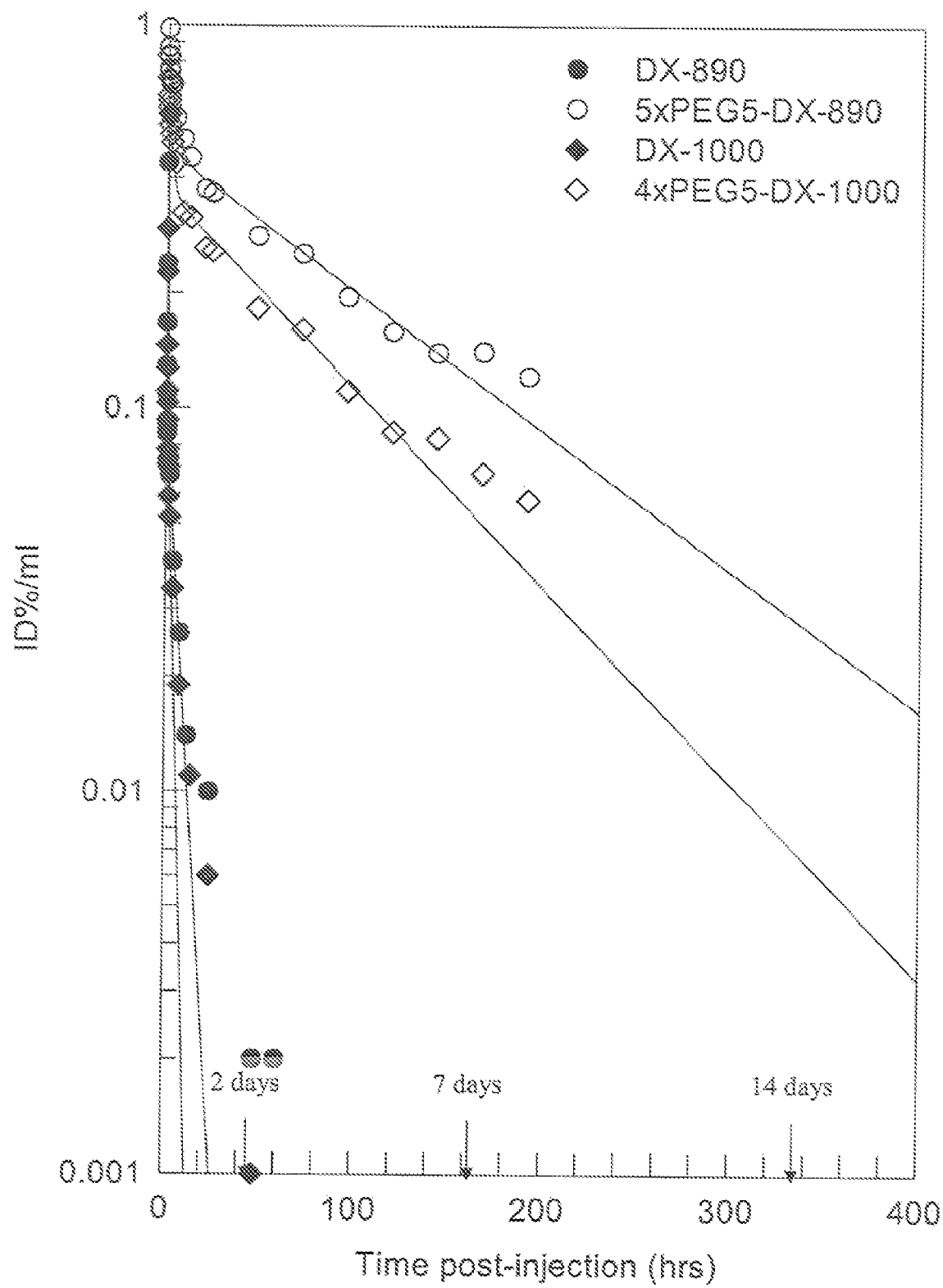
FIG. 8*c* shows an allometric extrapolation to humans. Extrapolated values for long half life clearance phase in a 70 Kg human were as follows: DX-890, 8.4 hours; 5-PEG5-DX-890, 330 hours, or about 14 days; DX-1000, 1.7 hours; 4-PEG5-DX-1000, 210 hours, or about 9 days.
Figure 8C:
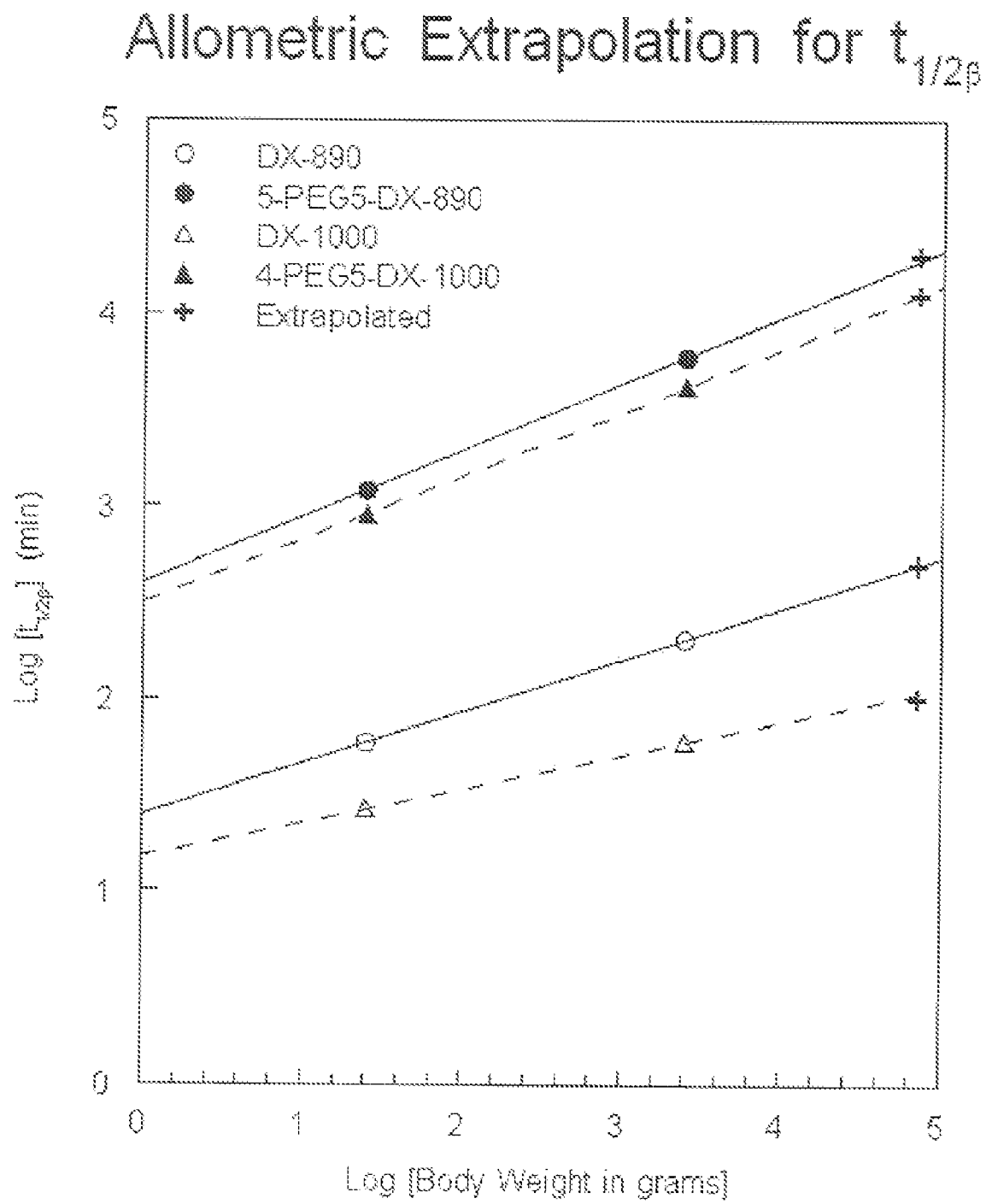

The predicted or actual structures of DX-890, DX-88, and DX-1000 are shown with the lysine residues indicated in FIGS. 1, 2, and 3, respectively.

EXAMPLE

The Example above is further detailed by the following methods for PEGylating a protein of interest at multiple or all possible reactive sites, in the following implementations, the method is used to poly-PEGylate Kunitz domains at multiple or all possible primary amines.

A 5 kDa amino-reactive monofunctional PEG (mPEG-SPA) from NEKTAR Therapeutics (cat. no.: 2M4M0H01) was used as material of the PEGylation reactions.

We found that it is possible to poly-PEGylate DX-88, DX-890 and DX-1000 with four or five 5 kDa PEGs. Moreover, the poly-PEGylated proteins maintained the desired therapeutic activity while having increased circulating half-life. Additionally, reaction conditions were very efficient in terms of the conversion of unmodified protein to the desired PEGylated form. The reactions can be used, or scaled up, to provide consistently homogenous preparations of poly-PEGylated product. Because of this great efficiency and few reaction side products, preparations of the poly-PEGylated products can be synthesized with higher yield and lower cost than Kunitz domains that include a single PEG moiety. This approach makes for easier manufacturability with more controlled batch-to-batch consistency and a final product which is easier to fully characterize.

Materials
  mPEG-SPA, MW 5,000 Da, NEKTAR Therapeutics, cat. no.: 2M4M0H01 (succinimidyl ester of methoxy-capped polyethylene glycol propionic acid)
  DX-88 API, MW 7,054 Da, ~10 mg/ml in PBS, pH 7.0
  DX-890 API, MW 6,231 Da, ~10 mg/ml in 10 mM NaAc, pH 3.0
  DX-1000 API, MW 7,167 Da, ~10 mg/ml in PBS, pH 7.0
  0.2-0.3M Hepes, pH 7.8-8.5
  1M Tris, pH 8.0
  1N HCl PEGylation Reaction I:
1) Calculate the amount of PEG needed for reacting the Kunitz domain polypeptide at approximately 10:1 molar ratio of PEG:reactive group. For example, DX-890 has 5 total reactive groups, so a 50:1 molar ratio of PEG:DX-890 is used. Depending upon the Kunitz domain polypeptide and/or reaction conditions, a ratio of 25:1 to 50:1 is typically used. For example, for PEGylating 10 mg of DX-890 (MW 6,231 Da) at a 50:1 molar ratio of PEG:peptide, 401 mg of PEG (MW 5,000 Da) would be used.
2) Just prior to reacting the Kunitz domain polypeptide with the PEG, dilute the required volume of Kunitz domain polypeptide stock 1:1 with 0.2M Hepes, pH 7.8-8.5 buffer. The peptide stock is typically ~10.0 mg/ml. Therefore upon dilution, the concentration of the Kunitz domain polypeptide is ~5.0 mg/ml in 0.1M Hepes, pH 7.8-8.5 buffer. Both DX-88 and DX-1000 are relatively stable in terms of solubility upon dilution. DX-890, while initially soluble upon dilution, however, may precipitate over time. Reaction times can be chosen to minimize precipitation.
3) Immediately add the 1:1 diluted Kunitz domain polypeptide solution directly to the PEG powder and quickly dissolve the PEG by vortexing. Once completely dissolved, cap the tube, wrap in foil and allow to react while slowly rocking/tumbling for 2.5-3 hours at 2-8° C. to 25° C.
4) Quench the reaction by adding $\frac{1}{8}^{th}$. volume of 1 M Tris, pH 8.0 for 30-60 minutes at 2-8° C. to 25° C. while slowly rocking/tumbling.
5) Carefully and slowly adjust the pH of the quench reaction mixture to ~ pH 7 with small additions of 1N HCl while mixing.
6) The neutralized reaction can be stored at 2-8° C. or frozen at −20° C. to −80° C. until purification.

The direct addition of the Kunitz domain polypeptide solution to PEG powder can help simplify the number of steps in the reaction process and reduce hydrolysis prior to reaction.

PEGylation Reaction II:
The following is another method for poly-PEGylating a polypeptide.
1) PEG is weighed out, as described for Reaction I, and placed aside for use just prior to reaction.
2) Dilute the Kunitz domain polypeptide to 3-5 mg/ml in 0.3M Hepes, pH 7.8-8.5.
3) Just prior to reaction, quickly prepare a 200-250 mg/ml solution of PEG (in slight excess) in dH$_2$O that has been previously degassed and N$_2$-saturated. Add the water to the PEG and quickly and completely dissolve by vortexing.
4) Immediately add the required volume of PEG solution to the Kunitz domain polypeptide solution while mixing. Cap the tube, wrap in foil and allow to react while slowly rocking/tumbling for 2.5-3 hours at 2-8C to 25C.
5) Continue with steps 4) through 6) above.

EXAMPLE

Analytical Methods

Modified Kunitz domains can be analyzed and characterized by a variety of methods. Exemplary methods include the following:

The unpurified reaction mix may be analyzed for the extent of PEGylation by both reducing/non-reducing SDS-PAGE analysis with both Coomassie and iodine staining as described in a separate protocol and size-exclusion high performance liquid chromatography (SEC-HPLC) by monitoring both refractive index (RI) and absorbance at 280 nm (UV). The SDS-PAGE analysis by Coomassie stain detects only the polypeptide component of the reaction mix (free and coupled) whereas staining with iodine preferentially detects the PEG (free and coupled). SEC-HPLC analysis by UV (abs. 280 nm) detects the peptide (free and coupled) and RI detects both peptide and PEG. Dynamic light scattering (LS) detection allows for determination of absolute MW and MW distribution.

SDS-PAGE and SEC-HPLC can show the distribution of PEGylated products, but the absolute molecular weights should be determined by MALDI-TOF or other methods. The reason is that PEGylated proteins run more slowly on gels and SEC-HPLC than do unPEGylated proteins, due to the PEG moieties large hydrodynamic radius, leading to overestimation of molecular weight. This could be overcome by using PEGylated Kunitz domains of known absolute molecular weight as standards.

Iodine Staining

Gels are loaded with approximately 2-3 μg of protein initially (for DX-1000, DX-88, and DX-890) for PEGylated samples that will resolve into one or two bands only. This loading is most often appropriate for the 25:1 and 50:1 PEG:protein reactions if the coupling was successful. However, for samples that were PEGylated at the lower reaction ratios (1:1, 5:1, and 10:1) and are expected to exhibit multiple PEGylated species, 10-15 μg of protein per lane is more appropriate (since 4-5 bands may appear). Samples are mixed with the appropriate amount of NuPAGE LDS Sample Buffer. Samples are vortexed and heated at 70° C. for 10 minutes prior to loading.

Gels can be prepared and resolved according to standard methods, e.g. using the Invitrogen NuPAGE system with a 4-12% Bis-Tris gels. See, e.g., NuPAGE Novex Bis-Tris Gels Quick Reference Card, Invitrogen Life Technologies.

Gels are rinsed briefly in deinoized water, then covered with a 5% barium chloride solution for 10 minutes on the shaker. The gel is rinsed again with deinoized water and then immersed in a 0.1N Iodine solution for at least 10 minutes on the shaker. Bands should be visible almost immediately. Full staining will be complete after 10 minutes. The gel is then photographed, for example, with UVP Epi Chem II Darkroom and the Ethidium bromide filter.

After iodine staining, the protein can be stained for proteins with Coomassie. The gel is first rinsed in water to destain then mixed with Coomassie and then destained in 300 mL methanol, 100 mL glacial acetic acid, and 600 mL water. UnPEGylated protein bands appear dark blue, and PEGylated protein may appear very light blue, if at all.

Chromatography

The chromatography system (Waters Corporation) used here was the 600 system (pump/controller) running EMPOWER™ software with 717 plus auto sampler, 996 photodiode array detector (PDA) and 2414 refractive index detector. In addition, a PD2010+ dynamic light scattering (LS) detector (Precision Detectors, Inc.) was also run in series.

SEC column chromatography can include the following features: SEC column: TSK G3000SW$_{x1}$ (7.8 mm ID×30 cm L) with guard (Tosoh Bioscience, cat. no.: 08541 and 08543); Flowrate: 0.5 ml/minute; Run time: 35 minutes; Mobile phase: PBS, pH 7.2 with 0.05% NaN$_3$; Sample injection volume: 25-100 μL; Sample load: 50-100 μg per injection; Detection: UV (280 nm), RI and LS; SEC Standards: BioRad, cat. no.: 151-1901

MALDI-TOF

MALDI-TOF (matrix-assisted laser desorption ionization-time of flight) Mass Spectrometry (ABI, Applied Biosystems Voyager-DE) can be used to evaluate actual mass of reaction products and subjects. For polypeptide analysis (e.g., prior to reaction), alpha-cyano-4-hydroxycinnamic acid can be used as a matrix. For analysis of reaction products or poly-PEGylated speices, 2,5-dihydroxybenzoic acid (DHB) can be used as a matrix. Chips can be spotted 1:1 (0.5 μL:0.5 μL) of sample:matrix, and air dried prior to analysis Ki Measurement The equilibrium inhibition constants (Ki) for a poly-PEGylated protein (e.g., a poly-PEGylated DX-890) can be determined according to the tight-binding inhibition model with formation of a reversible complex (1:1 stoichiometry). Reactions are set up with 100 pM enzyme (e.g., elastase) and a range of inhibitor concentrations (0-4 nM) at 30° C. in 50 mM HEPES, pH 7.5, 150 mM NaCl, and 0.1% Triton X-100. Following a 24 h incubation, substrate is added (25 μM) to the enzyme-inhibitor solution and the rate of substrate hydrolysis is monitored at an excitation of 360 nm and an emission of 460 nm. Plots of the percent remaining activity versus active inhibitor concentration are fit by nonlinear regression analysis to Equation 1 to determine equilibrium dissociation constants. Unmodified protein and poly-PEGylated protein can be analyzed for comparison.

$$\%A = 100 - \left( \frac{(I+E+K_i) - \sqrt{(I+E+K_i)^2 - 4 \cdot E \cdot I}}{2 \cdot E} \right) \cdot 100 \qquad \text{Equation 1}$$

Where:
% A=percent activity
I=Kunitz domain protein concentration (e.g., DX-890)
E=enzyme (e.g., HNE) concentration
$K_i$=equilibrium inhibition constant Pharmacokinetics in Animals The following methods can be used to evaluate the pharmacokinetics (PK) of proteins such as poly-PEGylated proteins in animals, e.g., mice and rabbits. The protein to be tested is labeled with iodine ($^{125}$I) using the iodogen method (Pierce). The reaction tube is rinsed with reaction buffer (25 mM Tris, 0.4 M NaCl, pH 7.5). The tube is emptied and then replaced with 0.1 ml of reaction buffer and 12 μl of carrier free iodine-126, about 1.6 mCi. After six minutes, the activated iodine is transferred to a tube containing the protein to be tested. After nine minutes, the reaction is terminated with 25 μl of saturated tyrosine solution. The reaction can be purified on a 5 ml D-salt polyacrylamide 6000 column in Tris/NaCl. HSA can be used to minimize sticking to the gel.

A sufficient number of mice (about 36) are obtained. The weight of each animal is recorded. In the case of mice, the animals are injected in the tail vein with about 5 μg of the protein to be tested. Samples are recovered at each time point per animal, with four animals per time point, at approximately 0, 7, 15, 30, and 90 minutes, 4 hours, 8 hours, 16 hours, and 24 hours post injection. Samples (about 0.5 ml) are collected into anti-coagulant (0.02 ml EDTA). Cells are spun down and separated from plasma/serum. Samples can be analyzed by radiation counting and SEC peptide column on HPLC with inline radiation detection.

For rabbits, the material is injected into the ear vein. Samples can be collected at 0, 7, 15, 30, 90 minutes, 4, 8, 16, 24, 48, 72, 96, 120, and 144 hours post-injection. Samples can be collected and analyzed as for mice.

Data can be fit to a bi-exponential (equation 2) or a tri-exponential (equation 3) decay curve describing "fast", "slow", and "slowest" phases of in vivo clearance:

$$y = Ae^{-\alpha t} + Be^{-\beta t} \qquad \text{Equation 2}$$

$$y = Ae^{-\alpha t} + Be^{-\beta t} + Ce^{-\gamma t} \qquad \text{Equation 3}$$

Where:
y=Amount of label remaining in plasma at time=t post-administration
A=Total label in "fast" clearance phase
B=Total label in "slow" clearance phase
C=Total label in "slowest" clearance phase
α="Fast" clearance phase decay constant
β="Slow" clearance phase decay constant
γ="Slowest" clearance phase decay constant
t=Time post administration The α, β, and γ phase decay constants can be converted to half-lives for their respective phases as:

α Phase Half-life=0.69 (1/α)

β Phase Half-life=0.69 (1/β)

γ Phase Half-life=0.69 (1/γ)

In the case where the data are fit using the bi-exponential equation, the percentages of the total label cleared from in vivo circulation through the α and β phases are calculated as:

% α Phase=[A/(A+B)]×100

% β Phase=[B/(A+B)]×100

In the case where the data are fit using the tri-exponential equation, the percentages of the total label cleared from in vivo circulation through the α and β phases are calculated as:

% α Phase=[A/(A+B+C)]×100

% β Phase=[B/(A+B+C)]×100

% γ Phase=[C/(A+B+C)]×100

TABLE 4

Plasma Clearance in Mice

|  | $T_{1/2\ alpha}$ (min.) | Clearance (%) | $T_{1/2\ beta}$ (min.) | Clearance (%) |
| --- | --- | --- | --- | --- |
| DX-890 | 1.3 | 79 | 59.2 | 21 |
| DX-1000 | 1.5 | 87 | 26.9 | 13 |

|  | $T_{1/2\ alpha}$ (hrs.) | Clearance (%) | $T_{1/2\ beta}$ (hrs.) | Clearance (%) |
| --- | --- | --- | --- | --- |
| 5 × PEG5-DX-890 | 1.1 | 33 | 20.2 | 67 |
| 4 × PEG5-DX-1000 | 0.3 | 38 | 12.5 | 62 |

TABLE 5

Plasma Clearance in Rabbit

|  | $T_{1/2\ alpha}$ (min.) | Clearance (%) | $T_{1/2\ beta}$ (hrs.) | Clearance (%) | $T_{1/2\ gamma}$ (hrs.) | Clearance (%) |
| --- | --- | --- | --- | --- | --- | --- |
| DX-890 | 1.7 | 83 | 3.4 | 17 |  |  |
| DX-1000 | 0.9 | 85 | 1 | 15 |  |  |
| 5 × PEG5-DX-890 | 2.8 | 28 | 4.5 | 34 | 97.6 | 38 |
| 4 × PEG5-DX-1000 | 1.9 | 34 | 3 | 32 | 69.3 | 34 |

In the case of both the mouse (Table 4) and rabbit (Table 5), PEGylation of either DX-890 or of DX-1000 results in a decrease in the fraction of clearance through the alpha pathway. At the same time the fraction of clearance through the longer lived pathways (beta and gamma) increases.

The poly-PEGylated proteins also showed good in vivo stability by SEC analysis.

Purification:
One exemplary purification method is as follows:
1) Purification of polyPEGylated-protein from excess/unreacted PEG and trace amounts of both high molecular weight and lower molecular weight PEGylated species may be accomplished by ion-exchange chromatography on an AKTA Basic 10/100 chromatography system (Amersham).
2) For example, a column of appropriate size and capacity may be packed with a strong cation exchange resin (i.e.: Poros 50HS, Applied Biosystems, prod. code: 1-3359-11) in the case of at least PEGylated DX-88 and DX-1000.

3) Briefly, a volume of the PEGylation reaction mix is diluted 5-15 fold or as necessary, with water followed by pH adjustment to pH~3.0 with 1 M acetic acid (100-200 mM final) and conductivity <3 mS/cm.
4) The column is first equilibrated with 100 mM acetic acid, pH 3.0. Linear flowrate of 100 cm/hr.
5) Loaded and washed with same for ~5 column volumes. Linear flowrate during loading is 50 cm/hr.
6) The PEGylated protein is eluted from the column in a series of step gradients.
7) The first step elution is 100 mM acetic acid, with 20 mM NaCl, pH 3.2 to help remove HMW components (~20 CV at 100 cm/hr).
8) The second step elution is 100 mM acetic acid with 50 mM NaCl, pH 3.8 (~10 CV at 100 cm/hr) elutes the main product (i.e.: 4×5 kDa PEG/peptide for DX-88 and DX-1000).
9) The third and final step elution is PBS, pH 7.2 (~5 CV 100 cm/hr) to help remove trace amounts of LMW PEGylated species.
10) Followed by 0.2M NaOH cleaning (~5 CV with contact time of 30 minutes).
11) Followed by column storage in 20% ethanol (~10 CV).
12) Fractions are collected across the profile and analyzed by SDS-PAGE prior to pooling.
13) The final pool of purified PEGylated protein is then UF/DF into PBS, pH 7.2 using conventional means available. The final material is then 0.22 um filtered, quantitated by abs. 280 nm (as previously described), aliquoted and frozen at −20° C. to −80° C. until use.

Another exemplary purification method, and one that can be used to purify poly-PEGylated DX-88, is as follows.

Reaction products are loaded on a cation exchange column. Poros 50HS was found to have a fair binding capacity (~3 mg DX88-PEG5K/ml resin) at this small scale that would allow for separation of free PEG and a fairly concentrated eluate that includes the poly-PEGylated species. Conductivity can be maintained below 2 mS/cm. For example, a 9.5 cm AKTA Poros 50HS column (1.1 cm w.×10 cm h.) can be used. The column is washed and cleaned to remove endotoxin and other contaminants. The column can be equilibrated and loaded in 10 mM sodium acetate pH 3.5.

UF/DF and Final DX-88-PEG5K Pool Analysis

Fractions containing poly-PEGylated DX-88 were pooled for a total sample volume of ~6 mL. The sample was buffer exchanged into 1xDPBS pH 7.2 (unmodified) from Invitrogen (endotoxin specification <0.25 EU/ml) and concentrated using two Amicon Ultra-15 Centrifugal Filter Devices with a molecular weight cut-off of 10,000 kDa and a centrifugal force of 4500× g. The CENTRICONs™ were washed with 0.1 N NaOH (diluted from 1 N NaOH, Acros, for low endotoxin production) for one hour followed by several rinses with HyClone water prior to use. The final exchange factor was 300 fold into 1xDPBS. A total of 3 mL of concentrated and purified DX-88-PEG5K were recovered from the centricons. The final sample concentration, 4.97 mg/mL, was determined by diluting the sample 1:10 and measuring the O.D. 280 nm against 1xDPBS using an extinction coefficient for DX-88 of 0.954. The final sample pH was ~2 measured using Whatman pH Indicator strips (pH 0-14). All filtrates (33 mL total) were analyzed for protein content and had an O.D. 280 nm of 0.003 or less measured against 1xDPBS. The purified DX-88-PEG5K sample was aliquoted into 0.5 mL fractions (2.5 mg each) in sterile tubes and frozen at −80° C. The 1:10 diluted sample was analyzed by SDS-PAGE in a dilution series to estimate the purity of the main product of interest, 4-PEG5K-DX-88. The purity of 4-PEG5K-DX-88 is approximately 90%.

DX-890. We prepared a poly-PEGylated DX-890. Gel electrophoresis and chromatographic analysis indicated that a reaction with a 1:50 or 1:63 ratio of DX-890 to 5K PEG reagent produced a reaction product that was predominantly (>85%) a modified DX-890 with five attached PEG moieties. DX-890 pegylated under a variety of ratios maintained its specific activity relative to a control (about 10 U/mg).

Poly-pegylated DX-890 is predicted to have five PEG moieties (each having about 5,266 Daltons molecular weight) plus the mass of DX-890 (6,237 Daltons, theoretical; 6,229 Daltons, observed). The predicted total mass is 34,682 Daltons. The mass of the species observed by MALDI-TOF was about 34,219 Daltons, in agreement with the theoretical prediction, as the mass of individual PEG moieties can vary.

DX-88. We prepared a poly-PEGylated DX-88. Gel electrophoresis and chromatographic analysis indicated that a reaction with a 1:50 ratio of DX-890 to 5K PEG reagent at pH 7.8 produced a reaction product that was predominantly (>85%) a modified DX-88 with four attached PEG moieties.

Poly-pegylated DX-88 is predicted to have four PEG moieties (each having about 5,266 Daltons molecular weight) plus the mass of DX-88 (7,054 Daltons). The predicted total mass is 28,126 Daltons. The mass of the species observed by MALDI-TOF was about 29,680 Daltons, in agreement with the theoretical prediction, as the mass of individual PEG moieties can vary.

Other embodiments are within the following claims.

What is claimed is:

1. A compound comprising:
   (i) a Kunitz domain peptide that comprises the DX-890 amino acid sequence set forth in SEQ ID NO:23 or an amino acid sequence that differs by at least one, but no more than five, amino acid alterations from the DX-890 amino acid sequence set forth in SEQ ID NO:23 and that binds to and inhibits a protease; and
   (ii) a plurality of polyethylene glycol moieties covalently attached to at least each of four primary amines of the Kunitz domain peptide, wherein the average molecular weight of each of the moieties is between 3 kDa and 12 kDa.

2. The compound of claim 1 wherein the average molecular weight of each of the covalently attached polyethylene glycol moieties is between 3 kDa and 8 kDa.

3. The compound of claim 1 wherein the average molecular weight of each of the covalently attached polyethylene glycol moieties is between 4 kDa and 6 kDa.

4. The compound of claim 1 wherein the Kunitz domain peptide has a molecular weight less than 8 kDa, and the compound has a molecular weight greater than 16 kDa.

5. The compound of claim 1 wherein five polyethylene glycol moieties are each covalently attached to a different accessible primary amine.

6. The compound of claim 1 wherein each lysine of the Kunitz domain peptide is covalently attached to a polyethylene glycol moiety.

7. The compound of claim 6 wherein the Kunitz domain peptide comprises an N-terminal primary amine, and each lysine and the N-terminal primary amine is covalently attached to a polyethylene glycol moiety.

8. The compound of claim 1 wherein the Kunitz domain does not include a lysine in either of the Kunitz domain binding loop regions wherein said binding loop regions correspond to (i) the amino acid positions 11 through 21 and (ii) the amino acid positions 31 through 42 of the bovine pancreatic trypsin inhibitor (BPTI) amino acid sequence set forth in SEQ ID NO:2.

9. The compound of claim 1 wherein the Kunitz domain peptide-includes at least two lysines in the framework region of the Kunitz domain, wherein said framework region does not include either of the binding loop regions that correspond to (i) the amino acid positions 11 through 21 and (ii) the amino acid positions 31 through 42 of the bovine pancreatic trypsin inhibitor (BPTI) amino acid sequence set forth in SEQ ID NO:2.

10. The compound of claim 9 wherein the Kunitz domain peptide comprises three lysines in the framework region of the Kunitz domain.

11. The compound of claim 10 wherein the Kunitz domain peptide comprises four lysines in the framework region of the Kunitz domain.

12. The compound of claim 9 wherein the Kunitz domain peptide comprises a framework region the amino acid sequence of which is identical to a corresponding region of a human Kunitz domain.

13. The compound of claim 12 wherein the Kunitz domain peptide comprises a framework region the amino acid sequence of which is identical to the corresponding region in the inter-α-trypsin inhibitor (ITI) Kunitz domain having the amino acid sequence set forth in SEQ ID NO:12.

14. The compound of claim 1 wherein the compound comprises the DX-890 Kunitz domain peptide amino acid sequence set forth in SEQ ID NO:23.

15. The compound of claim 1 wherein the protease is elastase.

16. The compound of claim 15 wherein Kunitz domain peptide comprises an amino acid sequence that differs by one amino acid alteration from the DX-890 amino acid sequence set forth in SEQ ID NO:23.

17. The compound of claim 15 wherein the Kunitz domain polypeptide comprises the amino acid sequences of the two binding loop regions of DX-890 set forth in SEQ ID NO:23.

18. A preparation that comprises Kunitz domain peptides that comprise the DX-890 amino acid sequence set forth in SEQ ID NO:23 or an amino acid sequence that differs by at least one, but no more than five, amino acid alterations from the DX-890 amino acid sequence set forth in SEQ ID NO:23 and that specifically bind to and inhibit a protease, and wherein at least 80% of the Kunitz domain peptides in the preparation (i) bind and inhibit the protease, and (ii) have a polyethylene glycol moiety covalently attached at each of four lysine residues of the Kunitz domain and wherein the average molecular weight of each of the attached polyethylene glycol moieties is between 3 kDa and 12 kDa.

19. The preparation of claim 18 wherein the average molecular weight of each of the covalently attached polyethylene glycol moieties is between 3 kDa and 8 kDa.

20. The preparation of claim 19 wherein the average molecular weight of each of the covalently attached polyethylene glycol moieties is between 4 kDa and 6 kDa.

21. The preparation of claim 18 wherein at least 85% of the Kunitz domain peptides in the preparation have a polyethylene glycol moiety covalently attached at each of four lysine residues of the Kunitz domain peptide.

22. The preparation of claim 18 wherein the at least 80% of the Kunitz domain peptides in the preparation further have a further polyethylene glycol moiety covalently attached at the N-terminal primary amine of the Kunitz domain peptide.

23. The preparation of claim 22, wherein at least 85% of the Kunitz domain peptides in the preparation have a polyethylene glycol moiety covalently attached to each accessible primary amine.

24. The preparation of claim 18 wherein each of the Kunitz domain peptides in the preparation binds and inhibits the protease.

25. The preparation of claim 18 wherein 95% of the Kunitz domain peptides in the preparation bind and inhibit the protease.

26. The preparation of claim 18 wherein the at least 80% of the Kunitz domain peptides in the preparation have a polyethylene glycol moiety covalently attached to each accessible primary amine.

27. The preparation of claim 26, wherein at least 85% of the Kunitz domain peptides in the preparation have a polyethylene glycol moiety covalently attached to each accessible primary amine.

28. The preparation of claim 26 wherein, with respect to the at least 80% of the Kunitz domain peptides in the preparation, each lysine and the N-terminal primary amine is covalently attached to a polyethylene glycol moiety.

29. The preparation of claim 18 wherein the Kunitz domain peptides that specifically bind and inhibit the protease do not include a lysine in either of the Kunitz domain binding loop regions wherein said binding loop regions correspond to (i) the amino acid positions 11 through 21 and (ii) the amino acid positions 31 through 42 of the bovine pancreatic trypsin inhibitor (BPTI) amino acid sequence set forth in SEQ ID NO:2.

30. The preparation of claim 18 wherein the Kunitz domain peptides that specifically bind and inhibit the protease include at least two lysines in the framework region of the Kunitz domain wherein said framework region does not include either of the binding loop regions that correspond to (i) the amino acid positions 11 through 21 and (ii) the amino acid positions 31 through 42 of the bovine pancreatic trypsin inhibitor (BPTI) amino acid sequence set forth in SEQ ID NO:2.

31. The preparation of claim 30 wherein the Kunitz domain peptides that specifically bind and inhibit the protease include three lysines in the framework region of the Kunitz domain.

32. The preparation of claim 31 wherein the Kunitz domain peptides that specifically bind and inhibit the protease polypeptide include four lysines in the framework region of the Kunitz domain.

33. The preparation of claim 30 wherein the Kunitz domain peptides that specifically bind and inhibit the protease comprise a framework region that is identical to a corresponding region of a human Kunitz domain.

34. The preparation of claim 33 wherein the Kunitz domain peptides that specifically bind and inhibit the protease comprise a framework region the amino acid sequence of which is identical to the corresponding region in the inter-α-trypsin inhibitor (ITI) Kunitz domain having the amino acid sequence set forth in SEQ ID NO:12.

35. The preparation of claim 18, wherein the compound comprises the DX-890 Kunitz domain peptide amino acid sequence set forth in SEQ ID NO:23.

36. The preparation of claim 18 wherein the protease is elastase.

37. The preparation of claim 36 wherein, with respect to the at least 80% of the Kunitz domain peptides in the preparation, the Kunitz domain peptide comprises an amino acid sequence that differs by one amino acid alteration from the DX-890 amino acid sequence set forth in SEQ ID NO:23.

38. The preparation of claim 36 wherein, with respect to the at least 80% of the Kunitz domain peptides in the preparation, the Kunitz domain peptide comprises the amino acid sequences of the two binding loop regions of DX-890 set forth in SEQ ID NO:23.

39. A preparation that comprises Kunitz domain peptides that comprise the DX-890 amino acid sequence set forth in SEQ ID NO:23 or an amino acid sequence that differs by at least one, but no more than five, amino acid alterations from the DX-890 amino acid sequence set forth in SEQ ID NO:23 and that specifically bind to and inhibit a protease, and wherein at least 80% of the Kunitz domain peptides in the preparation (i) bind and inhibit the protease, and (ii) have at least four polyethylene glycol moieties covalently attached to primary amines of said Kunitz domain peptide and wherein the average molecular weight of each of the covalently attached polyethylene glycol moieties is between 3 kDa and 12 kDa.

40. The preparation of claim 39, wherein the compound comprises the DX-890 Kunitz domain peptide amino acid sequence set forth in SEQ ID NO:23.

41. A preparation that comprises Kunitz domain peptides that comprise a Kunitz domain that binds to and inhibits a protease and has the DX-890 amino acid sequence set forth in SEQ ID NO:23, wherein at least 80% of the DX-890-containing Kunitz domain peptides in the preparation have a polyethylene glycol moiety attached to each of four lysine residues and also to the N-terminus of the peptide.

42. The preparation of claim 41, wherein at least 85% of the DX-890-containing Kunitz domain peptides in the preparation have a polyethylene glycol moiety covalently attached to each of four lysine residues and to the N-terminus of the peptide.

43. A preparation comprising molecules that comprise:
   (i) a Kunitz domain peptide that comprises a Kunitz domain that comprises the DX-890 amino acid sequence set forth in SEQ ID NO:23 or an amino acid sequence that differs by at least one, but no more than five, amino acid alterations from the DX-890 amino acid sequence set forth in SEQ ID NO:23 and that binds to and inhibits a protease; and
   (ii) polyethylene glycol moieties covalently attached to at least four primary amines of the Kunitz domain peptide, wherein the average molecular weight of each of the polyethylene glycol moieties is between 3 kDa and 12 kDa.

44. The preparation of claim 43 wherein and the average molecular weight of each of the covalently attached polyethylene glycol moieties is between 3 kDa and 8 kDa.

45. The preparation of claim 43 wherein the Kunitz domains have polyethylene glycol moieties covalently attached to five primary amines and the average molecular weight of each of the polyethylene glycol moieties is between 3 kDa and 12 kDa.

46. The preparation of claim 45 wherein and the average molecular weight of each of the covalently attached polyethylene glycol moieties is between 3 kDa and 8 kDa.

47. The preparation of claim 43, wherein the compound comprises the DX-890 Kunitz domain peptide amino acid sequence set forth in SEQ ID NO:23.

48. A kit comprising the compound of claim 1 and informational material.

* * * * *